United States Patent
Ikeda et al.

(10) Patent No.: US 11,061,329 B2
(45) Date of Patent: Jul. 13, 2021

(54) RESIST COMPOSITION, METHOD OF FORMING RESIST PATTERN, POLYMERIC COMPOUND, AND COMPOUND

(71) Applicant: TOKYO OHKA KOGYO CO., LTD., Kawasaki (JP)

(72) Inventors: Takuya Ikeda, Kawasaki (JP); Masatoshi Arai, Kawasaki (JP)

(73) Assignee: Tokyo Ohka Kogyo Co., Ltd., Kawasaki (JP)

(*) Notice: Subject to any disclaimer, the term of this patent is extended or adjusted under 35 U.S.C. 154(b) by 141 days.

(21) Appl. No.: 16/173,326

(22) Filed: Oct. 29, 2018

(65) Prior Publication Data

US 2019/0163057 A1 May 30, 2019

(30) Foreign Application Priority Data

Nov. 29, 2017 (JP) .............. JP2017-229532

(51) Int. Cl.
| | |
|---|---|
| *G03F 7/039* | (2006.01) |
| *G03F 7/30* | (2006.01) |
| *C07C 69/54* | (2006.01) |
| *C07C 69/593* | (2006.01) |
| *C07C 69/753* | (2006.01) |
| *C08F 220/18* | (2006.01) |
| *C08F 222/14* | (2006.01) |
| *C08F 222/18* | (2006.01) |
| *C08F 222/20* | (2006.01) |
| *G03F 7/004* | (2006.01) |
| *C08L 67/04* | (2006.01) |

(52) U.S. Cl.
CPC ............ *G03F 7/0397* (2013.01); *C07C 69/54* (2013.01); *C07C 69/593* (2013.01); *C07C 69/753* (2013.01); *C08F 220/1806* (2020.02); *C08F 220/1807* (2020.02); *C08F 220/1808* (2020.02); *C08F 220/1809* (2020.02); *C08F 220/1811* (2020.02); *C08F 222/14* (2013.01); *C08F 222/145* (2020.02); *C08F 222/18* (2013.01); *C08F 222/185* (2020.02); *C08F 222/20* (2013.01); *C08F 222/205* (2020.02); *G03F 7/0045* (2013.01); *G03F 7/30* (2013.01); *C08L 67/04* (2013.01)

(58) Field of Classification Search
CPC ....... C07C 69/52; C07C 69/533; C07C 69/54; C07C 69/593; C07C 69/753; G03F 7/0397; G03F 7/30; G03F 7/38
See application file for complete search history.

(56) References Cited

U.S. PATENT DOCUMENTS

2003/0180662 A1* 9/2003 Nakano ................. G03F 7/0045
430/270.1

FOREIGN PATENT DOCUMENTS

WO WO 2011/040175 A1 4/2011

* cited by examiner

*Primary Examiner* — John S Chu
(74) *Attorney, Agent, or Firm* — Knobbe Martens Olson & Bear LLP

(57) ABSTRACT

A resist composition including a resin component having a structural unit derived form a compound represented by formula (a0-1) (in the formula, W represents a polymerizable group-containing group; $Ra^{01}$ is a group which is bonded to $Ra^{03}$ to form an aliphatic cyclic group, or bonded to $Ra^{04}$ to form an aliphatic cyclic group; $Ra^{02}$ represents a hydrocarbon group which may have a substituent; $Ra^{03}$ is a hydrogen atom or a monovalent organic group in the case where $Ra^{01}$ is not bonded thereto; $Ra^{04}$ is a hydrogen atom or a monovalent organic group in the case where $Ra^{01}$ is not bonded thereto; and $Ra^{05}$ to $Ra^{07}$ each independently represents a hydrogen atom or a monovalent organic group).

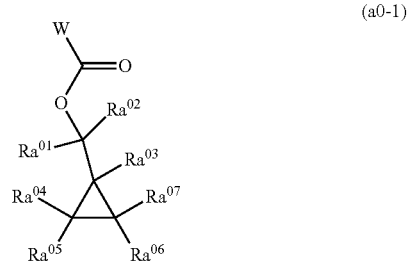

(a0-1)

4 Claims, No Drawings

RESIST COMPOSITION, METHOD OF FORMING RESIST PATTERN, POLYMERIC COMPOUND, AND COMPOUND

TECHNICAL FIELD

The present invention relates to a resist composition, a method of forming a resist pattern, a polymeric compound, and a compound.

Priority is claimed on Japanese Patent Application No. 2017-229532, filed Nov. 29, 2017, the content of which is incorporated herein by reference.

DESCRIPTION OF RELATED ART

In lithography techniques, for example, a resist film composed of a resist material is formed on a substrate, and the resist film is subjected to selective exposure, followed by development, thereby forming a resist pattern having a predetermined shape on the resist film. A resist material in which the exposed portions of the resist film become soluble in a developing solution is called a positive-type, and a resist material in which the exposed portions of the resist film become insoluble in a developing solution is called a negative-type.

In recent years, in the production of semiconductor elements and liquid crystal display elements, advances in lithography techniques have led to rapid progress in the field of pattern miniaturization. Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are used in mass production. Furthermore, research is also being conducted into lithography techniques that use an exposure light source having a wavelength shorter (energy higher) than these excimer lasers, such as electron beam (EB), extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified composition is used, which includes a base material component that exhibits a changed solubility in a developing solution under the action of acid and an acid-generator component that generates acid upon exposure.

For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If a resist film formed using such a resist composition is selectively exposed at the time of forming a resist pattern, in exposed areas, acid is generated from the acid generator component, and the polarity of the base resin increases by the action of the generated acid, thereby making the exposed areas of the resist film soluble in the alkali developing solution. Thus, by alkali developing, the exposed portions of the resist film are dissolved and removed, whereas the unexposed portions of the resist film remain as patterns, thereby forming a positive resist pattern.

On the other hand, when such a base resin is applied to a solvent developing process using a developing solution containing an organic solvent (organic developing solution), the solubility of the exposed portions in an organic developing solution is decreased. As a result, the unexposed portions of the resist film are dissolved and removed by the organic developing solution, and a negative resist pattern in which the exposed portions of the resist film are remaining is formed. Such a solvent developing process for forming a negative-tone resist composition is sometimes referred to as "negative-tone developing process".

In general, the base resin used for a chemically amplified resist composition contains a plurality of structural units for improving lithography properties and the like. For example, in the case of a resin composition which exhibits increased solubility in an alkali developing solution by the action of acid, a structural unit containing an acid decomposable group which is decomposed by the action of acid generated from an acid generator component and exhibits increased polarity. Further, a structural unit containing a lactone-containing cyclic group or a structural unit containing a polar group such as a hydroxy group is used in combination.

As the acid-generator component used in a chemically amplified resist composition, various kinds have been proposed. For example, onium salt acid generators such as iodonium salts and sulfonium salts; oxime sulfonate acid generators; diazomethane acid generators; nitrobenzylsulfonate acid generators; iminosulfonate acid generators; and disulfone acid generators are known.

As onium salt acid generators, those which have an onium ion such as triphenylsulfonium in the cation moiety are mainly used. Generally, as the anion moiety for onium salt acid generators, an alkylsulfonate ion or a fluorinated alkylsulfonate ion in which part or all of the hydrogen atoms within the aforementioned alkylsulfonate ion has been substituted with fluorine atoms is typically used.

In the formation of a resist pattern, the behavior of acid generated from the acid-generator component upon exposure and solubility of the resin component in a developing solution are some of the factors which has large influence on the lithography properties.

As the lithography technique further progresses and the miniaturization of the resist pattern progresses more and more, for example, a target of the lithography performed by extreme ultraviolet (EUV) or electron beam (EB) is to form fine resist patterns of several tens of nanometers. As miniaturization of resist pattern progress, resist composition is demanded to exhibit improved sensitivity to the exposure source and good lithography properties (resolution, reduced roughness, and the like).

In response to such demands, conventionally, various methods of changing the design of the base resin has been proposed. For example, there has been proposed a resist composition in which a polymer having a specific acid dissociable group containing an aryl group is employed to improve sensitivity and resolution (see, for example, Patent Literature 1).

DOCUMENTS OF RELATED ART

Patent Literature

[Patent Literature 1] WO2011/040175

SUMMARY OF THE INVENTION

However, conventional resist compositions had problems in that satisfactory resolution could not be achieved due to development defect, and it was difficult to obtain a resist pattern having a demanded shape.

The present invention takes the above circumstances into consideration, with an object of providing a polymeric compound useful as a base component of a resist composition, a compound which is a monomer of the polymeric compound, a resist composition containing the polymeric compound, and a method of forming a resist pattern using the resist composition.

For solving the above-mentioned problems, the present invention employs the following aspects.

Specifically, a first aspect of the present invention is a resist composition which generates acid upon exposure and exhibits changed solubility in a developing solution under action of acid, the resist composition including: a resin component (A1) which exhibits changed solubility in a developing solution under action of acid, the resin component (A1) including a structural unit (a0) derived from a compound represented by general formula (a0-1) shown below.

[Chemical Formula 1.]

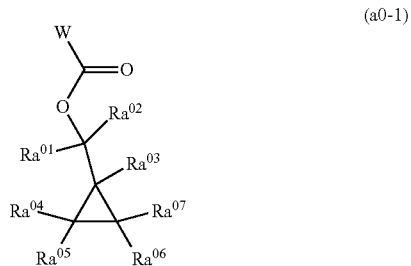

(a0-1)

In the formula, W represents a polymerizable group-containing group; $Ra^{01}$ is a group which is bonded to $Ra^{03}$ to form an aliphatic cyclic group together with the carbon atom to which $Ra^{03}$ is bonded and the carbon atom to which $Ra^{01}$ is bonded, or a group which is bonded to $Ra^{04}$ to form an aliphatic cyclic group together with the carbon atom to which $Ra^{04}$ is bonded, the carbon atom to which $Ra^{03}$ is bonded and the carbon atom to which $Ra^{01}$ is bonded; $Ra^{02}$ represents a hydrocarbon group which may have a substituent; $Ra^{03}$ is a hydrogen atom or a monovalent organic group in the case where $Ra^{01}$ is not bonded thereto; $Ra^{04}$ is a hydrogen atom or a monovalent organic group in the case where $Ra^{01}$ is not bonded thereto; and $Ra^{05}$ to $Ra^{07}$ each independently represents a hydrogen atom or a monovalent organic group.

A second aspect of the present invention is a method of forming a resist pattern, including: using a resist composition according to the first aspect to form a resist film, exposing the resist film, and developing the exposed resist film to form a resist pattern.

A third aspect of the present invention is a polymeric compound including a structural unit (a0) derived from a compound represented by the aforementioned general formula (a0-1).

A fourth aspect of the present invention is a compound represented by the aforementioned general formula (a0-1).

According to the present invention, there are provided a polymeric compound useful as a base component of a resist composition, a compound which is a monomer of the polymeric compound, a resist composition containing the polymeric compound, and a method of forming a resist pattern using the resist composition.

According to the resist composition of the present invention, sensitivity can be improved in the formation of a resist pattern, and it becomes possible to form a resist pattern exhibiting good lithography properties (resolution, reduced roughness, and the like).

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with a fluorine atom.

The term "structural unit" refers to a monomer unit that contributes to the formation of a polymeric compound (resin, polymer, copolymer).

The expression "may have a substituent" means that a case where a hydrogen atom (—H) is substituted with a monovalent group, or a case where a methylene (—CH$_2$—) group is substituted with a divalent group.

The term "exposure" is used as a general concept that includes irradiation with any form of radiation.

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid (CH$_2$=CH—COOH) has been substituted with an organic group.

The acrylate ester may have the hydrogen atom bonded to the carbon atom on the α-position substituted with a substituent. The substituent ($R^{\alpha 0}$) that substitutes the hydrogen atom bonded to the carbon atom on the α-position is an atom other than hydrogen or a group, and examples thereof include an alkyl group having 1 to 5 carbon atoms and a halogenated alkyl group having 1 to 5 carbon atoms. Further, an acrylate ester having the hydrogen atom bonded to the carbon atom on the α-position substituted with a substituent ($R^{\alpha 0}$) in which the substituent has been substituted with a substituent containing an ester bond (e.g., an itaconic acid diester), or an acrylic acid having the hydrogen atom bonded to the carbon atom on the α-position substituted with a substituent ($R^{\alpha 0}$) in which the substituent has been substituted with a hydroxyalkylgroup or a group in which the hydroxy group within a hydroxyalkyl group has been modified (e.g., α-hydroxyalkyl acrylate ester) can be mentioned as an acrylate ester having the hydrogen atom bonded to the carbon atom on the α-position substituted with a substituent. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester". Hereafter, an acrylate ester having the hydrogen atom bonded to the carbon atom on the α-position substituted with a substituent is sometimes referred to as "α-substituted acrylate ester". Further, acrylic acid and α-substituted acrylic acids are collectively referred to as "(α-substituted) acrylic acid".

A "structural unit derived from acrylamide" refers to a structural unit that is formed by the cleavage of the ethylenic double bond of acrylamide.

The acrylamide may have the hydrogen atom bonded to the carbon atom on the α-position substituted with a substituent, and may have either or both terminal hydrogen atoms on the amino group of acrylamide substituted with a substituent. A carbon atom on the α-position of an acrylamide refers to the carbon atom bonded to the carbonyl group, unless specified otherwise.

As the substituent which substitutes the hydrogen atom on the α-position of acrylamide, the same substituents as those described above for the substituent ($R^{\alpha 0}$) on the α-position of the aforementioned α-position of the aforementioned α-substituted acrylate ester can be mentioned.

A "structural unit derived from hydroxystyrene" refers to a structural unit that is formed by the cleavage of the ethylenic double bond of hydroxystyrene. A "structural unit derived from a hydroxystyrene derivative" refers to a structural unit that is formed by the cleavage of the ethylenic double bond of a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and may have the hydrogen atom on the α-position substituted with a substituent; and benzoic acid which has a substituent other than a hydroxy group and a carboxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

In the present specification and claims, some structures represented by chemical formulae may have an asymmetric carbon, such that an enantiomer or a diastereomer may be present. In such a case, the one formula represents all isomers. The isomers may be used individually, or in the form of a mixture.

(Resist Composition)

The resist composition of the present embodiment generates acid upon exposure and exhibits changed solubility in a developing solution under action of acid.

The resist composition contains a base component (A) (hereafter, sometimes referred to as "base component (A)") which exhibits changed solubility in a developing solution.

When a resist film is formed using the resist composition according to the present embodiment, and the resist film is selectively exposed, acid is generated at exposed portions of the resist film, and the solubility of the component (A) in a developing solution is changed by the action of the acid. On the other hand, at unexposed portions of the resist film, the solubility of the component (A) in a developing solution is unchanged. As a result, difference is generated between the exposed portions of the resist film and the unexposed portions of the resist film in terms of solubility in a developing solution. Therefore, by subjecting the resist film to development, the exposed portions of the resist film are dissolved and removed to form a positive-tone resist pattern in the case of a positive resist, whereas the unexposed portions of the resist film are dissolved and removed to form a negative-tone resist pattern in the case of a negative resist.

In the present specification, a resist composition which forms a positive resist pattern by dissolving and removing the exposed portions of the resist film is called a positive resist composition, and a resist composition which forms a negative resist pattern by dissolving and removing the unexposed portions of the resist film is called a negative resist composition.

The resist composition of the present embodiment may be either a positive resist composition or a negative resist composition.

Further, in the present embodiment, the resist composition may be applied to an alkali developing process using an alkali developing solution in the developing treatment, or a solvent developing process using a developing solution containing an organic solvent (organic developing solution) in the developing treatment, and preferably a solvent developing process.

That is, the resist composition of the present embodiment is preferably a resist composition which forms a positive pattern in an alkali developing process (i.e, a positive resist compound for alkali developing process) or a resist composition which forms a negative pattern in a solvent developing process (i.e., a negative type resist composition for solvent developing process).

The resist composition of the present embodiment is capable of generating acid upon exposure. The acid may be generated from the component (A) upon exposure, or the acid may be generated from an additive component other than the component (A) upon exposure.

In the present embodiment, the resist composition may be a resist composition (1) containing an acid generator component (B) which generates acid upon exposure (hereafter, referred to as "component (B)"; a resist composition (2) in which the component (A) is a component which generates acid upon exposure; or a resist composition (3) in which the component (A) is a component which generates acid upon exposure, and further containing an acid generator component (B).

That is, when the resist composition of the present invention is the aforementioned resist composition (2) or (3), the component (A) is a "base component which generates acid upon exposure and exhibits changed solubility in a developing solution under action of acid". In the case where the component (A) is a base component which generates acid upon exposure and exhibits changed solubility in a developing solution under action of acid, the component (A1) described later is preferably a polymeric compound which generates acid upon exposure and exhibits changed solubility in a developing solution under action of acid. As the polymeric compound, a resin having a structural unit which generates acid upon exposure may be used.

As the structural unit which generates acid upon exposure, a conventional structural unit may be used.

The resist composition of the present embodiment is most preferably the aforementioned resist composition (1).

<Component (A)>

The component (A) is a base component which exhibits changed solubility in a developing solution under action of acid.

In the present invention, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" or a "polymer" refers to a polymer having a molecular weight of 1,000 or more.

As the molecular weight of the polymer, the weight average molecular weight in terms of the polystyrene equivalent value determined by gel permeation chromatography (GPC) is used.

In the resist composition according to the present embodiment, the component (A) contains a resin component (A1) (hereafter, referred to as "component (A1)") which exhibits changed solubility in a developing solution by the action of acid.

As the component (A), at least the component (A1) is used, and a polymeric compound and/or a low molecular weight compound may be used in combination with the component (A1).

<<Component (A1)>>

The component (A1) includes a structural unit (a0) derived from a compound represented by general formula (a0-1) described later. If desired, the component (A1) may include, in addition to the structural unit (a0), other structural unit.

In the resist composition of the present embodiment, since the structural unit (a0) contains an acid dissociable group, by using the component (A1), the polarity of the resin component changes before and after exposure. Therefore, an excellent development contrast can be obtained between exposed portions and unexposed portions of the resist film not only in an alkali developing process, but also in a solvent developing process.

More specifically, in the case of applying an alkali developing process, the component (A1) is substantially insoluble in an alkali developing solution prior to exposure, but when acid is generated from the component (B) upon exposure, the action of this acid causes an increase in the polarity of the base component, thereby increasing the solubility of the component (A1) in an alkali developing solution. Therefore, in the formation of a resist pattern, by conducting selective exposure of a resist film formed by applying the resist composition to a substrate, the exposed portions of the resist film change from an insoluble state to a soluble state in an alkali developing solution, whereas the unexposed portions of the resist film remain insoluble in an alkali developing solution, and hence, a positive resist pattern is formed by alkali developing.

On the other hand, in the case of a solvent developing process, the component (A1) exhibits high solubility in an organic developing solution prior to exposure, and when acid is generated from the component (B) upon exposure for example, the polarity of the component (A1) is increased by the action of the generated acid, thereby decreasing the solubility of the component (A1) in an organic developing solution. Therefore, in the formation of a resist pattern, by conducting selective exposure of a resist film formed by applying the resist composition to a substrate, the exposed portions of the resist film changes from an soluble state to an insoluble state in an organic developing solution, whereas the unexposed portions of the resist film remain soluble in an organic developing solution. As a result, by conducting development using an organic developing solution, thereby forming a negative resist pattern.

Structural Unit (a0):

The structural unit (a0) is a structural unit derived from a compound represented by general formula (a0-1) shown below (compound (a00)). In the structural unit (a0), the tertiary carbon atom-containing group in formula (a0-1) is an acid dissociable group, and the acid dissociable group protects the oxy group (—O—) side of the carbonyloxy group [—C(=O)—O—] in formula (a0-1). The tertiary carbon atom-containing group in formula (a0-1) is the carbon atom to which both $Ra^{01}$ and $Ra^{02}$ are bonded.

An "acid dissociable group" exhibits acid dissociability such that the bond between the acid dissociable group and the adjacent oxygen atom (O) is cleaved by the action of acid. When the acid dissociable group is dissociated by the action of acid, a polar group which exhibits a higher polarity than the acid dissociable group is generated, and the polarity is increased.

As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

[Chemical Formula 2.]

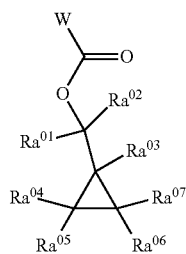

(a0-1)

In the formula, W represents a polymerizable group-containing group; $Ra^{01}$ is a group which is bonded to $Ra^{03}$ to form an aliphatic cyclic group together with the carbon atom to which $Ra^{03}$ is bonded and the carbon atom to which $Ra^{01}$ is bonded, or a group which is bonded to $Ra^{04}$ to form an aliphatic cyclic group together with the carbon atom to which $Ra^{04}$ is bonded, the carbon atom to which $Ra^{03}$ is bonded and the carbon atom to which $Ra^{01}$ is bonded; $Ra^{02}$ represents a hydrocarbon group which may have a substituent; $Ra^{03}$ is a hydrogen atom or a monovalent organic group in the case where $Ra^{01}$ is not bonded thereto; $Ra^{04}$ is a hydrogen atom or a monovalent organic group in the case where $Ra^{01}$ is not bonded thereto; and $Ra^{05}$ to $Ra^{07}$ each independently represents a hydrogen atom or a monovalent organic group.

In general formula (a0-1), W represents a polymerizable group-containing group.

The "polymerizable group" for W refers to a group that renders a compound containing the group polymerizable by a radical polymerization or the like, for example, a group having a carbon-carbon multiple bond such as an ethylenic double bond.

Examples of the polymerizable group include a vinyl group, an allyl group, an acryloyl group, a methacryloyl group, a fluorovinyl group, a difluorovinyl group, a trifluorovinyl group, a difluorotrifluoromethylvinyl group, a trifluoroallyl group, a perfluoroallyl group, a trifluoromethylacryloyl group, a nonylfluorobutylacryloyl group, a vinyl ether group, a fluorine-containing vinyl ether group, an allyl ether group, an fluorine-containing allyl ether group, a styryl group, a vinylnaphthyl group, a fluorine-containing styryl group, a fluorine-containing vinylnaphthyl group, a norbornyl group, a fluorine-containing norbornyl group, and a silyl group.

The polymerizable group-containing group may be a group constituted of only a polymerizable group, or a group constituted of a polymerizable group and a group other than a polymerizable group. Examples of the group other than a polymerizable group include a divalent hydrocarbon group which may have a substituent, and a divalent linking group containing a hetero atom.

Preferable example of W include a group represented by a chemical formula: $CH_2=C(R)-Ya^{x0}-$. In the chemical formula, R represents a hydrogen atom, an alkyl group having 1 to 5 carbon atoms or a halogenated alkyl group having 1 to 5 carbon atoms; and $Ya^{x0}$ represents a single bond or a divalent linking group.

In the aforementioned chemical formula, as the alkyl group having 1 to 5 carbon atoms for R, a linear or branched alkyl group having 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group having 1 to 5 carbon atoms represented by R is a group in which part or all of the hydrogen atoms of the aforementioned alkyl group having 1 to 5 carbon atoms have been substituted with halogen atoms. Examples of the halogen atom include a fluorine atom, a chlorine atom, a bromine atom and an iodine atom, and a fluorine atom is particularly desirable. As R, a hydrogen atom, an alkyl group having 1 to 5 carbon atoms or a fluorinated alkyl group having 1 to 5 carbon atoms is preferable, and in terms of industrial availability, a hydrogen atom or a methyl group is more preferable, and a methyl group is still more preferable.

In the aforementioned chemical formula, the divalent linking group for $Ya^{x0}$ is not particularly limited, and preferable examples thereof include a divalent hydrocarbon group which may have a substituent and a divalent linking group containing a hetero atom.

Divalent Hydrocarbon Group which May have a Substituent:

In the case where $Ya^{x0}$ is a divalent linking group which may have a substituent, the hydrocarbon group may be either an aliphatic hydrocarbon group or an aromatic hydrocarbon group.

Aliphatic Hydrocarbon Group for $Ya^{x0}$

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

Linear or Branched Aliphatic Hydrocarbon Group

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—($CH_2$)$_2$—], a trimethylene group [—($CH_2$)$_3$—], a tetramethylene group [—($CH_2$)$_4$—] and a pentamethylene group [—($CH_2$)$_5$—].

The branched aliphatic hydrocarbon group preferably has 2 to 10 carbon atoms, more preferably 3 to 6, still more preferably 3 or 4, and most preferably 3.

As the branched aliphatic hydrocarbon group, branched alkylene groups are preferred, and specific examples include various alkylalkylene groups, including alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; alkyltrimethylene groups such as —CH($CH_3$)$CH_2CH_2$—, and —$CH_2$CH($CH_3$)$CH_2$—; and alkyltetramethylene groups such as —CH(CH$_3$)CH$_2$CH$_2$CH$_2$—, and —CH$_2$CH(CH$_3$)CH$_2$CH$_2$—. As the alkyl group within the alkylalkylene group, a linear alkyl group having 1 to 5 carbon atoms is preferable.

The linear or branched aliphatic hydrocarbon group may or may not have a substituent. Examples of the substituent include a fluorine atom, a fluorinated alkyl group having 1 to 5 carbon atoms, and a carbonyl group.

Aliphatic Hydrocarbon Group Containing a Ring in the Structure Thereof

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which 2 hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group having 1 to 5 carbon atoms, and more preferably a methyl group, an ethyl group, a propyl group, an n-butyl group or a tert-butyl group.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and still more preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Aromatic Hydrocarbon Group for Ya$^{x0}$

The aromatic hydrocarbon group is a hydrocarbon group having at least one aromatic ring.

The aromatic ring is not particularly limited, as long as it is a cyclic conjugated compound having (4n+2)π electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Here, the number of carbon atoms within a substituent(s) is not included in the number of carbon atoms of the aromatic hydrocarbon group.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group having 1 to 5 carbon atoms, and more preferably a methyl group, an ethyl group, a propyl group, an n-butyl group or a tert-butyl group.

As the alkoxy group, the halogen atom and the halogenated alkyl group for the substituent, the same groups as the aforementioned substituent groups for substituting a hydrogen atom within the cyclic aliphatic hydrocarbon group can be used.

Divalent Linking Group Containing a Hetero Atom

In the case where Ya$^{x0}$ represents a divalent linking group containing a hetero atom, preferable examples of the linking group include —O—, —C(=O)—O—, —O—C(=O)—, —C(=O)—, —O—C(=O)—O—, —C(=O)—NH—, —NH—, —NH—C(=NH)— (may be substituted with a substituent such as an alkyl group, an acyl group or the like), —S—, —S(=O)$_2$—, —S(=O)$_2$—O—, and a group represented by general formula: —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represents a divalent hydrocarbon group which may have a substituent, O represents an oxygen atom, and m' represents an integer of 0 to 3].

In the case where the divalent linking group containing a hetero atom is —C(=O)—NH—, —C(=O)—NH—C(=O)—, —NH— or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In general formulae —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As $Y^{21}$, a linear aliphatic hydrocarbon group is preferable, more preferably a linear alkylene group, still more preferably a linear alkylene group having 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group having 1 to 5 carbon atoms, more preferably a linear alkyl group having 1 to 3 carbon atoms, and most preferably a methyl group.

In the group represented by the formula —[$Y^{21}$—C(=O)—O]$_{m''}$-$Y^{22}$—, m" represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m''}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

Among these examples, as Ya$^{x0}$, a single bond, an ester bond [—C(=O)—O—, —O—C(=O)—], an ether bond (—O—), a linear or branched alkylene group, or a combination thereof is preferable.

Among these, as Ya$^{x0}$, a single bond, an ester bond [—C(=O)—O—, —O—C(=O)—], a linear or branched alkylene group, or a combination of any of these groups is more preferable, and a single bond, or a combination of an ester bond [—C(=O)—O—] and a linear or branched alkylene group is most preferable.

That is, as W, a group represented by a chemical formula: CH$_2$=C(R)—*, or a group represented by a chemical formula: CH$_2$=C(R)—[C(=O)—O—Va$^0$]n$_{a00}$-* is most preferable. In the chemical formulae, "*" represents a valence bond.

In the chemical formula, Va$^0$ is a linear or branched alkylene group which may have an ether bond, preferably a linear alkylene group.

The linear alkylene group for Va$^0$ preferably has 1 to 10 carbon atoms, more preferably 1 to 6 carbon atoms, still more preferably 1 to 4 carbon atoms, and most preferably 1 to 3 carbon atoms. Specific examples include a methylene group [—CH$_2$—], an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

The branched alkylene group for Va$^0$ preferably has 2 to 10 carbon atoms, more preferably 3 to 6 carbon atoms, still more preferably 3 or 4 carbon atoms, and most preferably 3 carbon atoms. Specific examples include various alkylalkylene groups, including an alkylmethylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, or —C(CH$_2$CH$_3$)$_2$—; an alkylethylene group such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, or —C(CH$_2$CH$_3$)$_2$—CH$_2$—; an alkyltrimethylene group such as —CH(CH$_3$)CH$_2$CH$_2$—, or —CH$_2$CH(CH$_3$)CH$_2$—; and an alkyltetramethylene group such as —CH(CH$_3$)CH$_2$CH$_2$CH$_2$—, or —CH$_2$CH(CH$_3$)CH$_2$CH$_2$—. As the alkyl group within the alkylalkylene group, a linear alkyl group having 1 to 5 carbon atoms is preferable.

n$_{a00}$ is 1 or 2, and preferably 1.

In formula (a0-1), Ra$^{01}$ is a group which is bonded to Ra$^{03}$ to form an aliphatic cyclic group together with the carbon atom to which Ra$^{03}$ is bonded and the carbon atom (tertiary carbon atom) to which Ra$^{01}$, or a group which is bonded to Ra$^{04}$ to form an aliphatic cyclic group together with the carbon atom to which Ra$^{04}$ is bonded, the carbon atom to which Ra$^{03}$ and the carbon atom to which Ra$^{01}$ is bonded.

In the case where Ra$^{01}$ is bonded to Ra$^{03}$, the aliphatic ring formed of Ra$^{01}$, Ra$^{03}$, the carbon atom to which Ra$^{03}$ is bonded and the carbon atom (tertiary carbon atoms) to which Ra$^{01}$ is bonded may be polycyclic or monocyclic. In this case, the aliphatic ring has a 3-membered ring which shares the carbon atom to which Ra$^{03}$ is bonded. In this case, in terms of solubility in a developing solution, the aliphatic ring is preferably monocyclic. The aliphatic monocyclic ring is preferably an aliphatic monocyclic group having 4 to 8 carbon atoms, more preferably cyclopentane or cyclohexane, and most preferably cyclopentane.

In the case where Ra$^{01}$ is bonded to Ra$^{04}$, the aliphatic ring formed of Ra$^{01}$, Ra$^{04}$, the carbon atom to which Ra$^{04}$ is bonded, the carbon atom to which Ra$^{03}$ is bonded and the carbon atom (tertiary carbon atom) to which Ra$^{01}$ is bonded may be polycyclic or monocyclic. In this case, the aliphatic ring is condensed with a 3-membered ring which shares the carbon atom to which Ra$^{03}$ is bonded and the carbon atom to which Ra$^{04}$ is bonded. In this case, in terms of solubility in a developing solution, the aliphatic ring is preferably monocyclic. The aliphatic monocyclic ring is preferably an aliphatic monocyclic group having 4 to 8 carbon atoms, more preferably cyclopentane or cyclohexane, and most preferably cyclopentane.

In formula (a0-1), Ra$^{02}$ represents a hydrocarbon group which may have a substituent.

Examples of the hydrocarbon group for Ra$^{02}$ include a linear or branched alkyl group, a chain or cyclic alkenyl group, and a cyclic hydrocarbon group.

The linear alkylene group for Ra$^{02}$ preferably has 1 to 10 carbon atoms, more preferably 1 to 5 carbon atoms, still more preferably 1 to 4 carbon atoms, and most preferably 1 or 2 carbon atoms. Specific examples include a methyl group, an ethyl group, an n-propyl group, an n-butyl group, and an n-pentyl group. Among these examples, a methyl group, an ethyl group or an n-butyl group is preferable.

The branched alkyl group for Ra$^{02}$ preferably has 3 to 10 carbon atoms, more preferably 3 to 7 carbon atoms, and still more preferably 3 to 5 carbon atoms. Specific examples include an isopropyl group, an isobutyl group, a tert-butyl group, an isopentyl group, a neopentyl group, a sec-pentyl group, a tert-pentyl group, a 1,1-diethylpropyl group and a 2,2-dimethylbutyl group. Among these, an isopropyl group, a tert-butyl group or a tert-pentyl group is preferable.

Examples of the chain or cyclic alkenyl group for $Ra^{02}$ include a group represented by chemical formula: *—C($Ra^{011}$)=C($Ra^{021}$)($Ra^{022}$).

In the chemical formula, * indicates the valence bond which is bonded to the carbon atom (tertiary carbon atom) to which $Ra^{01}$ is bonded.

$Ra^{011}$, $Ra^{021}$ and $Ra^{022}$ each independently represents a hydrogen atom, a monovalent saturated chain hydrocarbon group having 1 to 10 carbon atoms or a monovalent saturated aliphatic cyclic hydrocarbon group having 3 to 20 carbon atoms, provided that part or all of the hydrogen atoms of the saturated chain hydrocarbon or the saturated aliphatic cyclic hydrocarbon may be substituted; two or more of $Ra^{011}$, $Ra^{021}$ and $Ra^{022}$ may be mutually bonded to form a cyclic structure.

Examples of the monovalent saturated chain hydrocarbon group having 1 to 10 carbon atoms for $Ra^{011}$, $Ra^{021}$ and $Ra^{022}$ include a methyl group, an ethyl group, a propyl group, a butyl group, a pentyl group, a hexyl group, a heptyl group, an octyl group, and a decyl group.

Examples of the monovalent saturated aliphatic cyclic hydrocarbon group having 3 to 20 carbon atoms for $Ra^{011}$, $Ra^{021}$ and $Ra^{022}$ include a monocyclic saturated aliphatic hydrocarbon group such as a cyclopropyl group, a cyclobutyl group, a cyclopentyl group, a cyclohexyl group, a cycloheptyl group, a cyclooctyl group, a cyclodecyl group or a cyclododecyl group; and a polycyclic saturated aliphatic hydrocarbon group such as a bicyclo[2.2.2]octanyl group, a tricyclo[5.2.1.02,6]decanyl group, a tricyclo[3.3.1.13,7]decanyl group, a tetracyclo[6.2.1.13,6.02,7]dodecanyl group or an adamantyl group.

Among the above examples, as $Ra^{011}$, $Ra^{021}$ and $Ra^{022}$, in terms of ease in synthesis of the compound which derives the structural unit (a0), a hydrogen atom or a monovalent saturated chain hydrocarbon group having 1 to 10 carbon atoms is preferable, a hydrogen atom, a methyl group or an ethyl group is more preferable, and a hydrogen atom is most preferable.

Examples of the substituent for a chain saturated hydrocarbon group or saturated aliphatic cyclic hydrocarbon group for $Ra^{011}$, $Ra^{021}$ and $Ra^{022}$ include —$R^{P1}$, —$R^{P2}$—O—$R^{P1}$, —$R^{P2}$—CO—$R^{P1}$, —$R^{P2}$—CO—O$R^{P1}$, —$R^{P2}$—O—CO—$R^{P1}$, —$R^{P2}$—OH, —$R^{P2}$—CN and —$R^{P2}$—COOH.

Here, $R^{P1}$ is a monovalent chain saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. Further, $R^{P2}$ is a single bond, a divalent chain saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms.

Here, a portion or all of the hydrogen atoms having the chain saturated hydrocarbon group, the aliphatic cyclic saturated hydrocarbon group, and the aromatic hydrocarbon group for $R^{P1}$ and $R^{P2}$ may be substituted with a fluorine atom. The aliphatic cyclic hydrocarbon group may have 1 or more substituents of 1 kind, or 1 or more substituents of a plurality of kinds.

Examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.02,6]decanyl group, a tricyclo[3.3.1.13,7]decanyl group, a tetracyclo[6.2.1.13,6.02,7]dodecanyl group, and an adamantyl group.

Examples of the monovalent aromatic hydrocarbon group having 6 to 30 carbon atoms include a group obtained by removing one hydrogen atom from the aromatic hydrocarbon ring such as benzene, biphenyl, fluorene, naphthalene, anthracene, and phenanthrene.

Examples of the group containing a carbon-carbon double bond formed by two or more of $Ra^{011}$, $Ra^{021}$ and $Ra^{022}$ mutually bonded to form a ring structure include a cyclopentenyl group, a cyclohexenyl group, a methylcyclopentenyl group, a methylcyclohexenyl group, a cyclopentylideneethenyl group, and a cyclohexylideneethenyl group. Among these examples, in terms of ease in synthesis of the compound which derives the structural unit (a0), a cyclopentenyl group, a cyclohexenyl group or a cyclopentylideneethenyl group is preferable.

The cyclic hydrocarbon group for $Ra^{02}$ may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

Examples of the aromatic hydrocarbon group include a group in which 1 or more hydrogen atoms have been removed from an aromatic hydrocarbon ring having 5 to 30 carbon atoms. Among these examples, as $Ra^{02}$, a group in which 1 or more hydrogen atoms have been removed from an aromatic hydrocarbon ring having 6 to 15 carbon atoms is preferable, a group in which 1 or more hydrogen atoms have been removed from benzene, naphthalene, anthracene or phenanthrene is more preferable, a group in which 1 or more hydrogen atoms have been removed from benzene, naphthalene or anthracene is still more preferable, and a group in which 1 or more hydrogen atoms have been removed from benzene is most preferable.

Examples of the substituent for the hydrocarbon group represented by $Ra^{02}$ include a methyl group, an ethyl group, a propyl group, a hydroxyl group, a carboxy group, a halogen atom (such as a fluorine atom, a chlorine atom or a bromine atom), an alkoxy group (such as a methoxy group, an ethoxy group, a propoxy group or a butoxy group), and an alkyloxycarbonyl group. Further, the hydrocarbon group for $Ra^{02}$ may have an ether bond, an ester bond or the like between the carbon atoms constituting the hydrocarbon group.

Alternative examples of the hydrocarbon group for $Ra^{o2}$ include a group represented by chemical formula: *—$Ya^o$($Ra^{o31}$)($Ra^{o32}$)($Ra^{o33}$).

In the chemical formula, * indicates the valence bond which is bonded to the carbon atom (tertiary carbon atom) to which $Ra^{o1}$ is bonded.

$Ya^o$ represents a quaternary carbon atom. $Ra^{o31}$, $Ra^{o32}$ and $Ra^{o33}$ each independently represents a hydrocarbon group which may have a substituent. However, at least one of $Ra^{o31}$, $Ra^{o32}$ and $Ra^{o33}$ is a hydrocarbon group having a polar group.

In the chemical formula, $Ya^o$ is a quaternary carbon atom. That is, the number of carbon atoms bonded to $Ya^o$ (carbon atom) is 4.

Examples of the hydrocarbon group (which may have a substituent) for $Ra^{o31}$, $Ra^{o32}$ and $Ra^{o33}$ include a linear or branched alkyl group, a chain or cyclic alkenyl group, and a cyclic hydrocarbon group.

The linear alkyl group for $Ra^{o31}$, $Ra^{o32}$ and $Ra^{o33}$ preferably has 1 to 5 carbon atoms, more preferably 1 to 4 carbon atoms, and still more preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group for $Ra^{o31}$, $Ra^{o32}$ and $Ra^{o33}$ preferably has 3 to 10 carbon atoms, and more preferably 3 to 5 carbon atoms. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

The chain or cyclic alkenyl group for $Ra^{o31}$, $Ra^{o32}$ and $Ra^{o33}$ is preferably an alkenyl group having 2 to 10 carbon atoms.

The cyclic hydrocarbon group for $Ra^{o31}$, $Ra^{o32}$ and $Ra^{o33}$ may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group for $Ra^{o31}$, $Ra^{o32}$ and $Ra^{o33}$ is a hydrocarbon group having at least one aromatic ring. The aromatic ring is not particularly limited, as long as it is a cyclic conjugated compound having (4n+2) π electrons, and may be either monocyclic or polycyclic. The aromatic ring preferably has 5 to 30 carbon atoms, more preferably 5 to 20, still more preferably 6 to 15, and most preferably 6 to 12. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring. Specific examples of the aromatic hydrocarbon group include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

In the case where the hydrocarbon group for $Ra^{o31}$, $Ra^{o32}$ and $Ra^{o33}$ is substituted, examples of the substituent include a hydroxy group, a carboxy group, a halogen atom (such as a fluorine atom, a chlorine atom or a chlorine atom), an alkoxy group (such as a methoxy group, an ethoxy group, a propoxy group or a butoxy group), and an alkyloxycarbonyl group.

Among these examples, as the hydrocarbon group (which may have a substituent) for $Ra^{o31}$, $Ra^{o32}$ and $Ra^{o33}$, a linear or branched alkyl group which may have a substituent is preferable, and a linear alkyl group is more preferable.

However, at least one of $Ra^{o31}$, $Ra^{o32}$ and $Ra^{o33}$ is a hydrocarbon group having a polar group.

The "hydrocarbon group having a polar group" includes a group in which a polar group is present between carbon chains (carbon atoms) and a group in which at least one hydrogen atom constituting the hydrocarbon group has been substituted with a polar group.

Examples of the "hydrocarbon group having a polar group" include a functional group represented by general formula (a0-p1) shown below.

[Chemical Formula 3.]

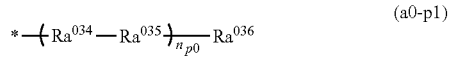

(a0-p1)

In the formula, $Ra^{o34}$ represents a divalent hydrocarbon group having 2 to 12 carbon atoms; $Ra^{o35}$ represents a divalent linking group containing a hetero atom; $Ra^{o36}$ represents a monovalent hydrocarbon group having 1 to 12 carbon atoms; $n_{p0}$ represents an integer of 1 to 6; * represents a valence bond which is bonded to the quaternary carbon atom ($Ya^o$).

In formula (a0-p1), $Ra^{o34}$ represents a divalent hydrocarbon group having 2 to 12 carbon atoms.

$Ra^{o34}$ has 2 to 12 carbon atoms, preferably 2 to 8 carbon atoms, more preferably 2 to 6 carbon atoms, still more preferably 2 to 4 carbon atoms, and most preferably 2 carbon atoms.

The hydrocarbon group for $Ra^{o34}$ is preferably a chain or cyclic aliphatic hydrocarbon group, and more preferably a chain hydrocarbon group.

Examples of $Ra^{o34}$ include a linear alkanediyl group, such as an ethylene group, a propane-1,3-diyl group, butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, and a dodecane-1,12-diyl group; a branched alkanediyl group, such as a propane-1,2-diyl group, a 1-methylbutane-1,3-diyl group, a 2-methylpropane-1,3-diyl group, a pentane-1,4-diyl group, and a 2-methylbutane-1,4-diyl group; a cycloalkanediyl group, such as a cyclobutane-1,3-diyl group, a cyclopentane-1,3-diyl group, a cyclohexane-1,4-diyl group, and a cyclooctane-1,5-diyl group; and a polycyclic divalent alicyclic hydrocarbon group, such as a norbornane-1,4-diyl group, a norbornane-2,5-diyl group, an adamantane-1,5-diyl group, and an adamantane-2,6-diyl group.

Among these examples, an alkanediyl group is preferable, and a linear alkanediyl group is more preferable.

In formula (a0-p1), $Ra^{035}$ represents a divalent linking group containing a hetero atom.

Examples of $Ra^{035}$ include —O—, —C(=O)—O—, —C(=O)—, —O—C(=O)—O—, —C(=O)—NH—, —NH—, —NH—C(=NH)— (H may be substituted with a substituent such as an alkyl group or an acyl group), —S—, —S(=O)$_2$—, and —S(=O)$_2$—O—.

Among these examples, in terms of solubility in a developing solution, —O—, —C(=O)—O—, —C(=O)—, or —O—C(=O)—O— are preferable, and —O— or —C(=O)— is most preferable.

In formula (a0-p1), $Ra^{036}$ represents a monovalent hydrocarbon group having 1 to 12 carbon atoms.

$Ra^{036}$ has 1 to 12 carbon atoms. In terms of solubility in a developing solution, $Ra^{036}$ preferably has 1 to 8 carbon atoms, more preferably 1 to 5 carbon atoms, still more preferably 1 to 3 carbon atoms, still more preferably 1 or 2 carbon atoms, and most preferably 1 carbon atoms.

Examples of the hydrocarbon group for $Ra^{036}$ include a chain hydrocarbon group, a cyclic hydrocarbon group, and a combination of a chain hydrocarbon group and a cyclic hydrocarbon group.

Examples of the chain hydrocarbon group include a methyl group, an ethyl group, an n-propyl group, an isopropyl group, an n-butyl group, a sec-butyl group, a tert-butyl group, an n-pentyl group, an n-hexyl group, an n-heptyl group, a 2-ethylhexyl group, an n-octyl group, an n-nonyl group, an n-decyl group, an n-undecyl group and an n-dodecyl group.

The cyclic hydrocarbon group may be an alicyclic hydrocarbon group or an aromatic hydrocarbon group.

The alicyclic hydrocarbon group may be monocyclic or polycyclic. Examples of monocyclic alicyclic hydrocarbon groups include cycloalkyl groups, such as a cyclopropyl group, a cyclobutyl group, a cyclopentyl group, a cyclohexyl group, a dimethylcyclohexyl group, a cycloheptyl group, a cyclooctyl group, a cycloheptyl group, and a cyclodecyl group. Examples of polycyclic alicyclic hydrocarbon groups include a decahydronaphthyl group, an adamantyl group, a 2-alkyladamantan-2-yl group, a 1-(adamantan-1-yl)alkan-1-yl group, a norbornyl group, a methylnorbornyl group, and an isonorbornyl group.

Examples of aromatic hydrocarbon groups include a phenyl group, a naphthyl group, an anthryl group, a p-methylphenyl group, a p-tert-butylphenyl group, a p-adamantylphenyl group, a tolyl group, a xylyl group, a cumenyl group, a mesityl group, a biphenyl group, a phenanthryl group, 2,6-diethylphenyl group, and 2-methyl-6-ethyl phenyl group.

In terms of solubility in a developing solution, $Ra^{036}$ is preferably a chain hydrocarbon group, more preferably an alkyl group, and still more preferably a linear alkyl group.

In formula (a0-p1), $n_{p0}$ is an integer of 1 to 6, preferably an integer of 1 to 3, more preferably 1 or 2, and still more preferably 1.

Specific examples of the hydrocarbon group having a polar group are shown below.

In the following formulae, * represents a valence bond which is bonded to the quaternary carbon atom ($Ya^0$).

[Chemical Formula 4.]

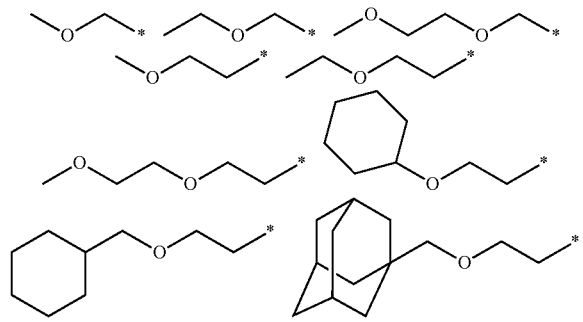

In the group represented by the aforementioned chemical formula:
*—$Ya^0(Ra^{031})(Ra^{032})(Ra^{033})$, at least one of $Ra^{031}$, $Ra^{032}$ and $Ra^{033}$ may be a hydrocarbon group having a polar group. The number of hydrocarbon groups having a polar group may be appropriately selected, taking into consideration of the solubility in a developing solution in the formation of a resist pattern. For example, it is preferable that one or two of $Ra^{031}$, $Ra^{032}$ and $Ra^{033}$ is a hydrocarbon group having a polar group, and it is more preferable that one of $Ra^{031}$, $Ra^{032}$ and $Ra^{033}$ is a hydrocarbon group having a polar group.

The hydrocarbon group having a polar group may have a substituent other than a polar group.

Examples of such substituent include a halogen atom (such as a fluorine atom, a chlorine atom or a bromine atom), and a halogenated alkyl group having 1 to 5 carbon atoms.

Among these examples, as $Ra^{02}$, a linear or branched alkyl group or a chain or cyclic alkenyl group is preferable, a linear alkyl group or a chain alkenyl group is more preferable, and a linear alkyl group is still more preferable.

In formula (a0-1), $Ra^{03}$ is a hydrogen atom or a monovalent organic group in the case where $Ra^{01}$ is not bonded thereto.

In formula (a0-1), $Ra^{04}$ is a hydrogen atom or a monovalent organic group in the case where $Ra^{01}$ is not bonded thereto.

In formula (a0-1), $Ra^{05}$ to $Ra^{07}$ each independently represents a hydrogen atom or a monovalent organic group.

Examples of the monovalent organic group for $Ra^{03}$, $Ra^{04}$, and $Ra^{05}$ to $Ra^{07}$ include an alkyl group, an alkoxy group, a halogenated alkyl group, and a hydroxyalkyl group.

The alkyl group is preferably an alkyl group having 1 to 5 carbon atoms, and examples thereof include a methyl group, an ethyl group, a propyl group, an n-butyl group and a tert-butyl group. Among these examples, a methyl group or an ethyl group is preferable.

The alkoxy group is preferably an alkoxy group having 1 to 5 carbon atoms, and examples thereof include a methoxy group, an ethoxy group, an n-propoxy group, an iso-propoxy group, an n-butoxy group and a tert-butoxy group.

Examples of the halogenated alkyl group include a group in which part or all of the hydrogen atoms of the aforementioned alkyl group has been substituted with a halogen atom. As the halogenated alkyl group, a group in which part or all of the hydrogen atoms of an alkyl group having 1 to 5 carbon atoms have been substituted with a halogen atom is preferable. Examples of the halogen atom include a fluorine atom, a chlorine atom, a bromine atom and an iodine atom.

Examples of the hydroxyalkyl group include a group in which part or all of the hydrogen atoms of the aforementioned alkyl group has been substituted with a hydroxy group. As the hydroxyalkyl group, a group in which part or all of the hydrogen atoms of an alkyl group having 1 to 5 carbon atoms have been substituted with a hydroxy group is preferable.

In formula (a0-1), in terms of solubility in a developing solution, $Ra^{05}$ to $Ra^{07}$ is preferably a hydrogen atom or an alkyl group, more preferably a hydrogen atom or an alkyl group having 1 to 5 carbon atoms, still more preferably a hydrogen atom or a methyl group, and most preferably a hydrogen atom.

In the case where $Ra^{01}$ is not bonded to $Ra^{03}$, in terms of solubility in a developing solution, $Ra^{03}$ is preferably a hydrogen atom or an alkyl group, more preferably a hydrogen atom or an alkyl group having 1 to 5 carbon atoms, still more preferably a hydrogen atom or a methyl group, and most preferably a hydrogen atom. In the case where $Ra^{01}$ is not bonded to $Ra^{04}$, in terms of solubility in a developing solution, $Ra^{04}$ is preferably a hydrogen atom or an alkyl group, more preferably a hydrogen atom or an alkyl group having 1 to 5 carbon atoms, still more preferably a hydrogen atom or a methyl group, and most preferably a hydrogen atom.

In formula (a0-1), the total number of carbon atoms of $Ra^{01}$ and $Ra^{03}$ to $Ra^{07}$ is preferably 13 or less, more preferably 6 to 12, and still more preferably 6 to 10.

When the total number of carbon atoms is no more than the upper limit of the above-mentioned preferable range, development defect is unlikely to occur, and the resolution may be further improved. On the other hand, when the total number of carbon atoms is at least as large as the lower limit of the above-mentioned preferable range, increase in the solubility of the resin component in a developing solution by the action of acid may be further improved.

Preferable examples of the compound represented by general formula (a0-1) include a compound represented by general formula (a0-1-1) or (a0-1-2) shown below.

[Chemical Formula 5.]

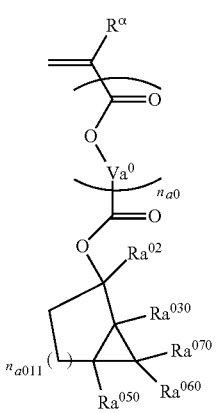

(a0-1-1)

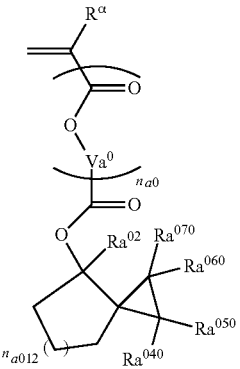

(a0-1-2)

In formula (a0-1-1), $R^{\alpha}$ represents a hydrogen atom, a methyl group or a trifluoromethyl group; $Va^0$ represents a linear or branched alkylene group which may have an ether bond; $n_{a0}$ represents an integer of 0 to 2; $n_{a011}$ represents an integer of 1 to 4; $Ra^{02}$ represents a hydrocarbon group which may have a substituent; $Ra^{030}$ represents a hydrogen atom or an alkyl group having 1 to 5 carbon atoms; $Ra^{050}$ to $Ra^{070}$ each independently represents a hydrogen atom or an alkyl group having 1 to 5 carbon atoms; in formula (a0-1-2), $R^{\alpha}$ represents a hydrogen atom, a methyl group or a trifluoromethyl group; $Va^0$ represents a linear or branched alkylene group which may have an ether bond; $n_{a0}$ represents an integer of 0 to 2; $n_{a012}$ represents an integer of 1 to 4; $Ra^{02}$ represents a hydrocarbon group which may have a substituent; $Ra^{040}$ represents a hydrogen atom or an alkyl group having 1 to 5 carbon atoms; and $Ra^{050}$ to $Ra^{070}$ each independently represents a hydrogen atom or an alkyl group having 1 to 5 carbon atoms.

In formula (a0-1-1) and (a0-1-2), $Va^0$ is the same as defined for the aforementioned $Va^0$, preferably a linear alkylene group, and more preferably a linear alkylene group having 1 to 6 carbon atoms.

In formula (a0-1-1) and (a0-1-2), $n_{a0}$ is an integer of 0 to 2, preferably 0 or 1, and more preferably 0.

In formula (a0-1-1) and (a0-1-2), $Ra^{02}$ is the same as defined for the aforementioned $Ra^{02}$, and examples thereof include a linear or branched alkyl group which may have a substituent, a chain or cyclic alkenyl group which may have a substituent, and a cyclic hydrocarbon group which may have a substituent.

In formula (a0-1-1), $Ra^{030}$ represents a hydrogen atom or an alkyl group having 1 to 5 carbon atoms, preferably a hydrogen atom or a methyl group, and more preferably a hydrogen atom.

$Ra^{050}$ to $Ra^{070}$ each independently represents a hydrogen atom or an alkyl group having 1 to 5 carbon atoms, preferably a hydrogen atom or a methyl group, and more preferably a hydrogen atom.

In formula (a0-1-2), $Ra^{040}$ represents a hydrogen atom or an alkyl group having 1 to 5 carbon atoms, preferably a hydrogen atom or a methyl group, and more preferably a hydrogen atom.

$Ra^{050}$ to $Ra^{070}$ each independently represents a hydrogen atom or an alkyl group having 1 to 5 carbon atoms, preferably a hydrogen atom or a methyl group, and more preferably a hydrogen atom.

Specific examples of the structural unit (a0) derived from a compound represented by the aforementioned general formula (a0-1) are shown below.

In the formulae shown below, $R^\alpha$ represents a hydrogen atom, a methyl group or a trifluoromethyl group.
[Chemical Formula 6.]
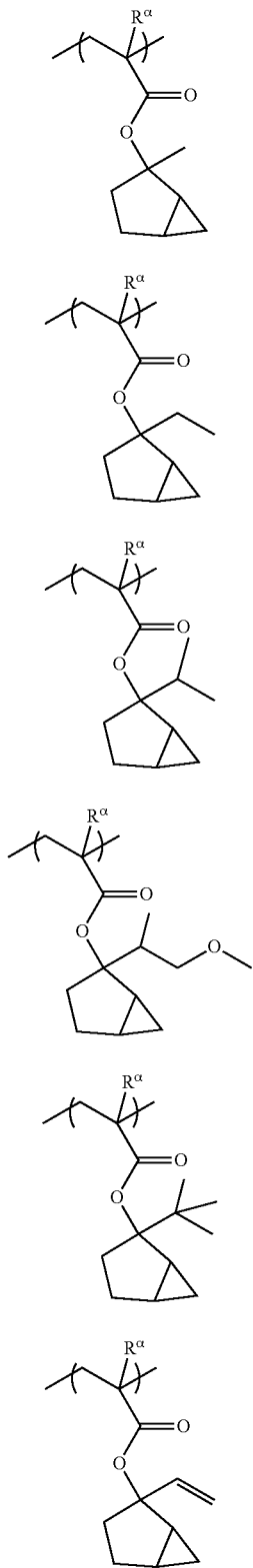
(a0-1-101)
(a0-1-102)
(a0-1-103)
(a0-1-104)
(a0-1-105)
(a0-1-106)
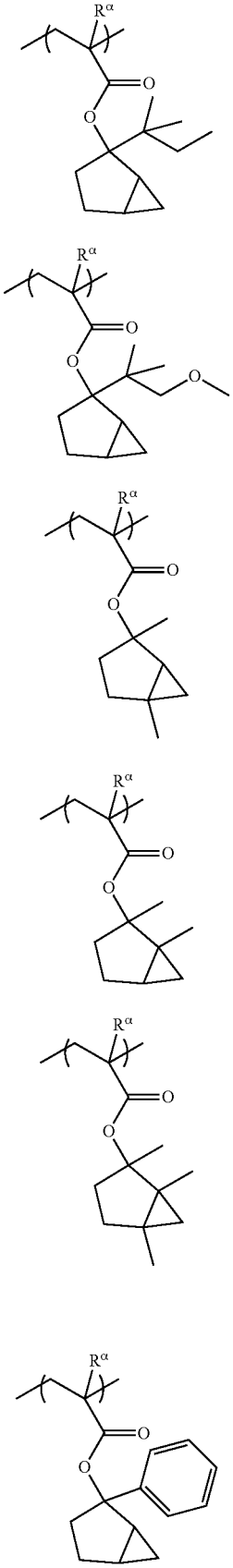
(a0-1-107)
(a0-1-108)
(a0-1-109)
(a0-1-110)
(a0-1-111)
(a0-1-112)

(a0-1-113)
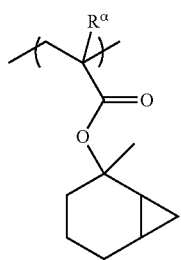
(a0-1-114)
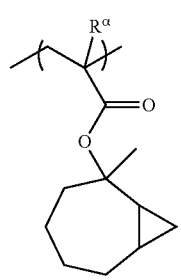
(a0-1-115)
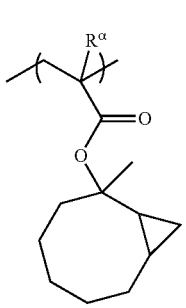
[Chemical Formula 7.]
(a0-1-201)
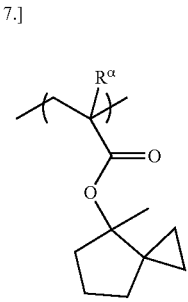
(a0-1-202)
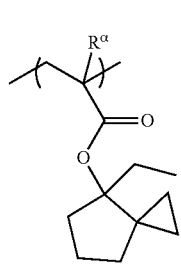
(a0-1-203)
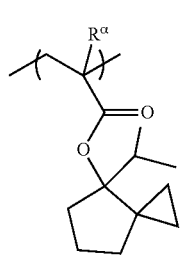
(a0-1-204)
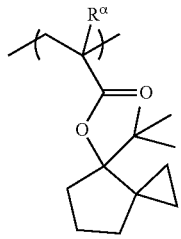
(a0-1-205)
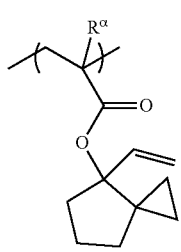
(a0-1-206)
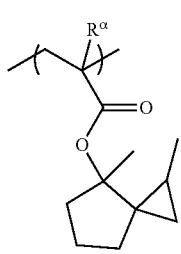
(a0-1-207)
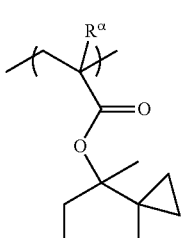
(a0-1-208)
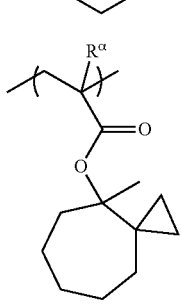
(a0-1-209)
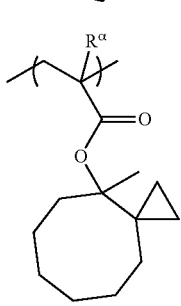
Among the above examples, as the structural unit (a0), at least one member selected from the group consisting of a structural unit derived from a compound represented by general formula (a0-1-1) and a structural unit derived from a compound represented by general formula (a0-1-2) is preferable.

Among these, as the structural unit (a0), at least one member selected from the group consisting of structural units represented by chemical formulae (a0-1-101) to (a0-1-115) and chemical formulae (a0-1-201) to (a0-1-209) is preferable, and at least one member selected from the group consisting of structural units represented by chemical formulae (a0-1-101), (a0-1-102), (a0-1-106), (a0-1-109), (a0-1-113) and (a0-1-114) is more preferable.

As the structural unit (a0) contained in the component (A1), 1 kind of structural unit may be used, or 2 or more kinds of structural units may be used.

In the component (A1), the amount of the structural unit (a0) based on the combined total (100 mol %) of all structural units constituting the component (A1) is preferably 20 to 80 mol %, more preferably 30 to 75 mol %, and still more preferably 40 to 70 mol %.

When the amount of the structural unit (a0) is at least as large as the lower limit of the above preferable range, a resist pattern may be reliably obtained, and various lithography properties such as resolution and roughness may be further improved. On the other hand, when the amount is no more than the upper limit of the above preferable range, a good balance may be achieved with the other structural units.

Other Structural Units:

If desired, the component (A1) may include, in addition to the structural unit (a0), other structural unit.

Examples of other structural units include a structural unit (a1) containing an acid decomposable group that exhibits increased polarity by the action of acid, (provided that the structural unit (a0) is excluded); a structural unit (a2) containing a lactone-containing cyclic group, an —SO$_2$— containing cyclic group or a carbonate-containing cyclic group; a structural unit (a3) containing a polar group-containing aliphatic hydrocarbon group (provided that the structural units (a0), (a1) and (a2) are excluded); a structural unit (a4) containing an acid non-dissociable aliphatic cyclic group; a structural unit (a10) represented by general formula (a10-1); and a structural unit derived from styrene or a derivative thereof.

Structural Unit (a1):

In addition to the structural unit (a0), the component (A1) may include a structural unit (a1) containing an acid decomposable group that exhibits increased polarity by the action of acid (provided that structural units which fall under the definition of the structural unit (a0) is excluded).

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group (—SO$_3$H). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

The "acid dissociable group" refers to both (i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

Examples of the acid dissociable group for the structural unit (a1) include acid dissociable groups which have been proposed for a base resin of a chemically amplified resist composition, provided that groups described above as the tertiary carbon atom-containing group within the aforementioned general formula (a0-1) are excluded. Specific examples of acid dissociable groups for the base resin of a conventional chemically amplified resist include "acetal-type acid dissociable group", "tertiary alkyl ester-type acid dissociable group" and "tertiary alkyloxycarbonyl acid dissociable group" described below.

Acetal-Type Acid Dissociable Group

Examples of the acid dissociable group for protecting the carboxy group or hydroxy group as a polar group include the acid dissociable group represented by general formula (a1-r-1) shown below (hereafter, referred to as "acetal-type acid dissociable group").

[Chemical Formula 8.]

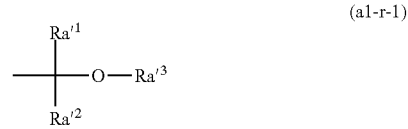

(a1-r-1)

In the formula, Ra$'^1$ and Ra$'^2$ represents a hydrogen atom or an alkyl group; and Ra$'^3$ represents a hydrocarbon group, provided that Ra$'^3$ may be bonded to Ra$'^1$ or Ra$'^2$.

In the formula (a1-r-1), it is preferable that at least one of Ra$'^1$ and Ra$'^2$ represents a hydrogen atom, and it is more preferable that both of Ra$'^1$ and Ra$'^2$ represent a hydrogen atom.

In the case where Ra$'^1$ or Ra$'^2$ is an alkyl group, as the alkyl group, the same alkyl groups as those described above the for the substituent which may be bonded to the carbon atom on the α-position of the aforementioned α-substituted acrylate ester can be mentioned, and an alkyl group having 1 to 5 carbon atoms is preferable. Specific examples include linear or branched alkyl groups. Specific examples of the alkyl group include a methyl group, an ethyl group, a propyl group, an isopropyl group, an n-butyl group, an isobutyl group, a tert-butyl group, a pentyl group, an isopentyl group and a neopentyl group. Of these, a methyl group or an ethyl group is preferable, and a methyl group is particularly preferable.

In formula (a1-r-1), examples of the hydrocarbon group for $Ra'^3$ include a linear or branched alkyl group and a cyclic hydrocarbon group.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5 carbon atoms. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

In the case where $Ra'^3$ represents a cyclic hydrocarbon group, the cyclic hydrocarbon group may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

When the monovalent hydrocarbon group for $Ra'^3$ is an aromatic hydrocarbon group, the aromatic hydrocarbon group is a hydrocarbon group having at least one aromatic ring.

The aromatic ring is not particularly limited, as long as it is a cyclic conjugated compound having $(4n+2)\pi$ electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group for $Ra'^3$ include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

In the case where $Ra'^3$ is bonded to $Ra'^1$ or $Ra'^2$ to form a ring, the cyclic group is preferably a 4 to 7-membered ring, and more preferably a 4 to 6-membered ring. Specific examples of the cyclic group include tetrahydropyranyl group and tetrahydrofuranyl group.

Tertiary Alkyl Ester-Type Acid Dissociable Group

Examples of the acid dissociable group for protecting the carboxy group as a polar group include the acid dissociable group represented by general formula (a1-r-2) shown below. Among the acid dissociable groups represented by general formula (a1-r-2), for convenience, a group which is constituted of alkyl groups is referred to as "tertiary ester-type acid dissociable group".

[Chemical Formula 9.]

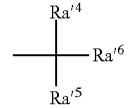

(a1-r-2)

In the formula, $Ra'^4$ to $Ra'^6$ each independently represents a hydrocarbon group, provided that $Ra'^5$ and $Ra'^6$ may be mutually bonded to form a ring.

As the hydrocarbon group for $Ra'^4$ to $Ra'^6$, the same groups as those described above for $Ra'^3$, and a chain alkenyl group may be mentioned. The chain alkenyl group may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group. Among these examples, as the chain-like alkenyl group, a linear alkenyl group is preferable, a vinyl group or a propenyl group is more preferable, and a vinyl group is most preferable.

$Ra'^4$ is preferably a group in which one hydrogen atom has been removed from an aromatic hydrocarbon ring or an aromatic heterocyclic ring (an aryl group or a heteroaryl group), or an alkyl group having 1 to 5 carbon atoms. In the case where $Ra'^5$ and $Ra'^6$ are mutually bonded to form a ring, a group represented by general formula (a1-r2-1) shown below can be mentioned. On the other hand, in the case where $Ra'^4$ to $Ra'^6$ are not mutually bonded and independently represent a hydrocarbon group, the group represented by general formula (a1-r2-2) shown below can be mentioned.

[Chemical Formula 10.]

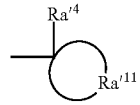

(a1-r-2-1)

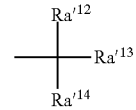

(a1-r-2-2)

In the formulae, $Ra'^{10}$ represents a hydrocarbon group having 1 to 10 carbon atoms; $Ra'^{11}$ is a group which forms an aliphatic cyclic group together with a carbon atom having $Ra'^{10}$ bonded thereto; and $Ra'^{12}$ to $Ra'^{14}$ each independently represents a hydrocarbon group.

In formula (a1-r2-1), the aliphatic cyclic group which is formed by $Ra'^{11}$ together with the carbon atom bonded to $Ra'^{10}$, the same groups as those described above for the monocyclic or polycyclic aliphatic hydrocarbon group for $Ra'^{3}$ in formula (a1-r-1) are preferable. Further, part of the carbon atoms constituting the monocyclic group or the polycyclic group as the aliphatic hydrocarbon group may be substituted with a hetero atom to form a heterocyclic group. Examples of the hetero atom within the heterocyclic group include an oxygen atom, a sulfur atom and a nitrogen atom.

However, the aliphatic cyclic group formed by $Ra'^{11}$ together with the carbon atom bonded to $Ra'^{10}$ excludes the aliphatic cyclic group formed by $Ra^{01}$ bonded to $Ra^{03}$ together with the carbon atom to which $Ra^{03}$ is bonded and the carbon atom to which $Ra^{01}$ is bonded in the aforementioned formula (a0-1). Further, the aliphatic cyclic group formed by $Ra'^{11}$ together with the carbon atom bonded to $Ra'^{10}$ excludes the aliphatic cyclic group formed by $Ra^{01}$ bonded to $Ra^{04}$, together with the carbon atom to which $Ra^{04}$ is bonded, the carbon atom to which $Ra^{03}$ is bonded and the carbon atom to which $Ra^{01}$ is bonded.

In the formula (a1-r2-1), as the hydrocarbon group having 1 to 10 carbon atoms for $Ra'^{10}$, the same groups as described above for the linear or branched alkyl group for $Ra'^{3}$ in the formula (a1-r-1) are preferable.

In the formula (a1-r2-2), it is preferable that $Ra'^{12}$ and $Ra'^{14}$ each independently represents an alkyl group or 1 to 10 carbon atoms, and it is more preferable that the alkyl group is the same group as the described above for the linear or branched alkyl group for $Ra'^{3}$ in the formula (a1-r-1), it is still more preferable that the alkyl group is a linear alkyl group having 1 to 5 carbon atoms, and it is particularly preferable that the alkyl group is a methyl group or an ethyl group.

In the formula (a1-r2-2), it is preferable that $Ra'^{13}$ is the same group as described above for the linear or branched alkyl group or monocyclic or polycyclic alicyclic hydrocarbon group for $Ra'^{3}$ in the formula (a1-r-1). Among these examples, monocyclic or polycyclic aliphatic hydrocarbon group for $Ra'^{3}$ are more preferable. Further, part of the carbon atoms constituting the monocyclic group or the polycyclic group as the aliphatic hydrocarbon group may be substituted with a hetero atom to form a heterocyclic group. Examples of the hetero atom within the heterocyclic group include an oxygen atom, a sulfur atom and a nitrogen atom.

Specific examples of the group represented by the aforementioned formula (a1-r2-1) are shown below. and * represents a valence bond.

[Chemical Formula 11.]

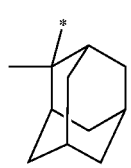
(r-pr-m1)

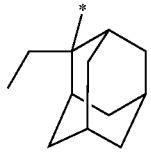
(r-pr-m2)

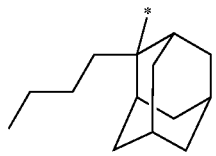
(r-pr-m3)

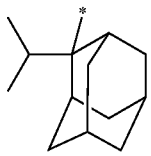
(r-pr-m4)

(r-pr-m5)

(r-pr-m6)

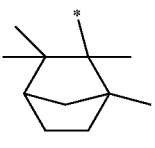
(r-pr-m7)

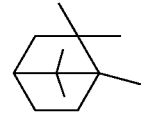
(r-pr-m8)

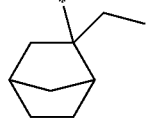
(r-pr-m9)

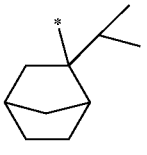
(r-pr-m10)

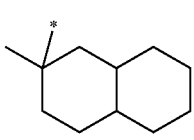
(r-pr-m11)

-continued
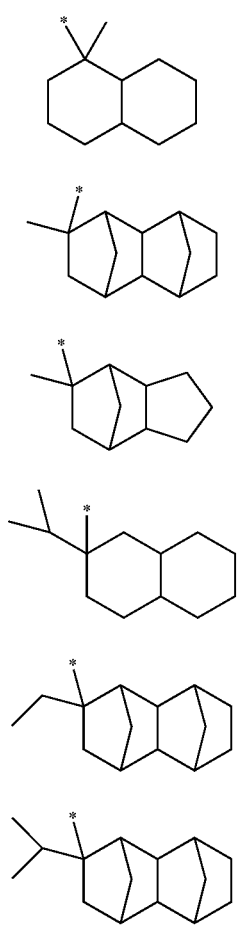
(r-pr-m12)
(r-pr-m13)
(r-pr-m14)
(r-pr-m15)
(r-pr-m16)
(r-pr-m17)
[Chemical Formula 12.]
(r-pr-s1)
(r-pr-s2)
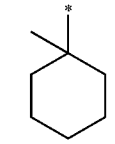
(r-pr-s3)
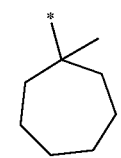
(r-pr-s4)
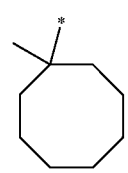
-continued
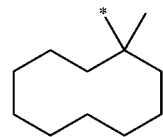
(r-pr-s5)
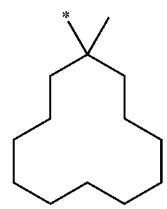
(r-pr-s6)
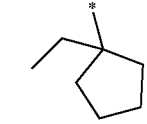
(r-pr-s7)
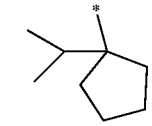
(r-pr-s8)
(r-pr-s9)
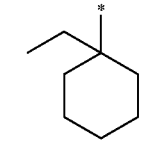
(r-pr-s10)
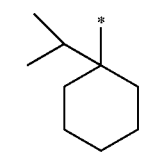
(r-pr-s11)
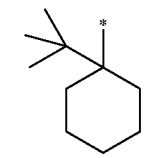
(r-pr-s12)
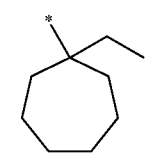
(r-pr-s13)
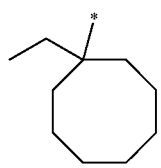
(r-pr-s14)

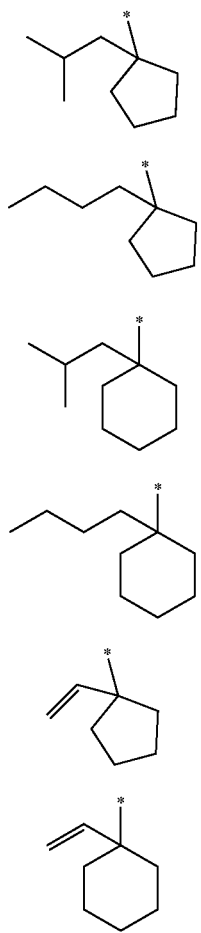
[Chemical Formula 13.]
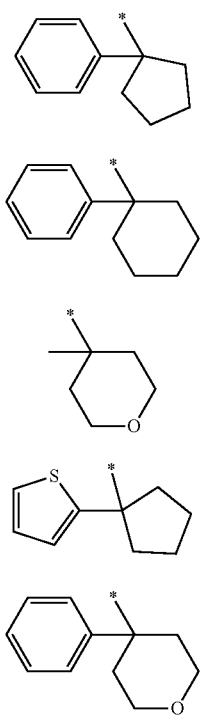
Specific examples of the group represented by the aforementioned formula (a1-r2-2) are shown below.
[Chemical Formula 14.]
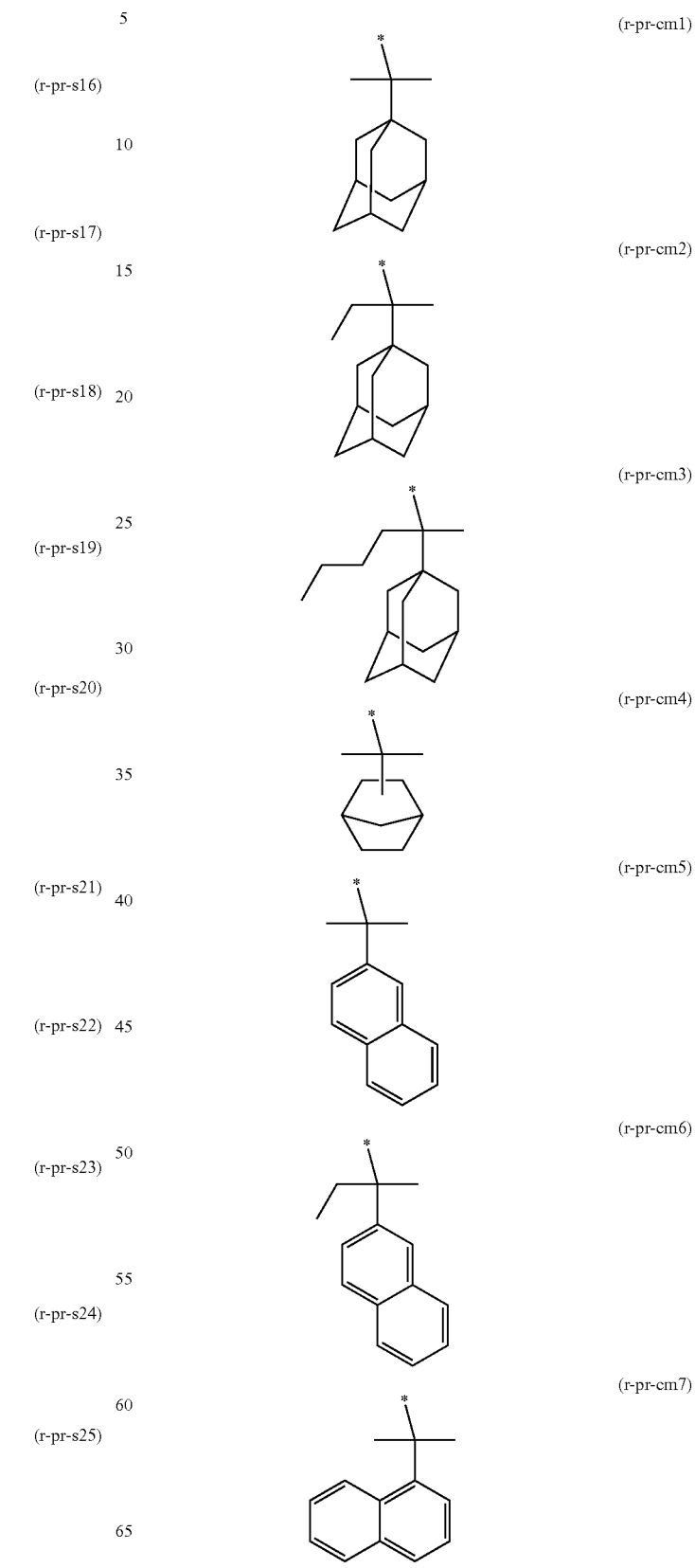

-continued (r-pr-cm8)
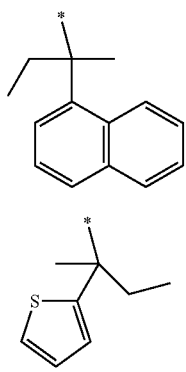

(r-pr-cm9)

[Chemical Formula 15.]

(r-pr-cs1)
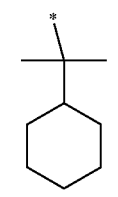

(r-pr-cs2)
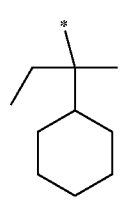

(r-pr-cs3)
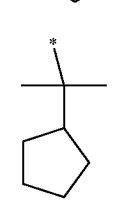

(r-pr-cs4)
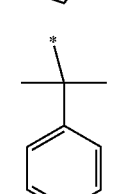

(r-pr-cs5)
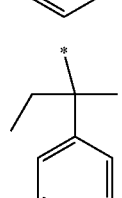

(r-pr-c1)
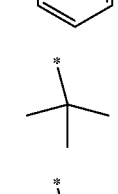

(r-pr-c2)
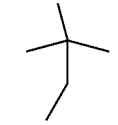

-continued (r-pr-c3)
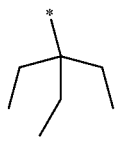

Tertiary Alkyloxycarbonyl Acid Dissociable Group

Examples of the acid dissociable group for protecting a hydroxy group as a polar group include the acid dissociable group represented by general formula (a1-r-3) shown below (hereafter, for convenience, referred to as "tertiary alkyloxycarbonyl-type acid dissociable group").

[Chemical Formula 16.]

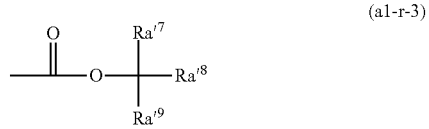 (a1-r-3)

In the formula, $Ra'^7$ to $Ra'^9$ each independently represents an alkyl group.

In formula (a1-r-3), each of $Ra'^7$ to $Ra'^9$ is preferably an alkyl group having 1 to 5 carbon atoms, and more preferably an alkyl group having 1 to 3 carbon atoms. Further, the total number of carbon atoms in the alkyl groups is preferably 3 to 7, more preferably 3 to 5, and still more preferably 3 or 4.

Examples of the structural unit (a1) include a structural unit derived from an acrylate ester which may have the hydrogen atom bonded to the carbon atom on the α-position substituted with a substituent; a structural unit derived from an acrylamide; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

Specific examples of preferable structural units for the structural unit (a1) include structural units represented by general formula (a1-1) or (a1-2) shown below.

[Chemical Formula 17.]

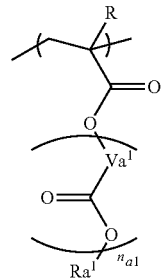 (a1-1)

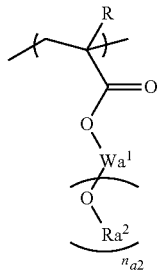

(a1-2)

In the formula, R represents a hydrogen atom, an alkyl group having 1 to 5 carbon atoms or a halogenated alkyl group having 1 to 5 carbon atoms; $Va^1$ represents a divalent hydrocarbon group which may contain an ether bond; $n_{a1}$ represents an integer of 0 to 2; and $Ra^1$ represents an acid dissociable group represented by the aforementioned formula (a1-r-1) or (a1-r-2). $Wa^1$ represents a hydrocarbon group having a valency of $n_{a2}+1$; $n_{a2}$ represents an integer of 1 to 3; and $Ra^2$ represents an acid dissociable group represented by the aforementioned formula (a1-r-1) or (a1-r-3).

In the aforementioned formula (a1-1), as the alkyl group having 1 to 5 carbon atoms for R, a linear or branched alkyl group having 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group having 1 to 5 carbon atoms represented by R is a group in which part or all of the hydrogen atoms of the aforementioned alkyl group having 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group having 1 to 5 carbon atoms or a fluorinated alkyl group having 1 to 5 carbon atoms is preferable, and a hydrogen atom or a methyl group is particularly desirable in terms of industrial availability.

In formula (a1-1), $Va^1$ represents a divalent hydrocarbon group which may have an ether bond. The divalent hydrocarbon group for $Va^1$ may be an aliphatic hydrocarbon group or an aromatic hydrocarbon group.

The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group preferably has 2 to 10 carbon atoms, more preferably 3 to 6 carbon atoms, still more preferably 3 or 4 carbon atoms, and most preferably 3 carbon atoms.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group having 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. The linear or branched aliphatic hydrocarbon group is the same as defined for the aforementioned linear aliphatic hydrocarbon group or the aforementioned branched aliphatic hydrocarbon group.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group as the divalent hydrocarbon group for $Va^1$ is a hydrocarbon group having an aromatic ring.

The aromatic hydrocarbon group preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

In the aforementioned formula (a1-2), the hydrocarbon group for $Wa^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof.

The valency of $n_{a2}+1$ is preferably divalent, trivalent or tetravalent, and divalent or trivalent is more preferable.

Specific examples of structural unit represented by formula (a1-1) are shown below.

In the formulae shown below, $R^1$ represents a hydrogen atom, a methyl group or a trifluoromethyl group.

[Chemical Formula 18.]

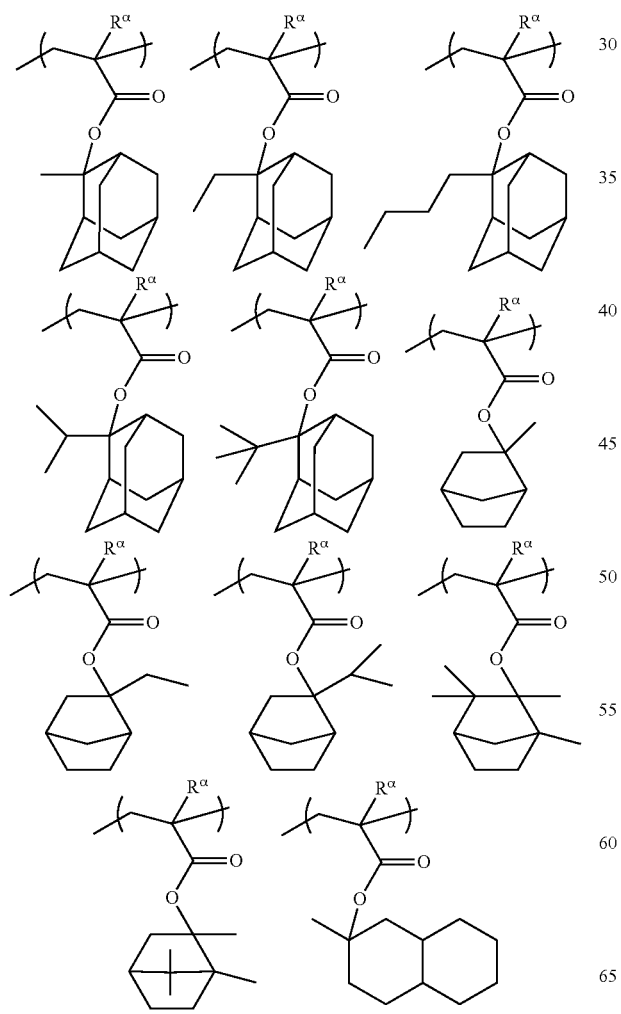

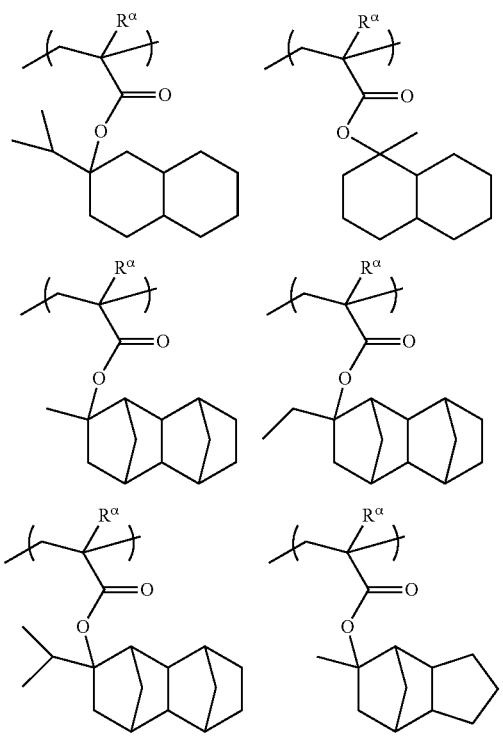

[Chemical Formula 19.]

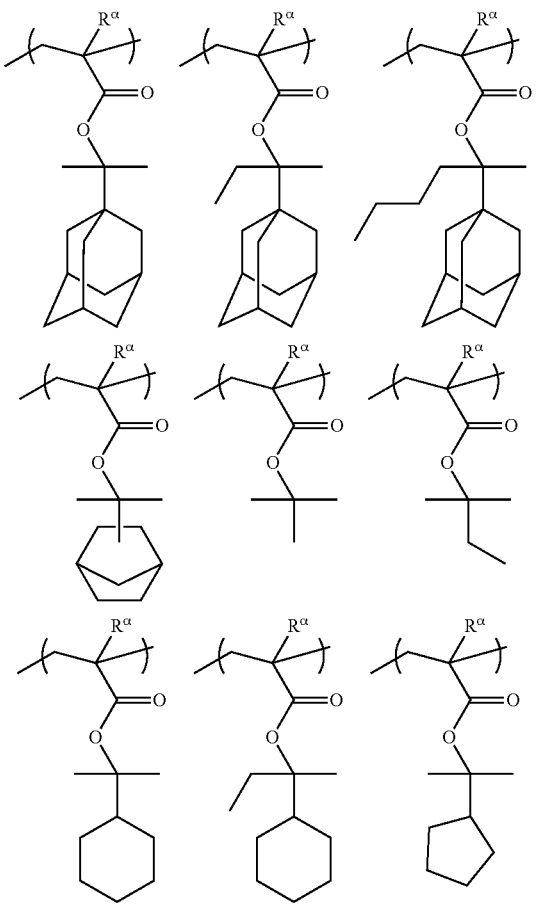

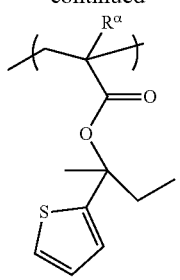
[Chemical Formula 20.]
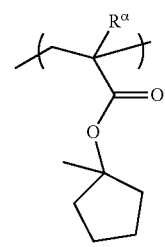 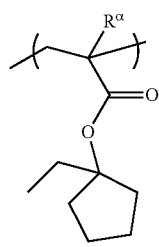 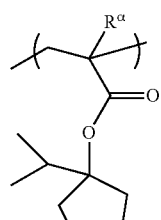
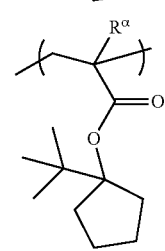 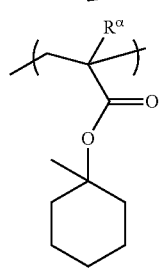 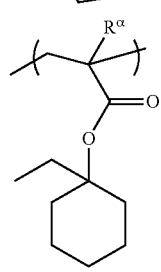
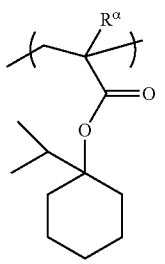 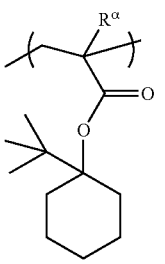 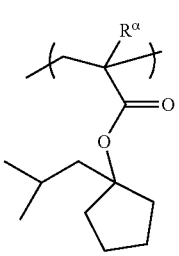
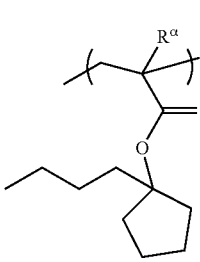 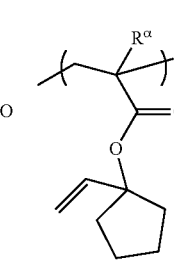 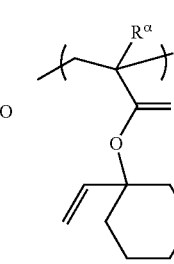
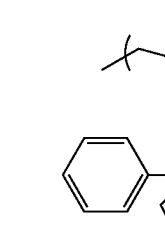 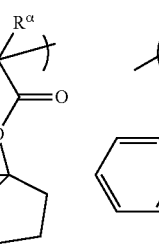
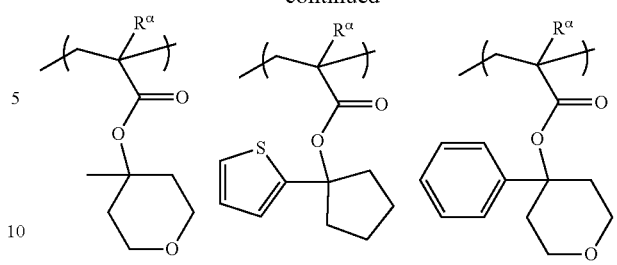
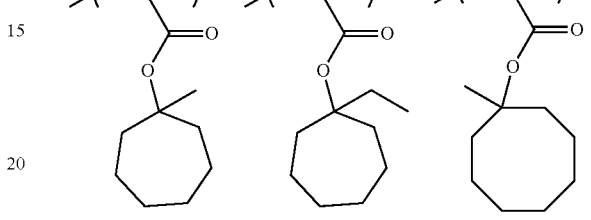
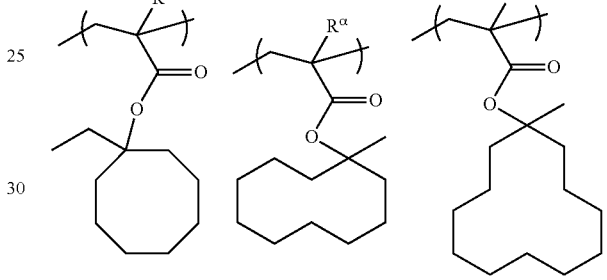
[Chemical Formula 21.]
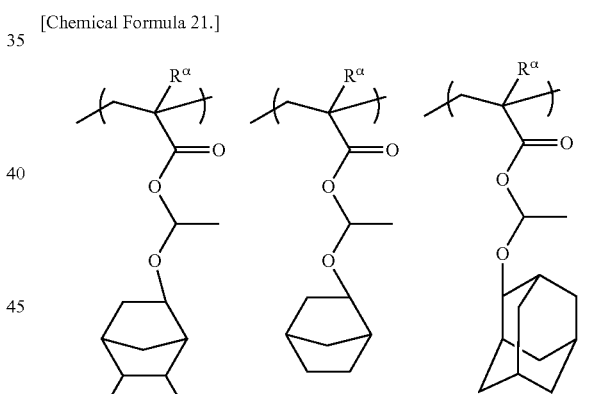
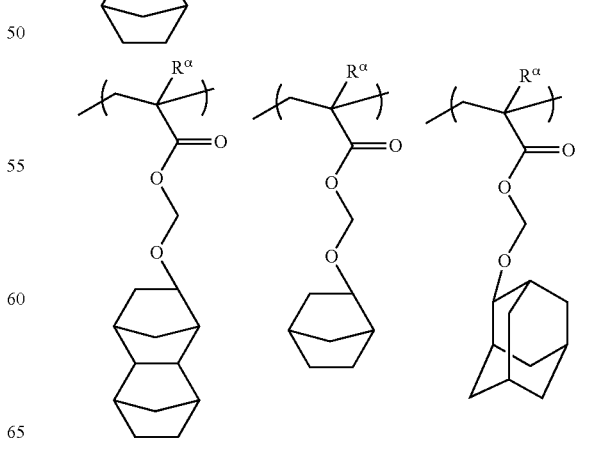

-continued
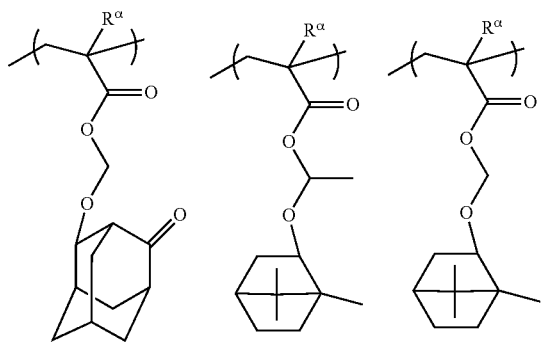
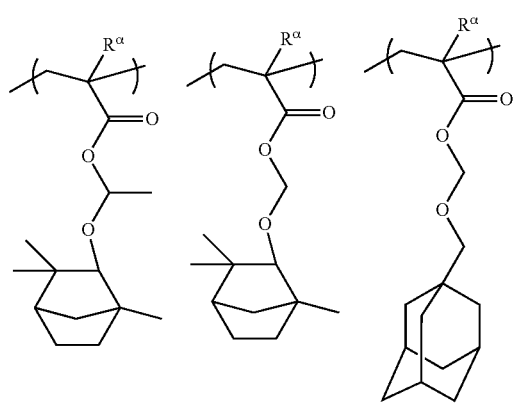
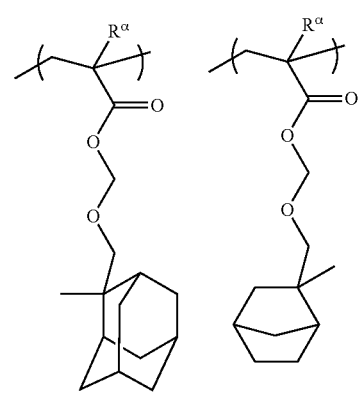
[Chemical Formula 22.]
-continued
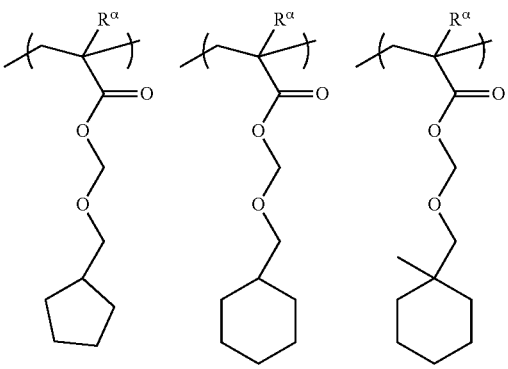
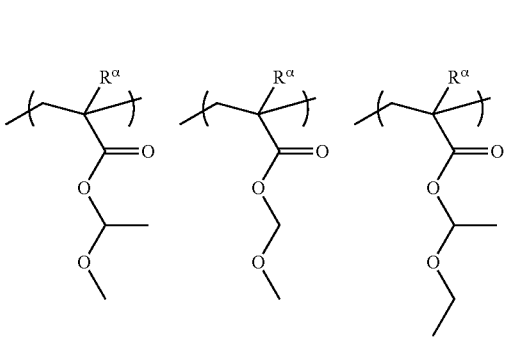
[Chemical Formula 23.]
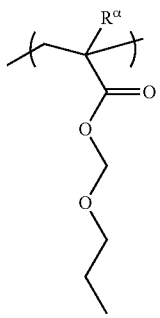

-continued
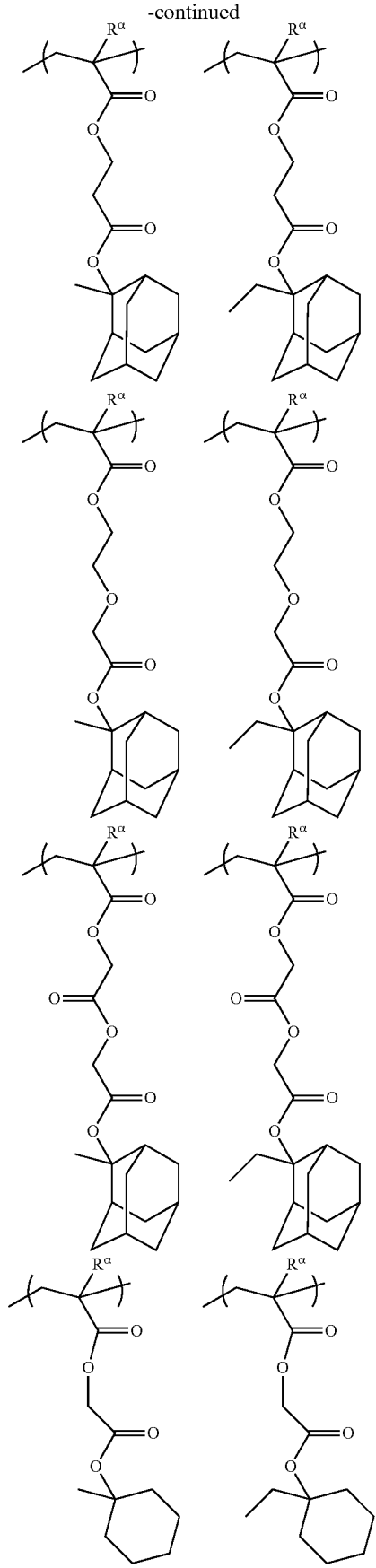
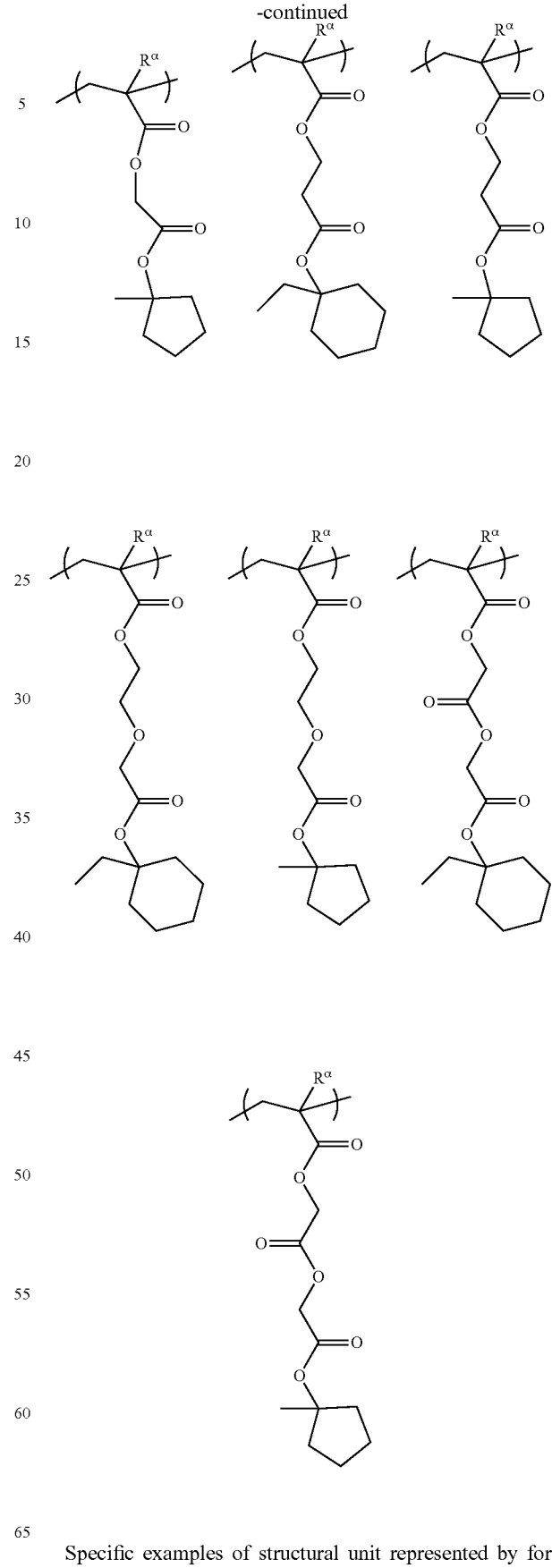
Specific examples of structural unit represented by formula (a1-2) are shown below.

[Chemical Formula 24.]

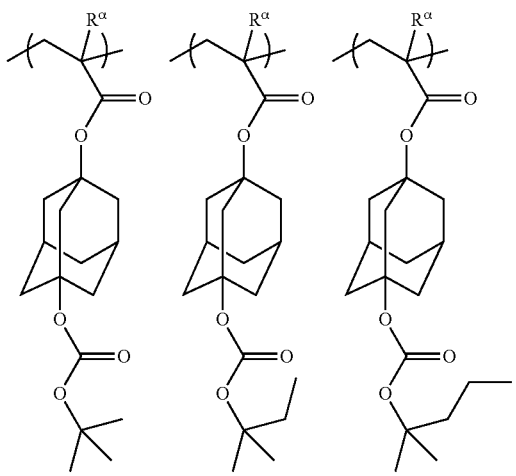

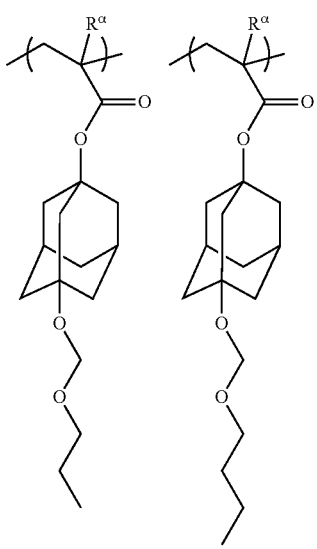

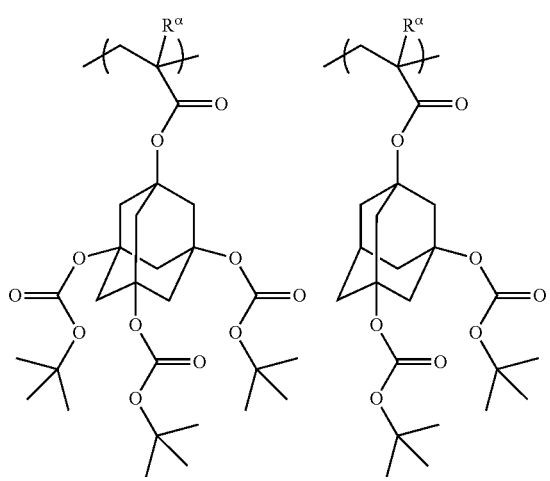

-continued

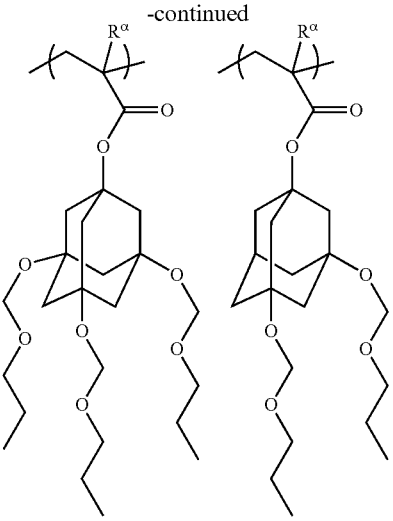

As the structural unit (a1) contained in the component (A1), 1 type of structural unit may be used, or 2 or more types may be used.

When the component (A1) includes the structural unit (a1), the amount of the structural unit (a1) within the component (A1), based on the combined total of all structural units constituting the component (A1) (100 mol %) is preferably 1 to 50 mol %, more preferably 5 to 45 mol %, and still more preferably 5 to 30 mol %.

When the amount of the structural unit (a1) is at least as large as the lower limit of the above-mentioned range, a resist pattern can be reliably obtained, and various lithography properties such as sensitivity, resolution and roughness are further reduced. On the other hand, when the amount of the structural unit (a1) is no more than the upper limit of the above-mentioned range, a good balance can be achieved with the other structural units.

Structural Unit (a2):

The component (A1) may include, in addition to the structural unit (a0), a structural unit (a2) containing a lactone-containing cyclic group, an —$SO_2$— containing cyclic group or a carbonate-containing cyclic group.

When the component (A1) is used for forming a resist film, the lactone-containing cyclic group, the —$SO_2$— containing cyclic group or the carbonate-containing cyclic group within the structural unit (a2) is effective in improving the adhesion between the resist film and the substrate. Further, by virtue of including the structural unit (a2), in an alkali developing process, during developing, the solubility of the resist film in an alkali developing is enhanced.

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2) is not particularly limited, and an arbitrary structural unit may be used. Specific examples include groups represented by general formulae (a2-r-1) to (a2-r-7) shown below.

[Chemical Formula 25.]

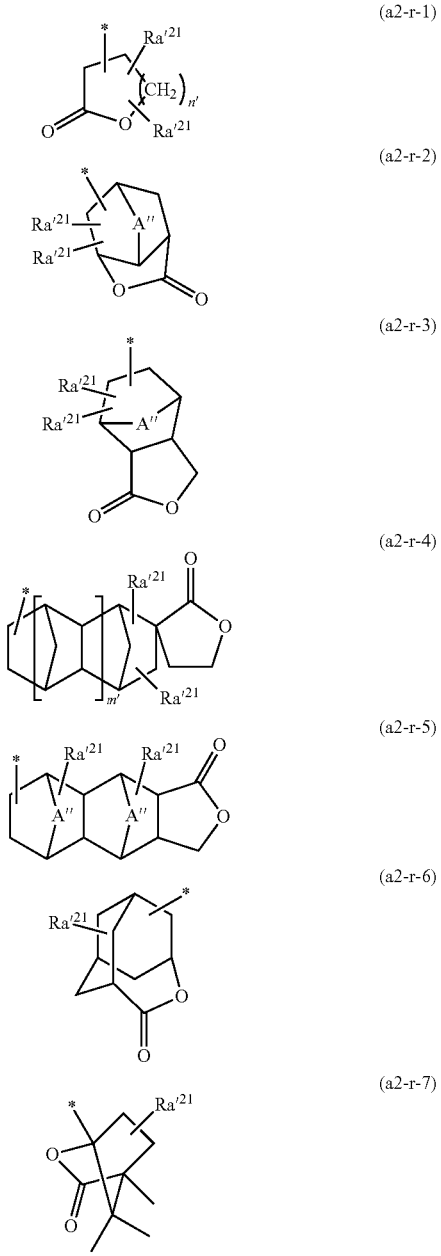

(a2-r-1)
(a2-r-2)
(a2-r-3)
(a2-r-4)
(a2-r-5)
(a2-r-6)
(a2-r-7)

In the formulae, each $Ra'^{21}$ independently represents a hydrogen atom, an alkyl group, an alkoxy group, a halogen atom, a halogenated alkyl group, a hydroxy group, —COOR", —OC(═O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom, or an alkylene group having 1 to 5 carbon atoms which may contain an oxygen atom or a sulfur atom; n' represents an integer of 0 to 2; and m' represents 0 or 1.

In formulae (a2-r-1) to (a2-r-7), the alkyl group for $Ra'^{21}$ is preferably an alkyl group having 1 to 6 carbon atoms. The alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is most preferable.

The alkoxy group for $Ra'^{21}$ is preferably an alkoxy group having 1 to 6 carbon atoms.

The alkoxy group is preferably a linear or branched alkoxy group. Specific examples of the alkoxy groups include the aforementioned alkyl groups for $Ra'^{21}$ having an oxygen atom (—O—) bonded thereto.

As examples of the halogen atom for $Ra'^{21}$, a fluorine atom, chlorine atom, bromine atom and iodine atom can be given. Among these, a fluorine atom is preferable.

Examples of the halogenated alkyl group for $Ra'^{21}$ include groups in which part or all of the hydrogen atoms within the aforementioned alkyl group for $Ra'^{21}$ has been substituted with the aforementioned halogen atoms. As the halogenated alkyl group, a fluorinated alkyl group is preferable, and a perfluoroalkyl group is particularly desirable.

With respect to —COOR" and —OC(═O)R" for $Ra'^{21}$, R" represents a hydrogen atom, an alkyl group, a lactone-containing cyclic group, a carbonate-containing cyclic group or an —SO$_2$— containing cyclic group.

The alkyl group for R" may be linear, branched or cyclic, and preferably has 1 to 15 carbon atoms.

When R" represents a linear or branched alkyl group, it is preferably an alkyl group having 1 to 10 carbon atoms, more preferably an alkyl group having 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and still more preferably 5 to 10 carbon atoms. Specific examples include groups in which one or more hydrogen atoms have been removed from a monocycloalkane or a polycycloalkane such as a bicycloalkane, tricycloalkane or tetracycloalkane which may or may not be substituted with a fluorine atom or a fluorinated alkyl group. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

Examples of the lactone-containing cyclic group for R" include groups represented by the aforementioned general formulae (a2-r-1) to (a2-r-7). The carbonate-containing cyclic group for R" is the same as defined for the carbonate-containing cyclic group described later. Specific examples of the carbonate-containing cyclic group include groups represented by general formulae (ax3-r-1) to (ax3-r-3).

The —SO$_2$— containing cyclic group for R" is the same as defined for the —SO$_2$-containing cyclic group described later. Specific examples of the —SO$_2$— containing cyclic group include groups represented by general formulae (a5-r-1) to (a5-r-4).

The hydroxyalkyl group for $Ra'^{21}$ preferably has 1 to 6 carbon atoms, and specific examples thereof include the alkyl groups for $Ra'^{21}$ in which at least one hydrogen atom has been substituted with a hydroxy group.

In formulae (a2-r-2), (a2-r-3) and (a2-r-5), as the alkylene group having 1 to 5 carbon atoms represented by A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—$CH_2$—, —$CH_2$—O—$CH_2$—, —S—$CH_2$—, and —$CH_2$—S—$CH_2$—. As A'', an alkylene group having 1 to 5 carbon atoms or —O— is preferable, more preferably an alkylene group having 1 to 5 carbon atoms, and most preferably a methylene group.

Specific examples of the groups represented by the aforementioned general formulae (a2-r-1) to (a2-r-7) are shown below.

[Chemical Formula 26.]

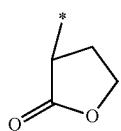 (r-lc-1-1)

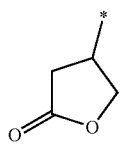 (r-lc-1-2)

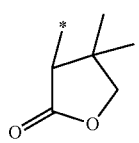 (r-lc-1-3)

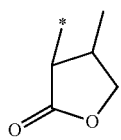 (r-lc-1-4)

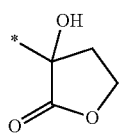 (r-lc-1-5)

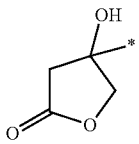 (r-lc-1-6)

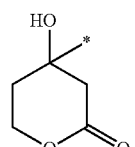 (r-lc-1-7)

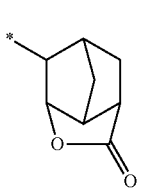 (r-lc-2-1)

-continued

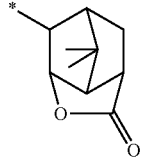 (r-lc-2-2)

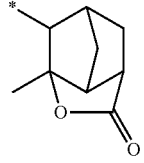 (r-lc-2-3)

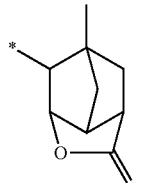 (r-lc-2-4)

 (r-lc-2-5)

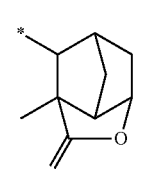 (r-lc-2-6)

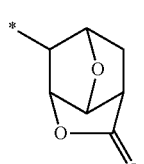 (r-lc-2-7)

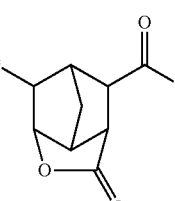 (r-lc-2-8)

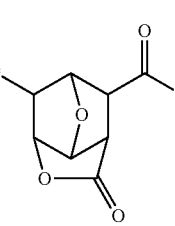 (r-lc-2-9)

-continued
(r-lc-2-10)
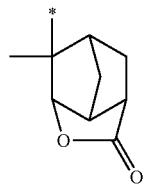
(r-lc-2-11)
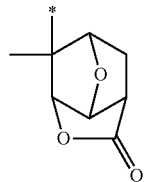
(r-lc-2-12)
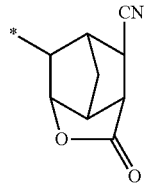
(r-lc-2-13)
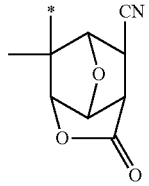
(r-lc-2-14)
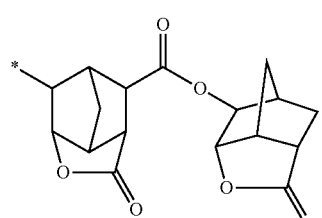
(r-lc-2-15)
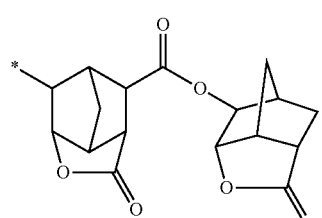
(r-lc-2-16)
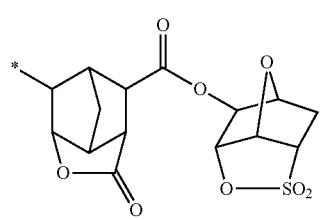
-continued
(r-lc-2-17)
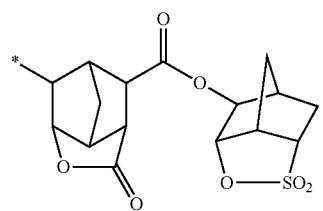
(r-lc-2-18)
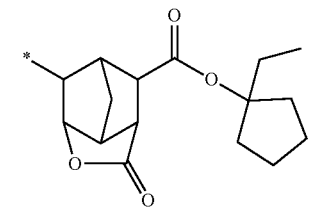
(r-lc-3-1)
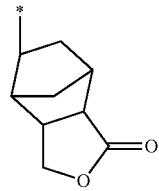
(r-lc-3-2)
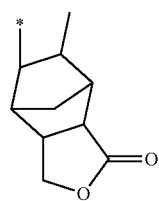
(r-lc-3-3)
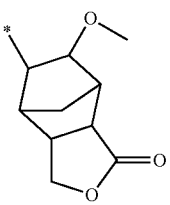
(r-lc-3-4)
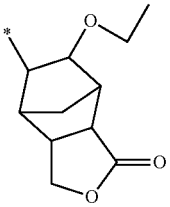
(r-lc-3-5)
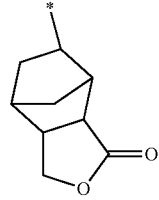

[Chemical Formula 27.]

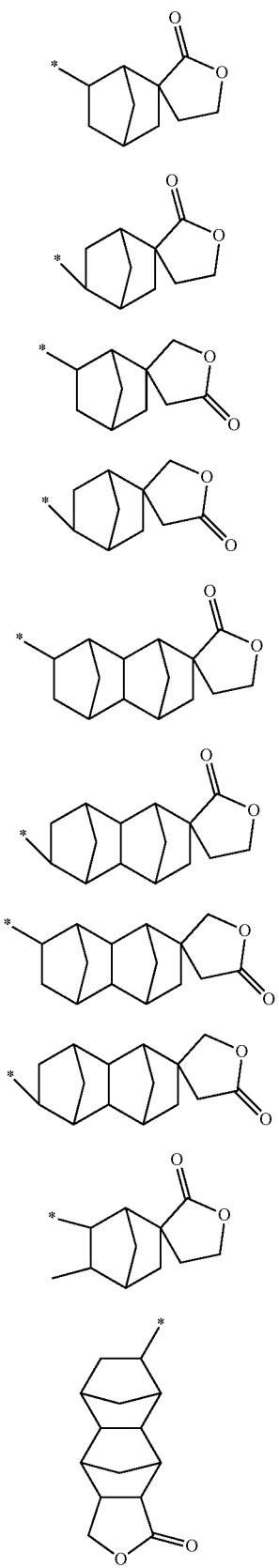

(r-lc-4-1)
(r-lc-4-2)
(r-lc-4-3)
(r-lc-4-4)
(r-lc-4-5)
(r-lc-4-6)
(r-lc-4-7)
(r-lc-4-8)
(r-lc-4-9)
(r-lc-5-1)

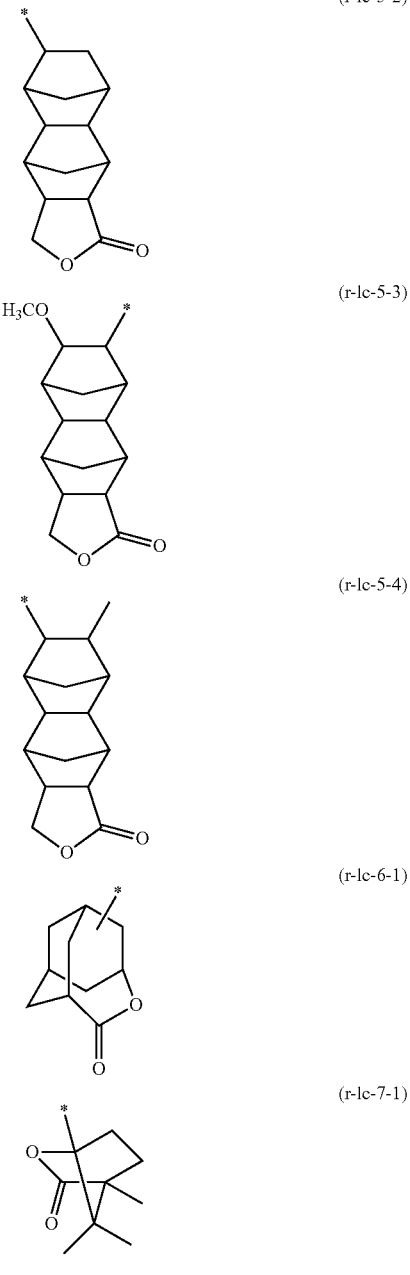

(r-lc-5-2)
(r-lc-5-3)
(r-lc-5-4)
(r-lc-6-1)
(r-lc-7-1)

An "—SO$_2$— containing cyclic group" refers to a cyclic group having a ring containing —SO$_2$— within the ring structure thereof, i.e., a cyclic group in which the sulfur atom (S) within —SO$_2$— forms part of the ring skeleton of the cyclic group. The ring containing —SO$_2$— within the ring skeleton thereof is counted as the first ring. A cyclic group in which the only ring structure is the ring that contains —SO$_2$— in the ring skeleton thereof is referred to as a monocyclic group, and a group containing other ring structures is described as a polycyclic group regardless of the structure of the other rings. The —SO$_2$— containing cyclic group may be either a monocyclic group or a polycyclic group.

As the —SO$_2$— containing cyclic group, a cyclic group containing —O—SO$_2$-within the ring skeleton thereof, i.e., a cyclic group containing a sultone ring in which —O—S— within the —O—SO$_2$— group forms part of the ring skeleton thereof is particularly desirable.

More specific examples of the —SO$_2$— containing cyclic group include groups represented by general formulas (a5-r-1) to (a5-r-4) shown below.

[Chemical Formula 28.]

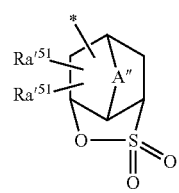
(a5-r-1)

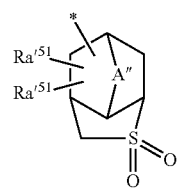
(a5-r-2)

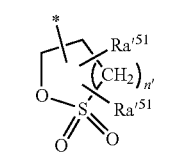
(a5-r-3)

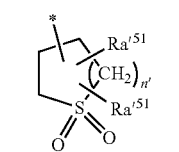
(a5-r-4)

In the formulae, each Ra$'^{51}$ independently represents an alkyl group, an alkoxy group, a halogen atom, a halogenated alkyl group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom, or an alkylene group having 1 to 5 carbon atoms with or without an oxygen atom or a sulfur atom;

and n' represents an integer of 0 to 2.

In general formulae (a5-r-1) and (a5-r-2), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for Ra$'^{51}$ include the same groups as those described above in the explanation of Ra$'^{21}$ in the general formulas (a2-r-1) to (a2-r-7).

Specific examples of the groups represented by the aforementioned general formulae (a5-r-1) to (a5-r-4) are shown below. In the formulae shown below, "Ac" represents an acetyl group.

[Chemical Formula 29.]

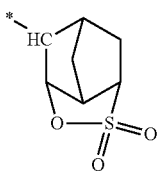
(r-sl-1-1)

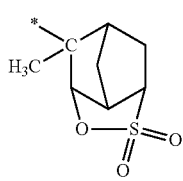
(r-sl-1-2)

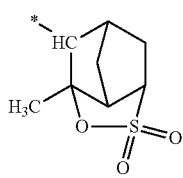
(r-sl-1-3)

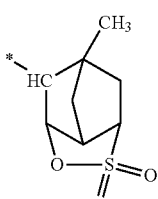
(r-sl-1-4)

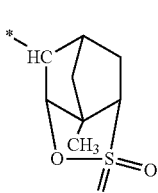
(r-sl-1-5)

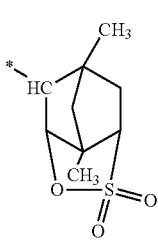
(r-sl-1-6)

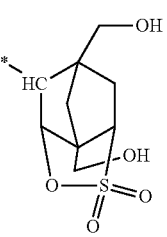
(r-sl-1-7)

-continued
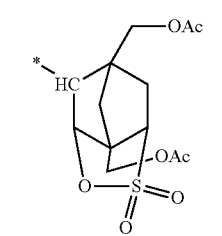
(r-sl-1-8)
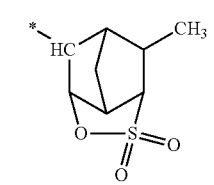
(r-sl-1-9)
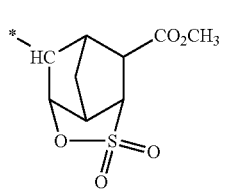
(r-sl-1-10)
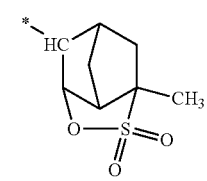
(r-sl-1-11)
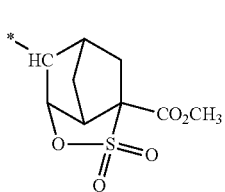
(r-sl-1-12)
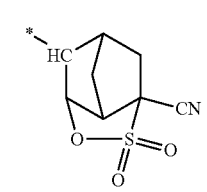
(r-sl-1-13)
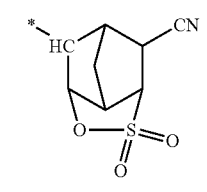
(r-sl-1-14)
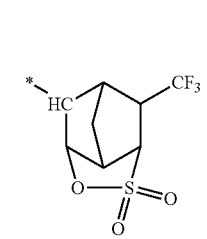
(r-sl-1-15)
-continued
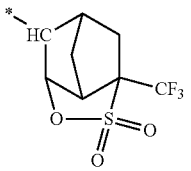
(r-sl-1-16)
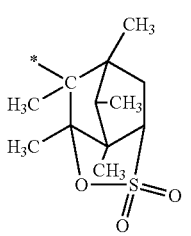
(r-sl-1-17)
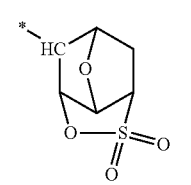
(r-sl-1-18)
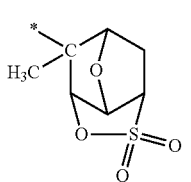
(r-sl-1-19)
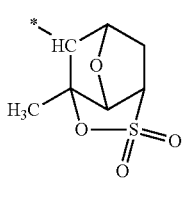
(r-sl-1-20)
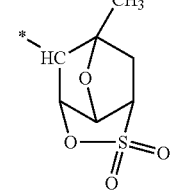
(r-sl-1-21)
[Chemical Formula 30.]
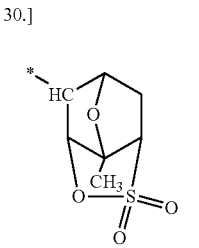
(r-sl-1-22)
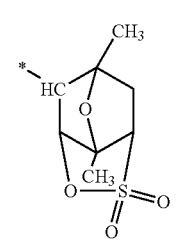
(r-sl-1-23)

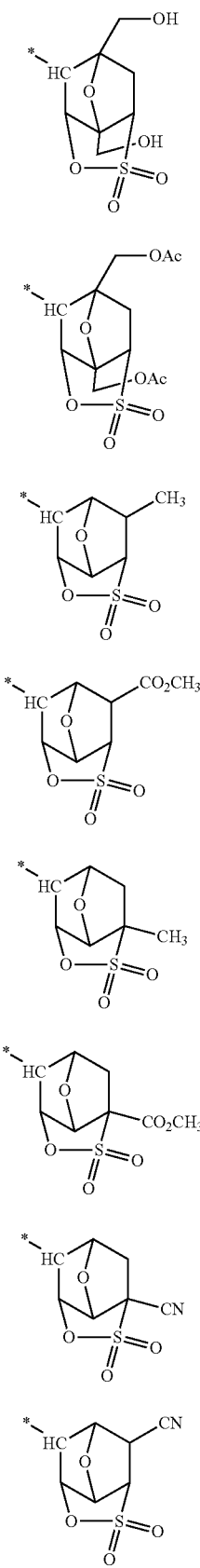
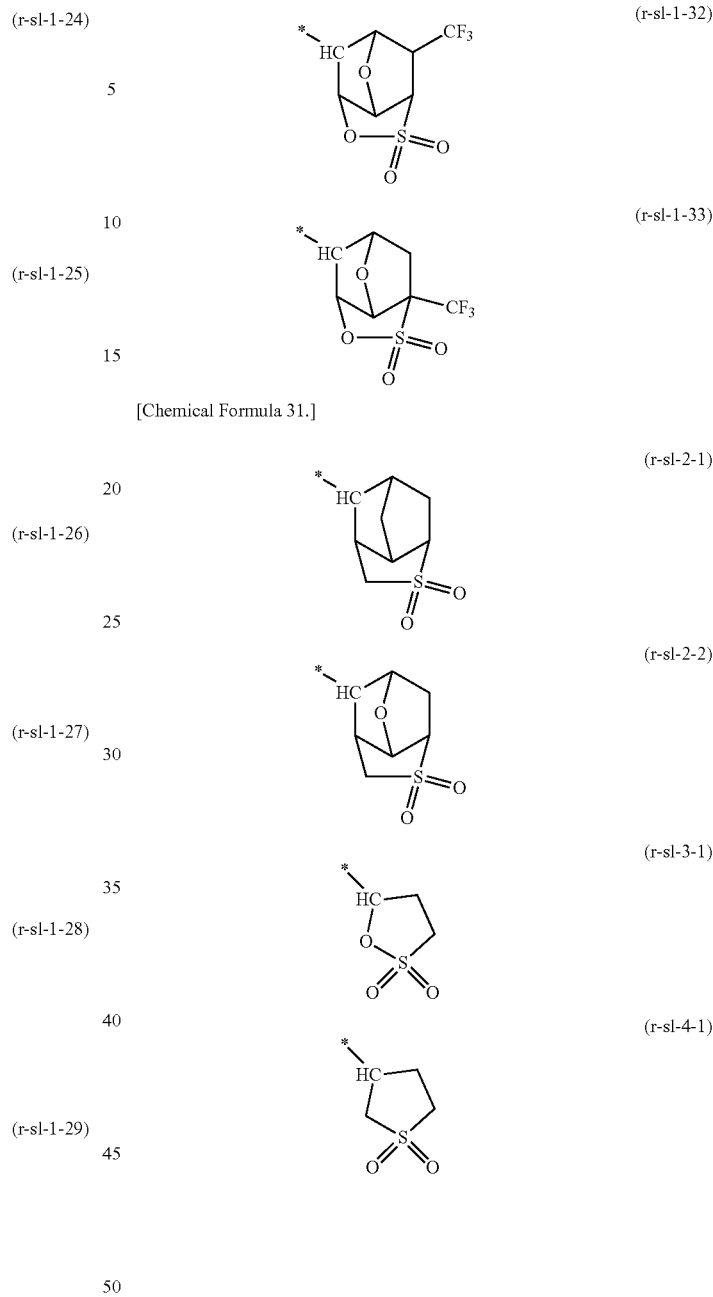

[Chemical Formula 31.]

The term "carbonate-containing cyclic group" refers to a cyclic group including a ring containing a —O—C(=O)—O— structure (carbonate ring). The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group is not particularly limited, and an arbitrary group may be used. Specific examples include groups represented by general formulae (ax3-r-1) to (ax3-r-3) shown below.

[Chemical Formula 32.]

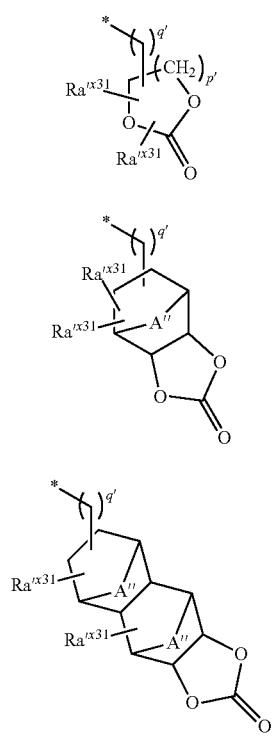

(ax3-r-1)

(ax3-r-2)

(ax3-r-3)

In the formulae, each $Ra'^{x31}$ independently represents an alkyl group, an alkoxy group, a halogen atom, a halogenated alkyl group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom, or an alkylene group having 1 to 5 carbon atoms with or without an oxygen atom or a sulfur atom; p' represents an integer of 0 to 3; and q' is 0 or 1.

In general formulae (ax3-r-2) and (ax3-r-3), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for $Ra'^{31}$ include the same groups as those described above in the explanation of $Ra'^{21}$ in the general formulas (a2-r-1) to (a2-r-7).

Specific examples of the groups represented by the aforementioned general formulae (ax3-r-1) to (ax3-r-3) are shown below.

[Chemical Formula 33.]

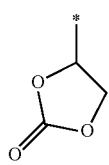

(r-cr-1-1)

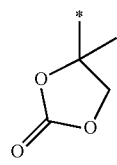

(r-cr-1-2)

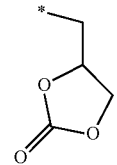

(r-cr-1-3)

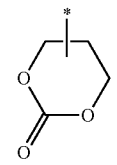

(r-cr-1-4)

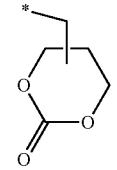

(r-cr-1-5)

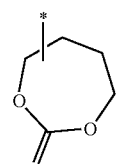

(r-cr-1-6)

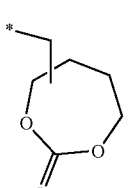

(r-cr-1-7)

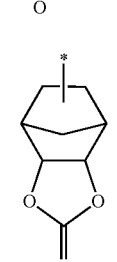

(r-cr-2-1)

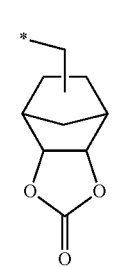

(r-cr-2-2)

(r-cr-2-3)
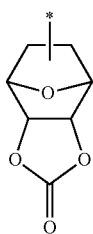

(r-cr-2-4)
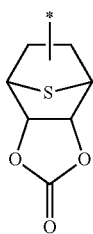

(r-cr-3-1)

(r-cr-3-2)
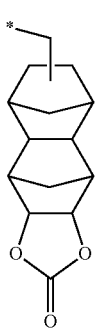

(r-cr-3-3)

(r-cr-3-4)
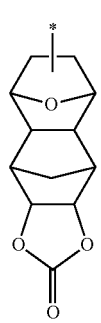

(r-cr-3-5)
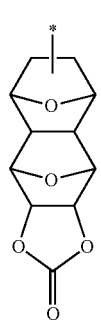

As the structural unit (a2), a structural unit derived from an acrylate ester which may have the hydrogen atom bonded to the carbon atom on the α-position substituted with a substituent is preferable.

Specific examples of preferable structural units for the structural unit (a2) include structural units represented by general formula (a2-1) shown below.

[Chemical Formula 34.]

(a2-1)
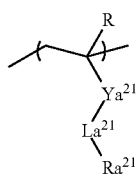

In the formula, R represents a hydrogen atom, an alkyl group having 1 to 5 carbon atoms or a halogenated alkyl group having 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represent —CO—; and $Ra^{21}$ represents a lactone-containing cyclic group, an —SO$_2$— containing cyclic group or a carbonate-containing cyclic group.

In the formula (a2-1), R is the same as defined above.

As R, a hydrogen atom, an alkyl group having 1 to 5 carbon atoms or a fluorinated alkyl group having 1 to 5 carbon atoms is preferable, and a hydrogen atom or a methyl group is particularly desirable in terms of industrial availability.

In the formula (a2-1), the divalent linking group for $Ya^{21}$ is not particularly limited, and preferable examples thereof include a divalent hydrocarbon group which may have a substituent and a divalent linking group containing a hetero atom.

The divalent hydrocarbon group for $Ya^{21}$ is the same as defined for the divalent hydrocarbon group represented by $Va^1$ in the aforementioned formula (a1-1). Examples of the substituent for the divalent hydrocarbon group represented by $Ya^{21}$ include an alkyl group having 1 to 5 carbon atoms, an alkoxy group, a halogen atom, a halogenated alkyl group, a hydroxy group, a carbonyl group.

In the case where $Ya^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (may be substituted with a substituent such as an alkyl group, an acyl group or the like), —S—, —S(=O)$_2$—, —S(=O)$_2$—O—, and a group represented by general formula: —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m'}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represents a divalent hydrocarbon group which may have a substituent, O represents an oxygen atom, and m' represents an integer of 0 to 3].

In the case where the divalent linking group containing a hetero atom is —C(=O)—NH—, —C(=O)—NH—C(=O)—, —NH— or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In general formulae —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m'}$—Y$^{22}$—, —Y$^{21}$—O—C(=O)—Y$^{22}$— or —Y$^{21}$—S(=O)$_2$—O—Y$^{22}$—, Y$^{21}$ and Y$^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As Y$^{21}$, a linear aliphatic hydrocarbon group is preferable, more preferably a linear alkylene group, still more preferably a linear alkylene group having 1 to 5 carbon atoms, and a methylene group or an ethylene group is particularly desirable.

As Y$^{22}$, a linear or branched aliphatic hydrocarbon group is preferable, and a methylene group, an ethylene group or an alkylmethylene group is more preferable. The alkyl group within the alkylmethylene group is preferably a linear alkyl group having 1 to 5 carbon atoms, more preferably a linear alkyl group having 1 to 3 carbon atoms, and most preferably a methyl group.

In the group represented by the formula —[Y$^{21}$—C(=O)—O]$_{m''}$-Y$^{22}$—, m" represents an integer of 0 to 3, preferably an integer of 0 to 2, more preferably 0 or 1, and most preferably 1. Namely, it is particularly desirable that the group represented by the formula —[Y$^{21}$—C(=O)—O]$_{m''}$-Y$^{22}$— is a group represented by the formula —Y$^{21}$—C(=O)—O—Y$^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

$Ya^{21}$ preferably represents an ester bond [—C(=O)—O—], an ether bond (—O—), a linear or branched alkylene group, a combination of these, or a single bond.

In formula (a2-1), $La^{21}$ represents —O—, —COO—, —CON(R')—, —OCO—, —CONHCO— or —CONHCS—.

R' represents a hydrogen atom or a methyl group.

However, when $La^{21}$ represents —O—, $Ya^{21}$ does not represent —CO—.

In the formula (a2-1), $Ra^{21}$ represents a lactone-containing cyclic group, an —SO$_2$— containing cyclic group or a carbonate-containing cyclic group.

Preferable examples of the lactone-containing cyclic group, the —SO$_2$— containing cyclic group and the carbonate-containing cyclic group for $Ra^{21}$ include groups represented by general formulae (a2-r-1) to (a2-r-7), groups represented by general formulae (a5-r-1) to (a5-r-4) and groups represented by general formulae (ax3-r-1) to (ax3-r-3). Among the above examples, as $Ra^{21}$, a lactone-containing cyclic group or an —SO$_2$— containing cyclic group is preferable, and a group represented by the aforementioned general formula (a2-r-1), (a2-r-2), (a2-r-6) or (a5-r-1) is more preferable. Specifically, a group represented by any of chemical formulae (r-1c-1-1) to (r-1c-1-7), (r-1c-2-1) to (r-1c-2-18), (r-1c-6-1), (r-s1-1-1) and (r-s1-1-18) is still more preferable.

As the structural unit (a2) contained in the component (A1), 1 kind of structural unit may be used, or 2 or more kinds may be used.

When the component (A1) contains the structural unit (a2), the amount of the structural unit (a2) based on the combined total (100 mol %) of all structural units constituting the component (A1) is preferably 1 to 80 mol %, more preferably 3 to 70 mol %, still more preferably 5 to 60 mol %, and most preferably 10 to 50 mol %.

When the amount of the structural unit (a2) is at least as large as the lower limit of the above preferable range, the effect of using the structural unit (a2) may be satisfactorily achieved. On the other hand, when the amount of the structural unit (a2) is no more than the upper limit of the above preferable range, a good balance can be achieved with the other structural units, and various lithography properties and pattern shape may be improved.

Structural Unit (a3):

The component (A1) may include, in addition to the structural unit (a0), a structural unit (a3) containing a polar group-containing aliphatic hydrocarbon group (provided that the structural units that fall under the definition of structural units (a0), (a1) and (a2) are excluded).

When the component (A1) includes the structural unit (a3), the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group having 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group having 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 35.]

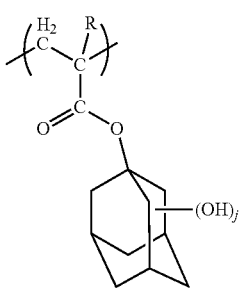

(a3-1)

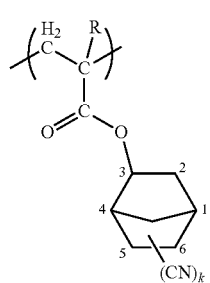

(a3-2)

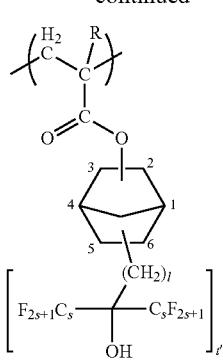

(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 kind of structural unit may be used, or 2 or more kinds of structural units may be used.

When the component (A1) contains the structural unit (a3), the amount of the structural unit (a3) based on the combined total (100 mol %) of all structural units constituting the component (A1) is preferably 1 to 50 mol %, more preferably 3 to 40 mol %, still more preferably 5 to 30 mol %, and most preferably 10 to 30 mol %. When the amount of the structural unit (a3) is at least as large as the lower limit of the above-mentioned preferable range, the resolution is improved in the formation of a resist pattern. On the other hand, when the amount of the structural unit (a3) is no more than the upper limit of the above-mentioned preferable range, a good balance can be reliably achieved with the other structural units.

Structural Unit (a4):

The component (A1) may be further include, in addition to the structural unit (a0), a structural unit (a4) containing an acid non-dissociable, aliphatic cyclic group.

When the component (A1) includes the structural unit (a4), dry etching resistance of the resist pattern to be formed is improved. Further, the hydrophobicity of the component (A) is further improved. Increase in the hydrophobicity contributes to improvement in terms of resolution, shape of the resist pattern and the like, particularly in a solvent developing process.

An "acid non-dissociable, aliphatic cyclic group" in the structural unit (a4) refers to a cyclic group which is not dissociated by the action of the acid (e.g., acid generated from a structural unit which generates acid upon exposure or acid generated from the component (B)) upon exposure, and remains in the structural unit.

As the structural unit (a4), a structural unit which contains a non-acid-dissociable aliphatic cyclic group, and is also derived from an acrylate ester is preferable. As the cyclic group, any of the multitude of conventional polycyclic groups used within the resin component of resist compositions for ArF excimer lasers or KrF excimer lasers (and particularly for ArF excimer lasers) can be used.

As the aliphatic polycyclic group, at least one polycyclic group selected from amongst a tricyclodecyl group, adamantyl group, tetracyclododecyl group, isobornyl group, and norbornyl group is particularly desirable in consideration of industrial availability and the like. These polycyclic groups may be substituted with a linear or branched alkyl group having 1 to 5 carbon atoms.

Specific examples of the structural unit (a4) include structural units represented by general formulae (a4-1) to (a4-7) shown below.

[Chemical Formula 36.]

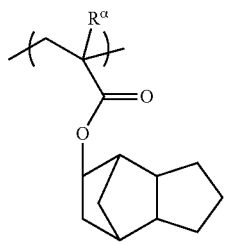
(a4-1)

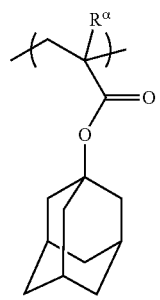
(a4-2)

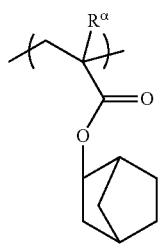
(a4-3)

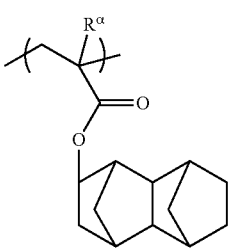
(a4-4)

-continued

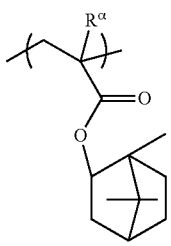
(a4-5)

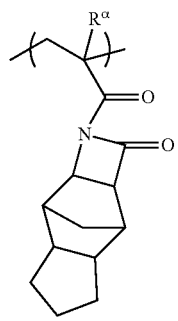
(a4-6)

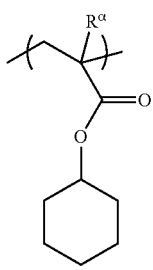
(a4-7)

In the formulae, $R^\alpha$ is the same as defined above.

As the structural unit (a4) contained in the component (A1), 1 type of structural unit may be used, or 2 or more types may be used.

When the component (A1) contains the structural unit (a4), the amount of the structural unit (a4) based on the combined total (100 mol %) of all structural units constituting the component (A1) is preferably 1 to 40 mol %, and more preferably 5 to 20 mol.

When the amount of the structural unit (a4) is at least as large as the lower limit of the above-mentioned preferable range, the effect of using the structural unit (a4) can be satisfactorily achieved. On the other hand, when the amount of the structural unit (a4) is no more than the upper limit of the above-mentioned preferable range, a good balance can be achieved with the other structural units.

Structural Unit (a10):

The structural unit (a10) is a structural unit represented by general formula (a10-1) shown below.

[Chemical Formula 37.]

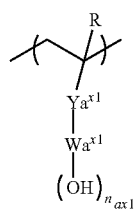

(a10-1)

In the formula, R represents a hydrogen atom, an alkyl group having 1 to 5 carbon atoms or a halogenated alkyl group having 1 to 5 carbon atoms; $Y a^{x1}$ represents a single bond or a divalent linking group; $Wa^{x1}$ represents an aromatic hydrocarbon group having a valency of ($n_{ax1}$+1); and $n_{ax1}$ represents an integer of 1 or more.

In general formula (a10-1), R represents a hydrogen atom, an alkyl group having 1 to 5 carbon atoms or a halogenated alkyl group having 1 to 5 carbon atoms.

As the alkyl group having 1 to 5 carbon atoms for R, a linear or branched alkyl group having 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group having 1 to 5 carbon atoms represented by R is a group in which part or all of the hydrogen atoms of the aforementioned alkyl group having 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group having 1 to 5 carbon atoms or a fluorinated alkyl group having 1 to 5 carbon atoms is preferable, and in view of industrial availability, a hydrogen atom, a methyl group or a trifluoromethyl group is more preferable, a hydrogen atom or a methyl group is still more preferable, and a methyl group is most preferable.

In formula (a10-1), $Ya^{x1}$ represents a single bond or a divalent linking group.

In the aforementioned chemical formula, the divalent linking group for $Ya^{x1}$ is not particularly limited, and preferable examples thereof include a divalent hydrocarbon group which may have a substituent and a divalent linking group containing a hetero atom.

Divalent Hydrocarbon Group which May have a Substituent:

In the case where $Ya^{x1}$ is a divalent linking group which may have a substituent, the hydrocarbon group may be either an aliphatic hydrocarbon group or an aromatic hydrocarbon group.

Aliphatic Hydrocarbon Group for $Ya^{x1}$

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

Linear or Branched Aliphatic Hydrocarbon Group

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group preferably has 2 to 10 carbon atoms, more preferably 3 to 6, still more preferably 3 or 4, and most preferably 3.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group having 1 to 5 carbon atoms is preferable.

The linear or branched aliphatic hydrocarbon group may or may not have a substituent. Examples of the substituent include a fluorine atom, a fluorinated alkyl group having 1 to 5 carbon atoms, and a carbonyl group.

Aliphatic Hydrocarbon Group Containing a Ring in the Structure Thereof

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which 2 hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group having 1 to 5 carbon atoms, and more preferably a methyl group, an ethyl group, a propyl group, an n-butyl group or a tert-butyl group.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and still more preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Aromatic Hydrocarbon Group for Ya$^{x1}$

The aromatic hydrocarbon group is a hydrocarbon group having at least one aromatic ring.

The aromatic ring is not particularly limited, as long as it is a cyclic conjugated compound having (4n+2)π electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Here, the number of carbon atoms within a substituent(s) is not included in the number of carbon atoms of the aromatic hydrocarbon group.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent.

Examples of substituents include an alkyl group, an alkoxy group, a halogen atom, a halogenated alkyl group, and a hydroxyl group.

The alkyl group as the substituent is preferably an alkyl group having 1 to 5 carbon atoms, and more preferably a methyl group, an ethyl group, a propyl group, an n-butyl group or a tert-butyl group.

As the alkoxy group, the halogen atom and the halogenated alkyl group for the substituent, the same groups as the aforementioned substituent groups for substituting a hydrogen atom within the cyclic aliphatic hydrocarbon group can be used.

Divalent Linking Group Containing a Hetero Atom

In the case where Ya$^{x1}$ represents a divalent linking group containing a hetero atom, preferable examples of the linking group include —O—, —C(=O)—O—, —O—C(=O)—, —C(=O)—, —O—C(=O)—O—, —C(=O)—NH—, —NH—, —NH—C(=NH)— (may be substituted with a substituent such as an alkyl group, an acyl group or the like), —S—, —S(=O)$_2$—, —S(=O)$_2$—O—, and a group represented by general formula: —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m'}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represents a divalent hydrocarbon group which may have a substituent, O represents an oxygen atom, and m' represents an integer of 0 to 3].

In the case where the divalent linking group containing a hetero atom is —C(=O)—NH—, —C(=O)—NH—C(=O)—, —NH— or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In general formulae —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m'}$—Y$^{22}$—, —Y$^{21}$—O—C(=O)—Y$^{22}$— or —Y$^{21}$—S(=O)$_2$—O—Y$^{22}$—, Y$^{21}$ and Y$^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group for Ya$^{x1}$.

As Y$^{21}$, a linear aliphatic hydrocarbon group is preferable, more preferably a linear alkylene group, still more preferably a linear alkylene group having 1 to 5 carbon atoms, and a methylene group or an ethylene group is particularly desirable.

As Y$^{22}$, a linear or branched aliphatic hydrocarbon group is preferable, and a methylene group, an ethylene group or an alkylmethylene group is more preferable. The alkyl group within the alkylmethylene group is preferably a linear alkyl group having 1 to 5 carbon atoms, more preferably a linear alkyl group having 1 to 3 carbon atoms, and most preferably a methyl group.

In the group represented by the formula —[Y$^{21}$—C(=O)—O]$_{m''}$-Y$^{22}$—, m'' represents an integer of 0 to 3, preferably an integer of 0 to 2, more preferably 0 or 1, and most preferably 1. Namely, it is particularly desirable that the group represented by the formula —[Y$^{21}$—C(=O)—O]$_{m''}$-Y$^{22}$— is a group represented by the formula —Y$^{21}$—C(=O)—O—Y$^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

Among the above examples, as $Ya^{x1}$, a single bond, an ester bond [—C(=O)—O—, —O—C(=O)—], an ether bond (—O—), a linear or branched alkylene group, or a combination of these is preferable, and a single bond or an ester bond [—C(=O)—O—, —O—C(=O)—] is more preferable.

In formula (a10-1), $Wa^{x1}$ represents an aromatic hydrocarbon group having a valency of $(n_{ax1}+1)$.

Examples of the aromatic hydrocarbon group for $Wa^{x1}$ include a group obtained by removing $(n_{ax1}+1)$ hydrogen atoms from an aromatic ring. The aromatic ring is not particularly limited, as long as it is a cyclic conjugated compound having $(4n+2)\pi$ electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Specific examples of the aromatic ring include an aromatic hydrocarbon ring, such as benzene, naphthalene, anthracene or phenanthrene; and an aromatic heterocyclic ring in which part of the carbon atoms constituting the aromatic hydrocarbon ring has been substituted with a heteroatom. Examples of the hetero atom within the aromatic hetero rings include an oxygen atom, a sulfur atom and a nitrogen atom. Specific examples of the aromatic hetero ring include a pyridine ring and a thiophene ring.

Further examples of the aromatic hydrocarbon group for $Wa^{x1}$ include a group in which $(n_{ax1}+1)$ hydrogen atom(s) has been removed from an aromatic group containing 2 or more aromatic rings (e.g., biphenyl, fluorene, or the like).

Among the above examples, as $Wa^{x1}$, a group in which $(n_{ax1}+1)$ hydrogen atoms have been removed from benzene, naphthalene, anthracene or biphenyl is preferable, a group in which $(n_{ax1}+1)$ hydrogen atoms have been removed from benzene or naphthalene is more preferable, and a group in which $(n_{ax1}+1)$ hydrogen atoms have been removed from benzene is still more preferable.

In formula (a10-1), $n_{ax1}$ is an integer of 1 or more, preferably an integer of 1 to 10, more preferably an integer of 1 to 5, still more preferably 1, 2 or 3, and most preferably 1 or 2.

Specific examples of the structural unit (a10) represented by formula (a10-1) are shown below.

In the formulae shown below, $R^1$ represents a hydrogen atom, a methyl group or a trifluoromethyl group.

[Chemical Formula 38.]

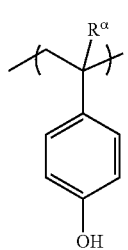

(a10-1-11)

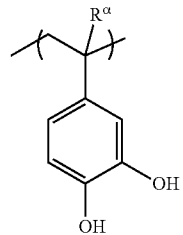

(a10-1-12)

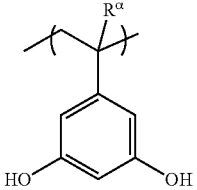

(a10-1-13)

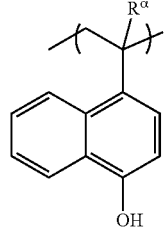

(a10-1-14)

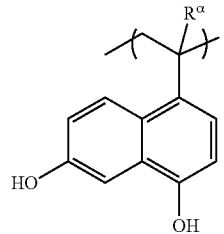

(a10-1-15)

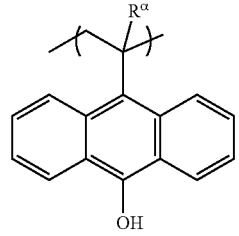

(a10-1-16)

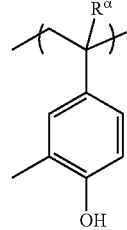

(a10-1-17)

[Chemical Formula 39.]
(a10-1-18) 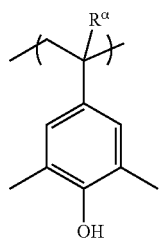
(a10-1-21) 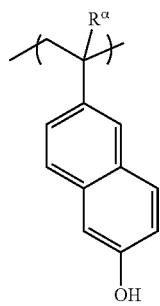
(a10-1-22) 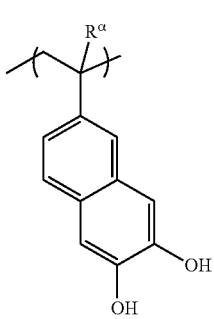
(a10-1-23) 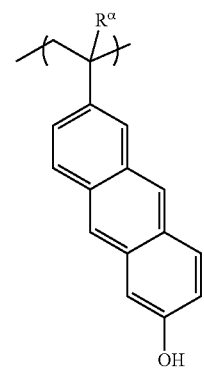
(a10-1-24) 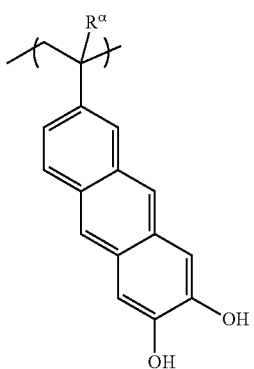
[Chemical Formula 40.]
(a10-1-31) 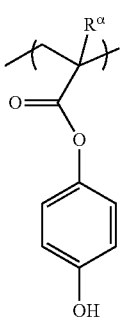
(a10-1-32) 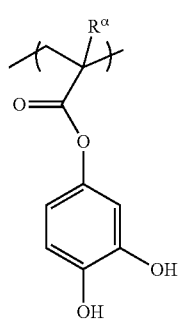
(a10-1-33) 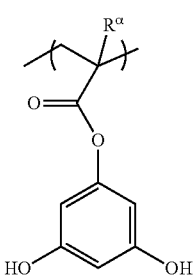
(a10-1-34) 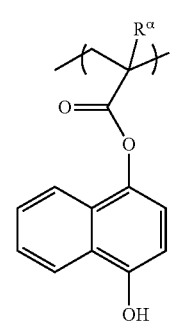
(a10-1-35) 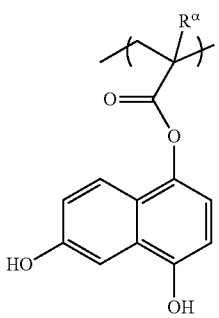

-continued (a10-1-36)

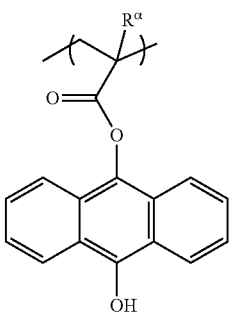

[Chemical Formula 41.]

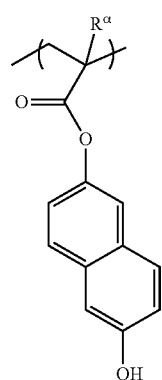
(a10-1-41)

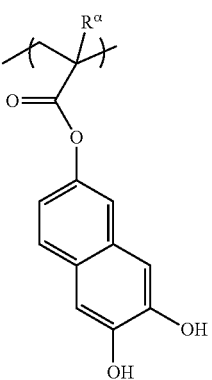
(a10-1-42)

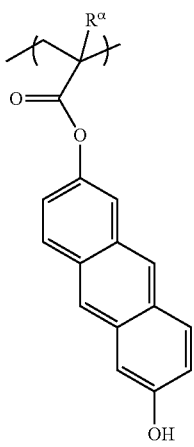
(a10-1-43)

-continued (a10-1-44)

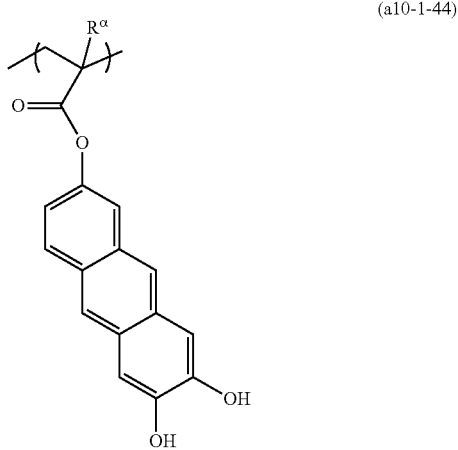

As the structural unit (a10) contained in the component (A1), 1 kind of structural unit may be used, or 2 or more kinds of structural units may be used.

When the component (A1) includes the structural unit (a10), the amount of the structural unit (a10) within the component (A1), based on the combined total of all structural units constituting the component (A1) (100 mol %) is preferably 20 to 80 mol %, more preferably 20 to 70 mol %, still more preferably 25 to 60 mol %, and most preferably 30 to 50 mol %.

When the amount of the structural unit (a10) is at least as large as the lower limit of the above preferable range, the sensitivity may be more reliably enhanced. On the other hand, when the amount of the structural unit (a10) is no more than the upper limit of the above-mentioned range, a good balance may be reliably achieved with the other structural units.

Structural Unit Derived from Styrene or a Derivative Thereof (Structural Unit (St))

The term "styrene" is a concept including styrene and compounds in which the hydrogen atom at the α-position of styrene is substituted with a substituent such as an alkyl group or a halogenated alkyl group. Examples of the alkyl group as the substituent include an alkyl group having 1 to 5 carbon atoms. Examples of the halogenated alkyl group as the substituent include a halogenated alkyl group having 1 to 5 carbon atoms.

Examples of the "styrene derivative" include styrene which has a substituent other than a hydroxy group bonded to the benzene ring and may have the hydrogen atom on the α-position substituted with a substituent.

Here, the α-position (carbon atom on the α-position) refers to the carbon atom having the benzene ring bonded thereto, unless specified otherwise.

A "structural unit derived from styrene" or "structural unit derived from a styrene derivative" refers to a structural unit that is formed by the cleavage of the ethylenic double bond of styrene or a styrene derivative.

As the structural unit (st) contained in the component (A1), 1 kind of structural unit may be used, or 2 or more kinds of structural units may be used.

When the component (A1) includes the structural unit (st), the amount of the structural unit (st) based on the combined total of all structural units constituting the component (A1) (100 mol %) is preferably 1 to 30 mol %, and more preferably 3 to 20 mol %.

In the resist composition of the present embodiment, the resin component (A1) contains a polymer having the structural unit (a0) (hereafter, this polymer is referred to as "component (A1-1)"). As the component (A1-1), 1 kind of the polymer may be used, or 2 or more kinds of the polymers may be used in combination.

The component (A1-1) preferably includes, for example, a copolymer having a structural unit (a0), a structural unit (a2) and any other structural unit if desired. Preferable examples of the component (A1-1) include a copolymer consisting of a repeating structure of a structural unit (a0) and a structural unit (a2); and a copolymer consisting of a repeating structure of a structural unit (a0), a structural unit (a2) and a structural unit (a3).

Alternatively, the component (A1-1) preferably includes, for example, a copolymer having a structural unit (a0), a structural unit (a10) and any other structural unit if desired. Preferable examples of such component (A1-1) include a copolymer consisting of a repeating structure of a structural unit (a0) and a structural unit (a10).

<<Component (A2)>>

In the resist composition of the present embodiment, as the component (A), "a base component which exhibits changed solubility in a developing solution under action of acid" other than the component (A1) (hereafter, referred to as "component (A2)") may be used in combination.

As the component (A2), there is no particular limitation, and any of the multitude of conventional base resins used within chemically amplified resist compositions may be arbitrarily selected for use.

As the component (A2), one kind of a polymer or a low molecular weight compound may be used, or a combination of two or more kinds may be used.

In the component (A), the amount of the component (A1) based on the total weight of the component (A) is preferably 50% by weight or more, more preferably 75% by weight or more, still more preferably 90% by weight or more, and may be even 100% by weight.

When the amount of the component (A1) is at least as large as the lower limit of the above preferable range, sensitivity may be improved, and a resist pattern with improved lithography properties such as resolution and reduced roughness may be reliably formed.

In the resist composition of the present embodiment, the amount of the component (A) may be appropriately adjusted depending on the thickness of the resist film to be formed, and the like.

<Other Components>

The resist composition of the present embodiment may contain, in addition to the aforementioned component (A), any other components other than the component (A). Examples of the other components include the component (B), the component (D), the component (E), the component (F) and the component (S) described below.

<<Acid-Generator Component (B)>>

The resist composition of the present embodiment may include, in addition to the components (A), an acid-generator component (hereafter, sometimes referred to as "component (B)").

As the component (B), there is no particular limitation, and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators. Among these, it is preferable to use an onium salt acid generator.

As the onium salt acid generator, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be used.

[Chemical Formula 42.]

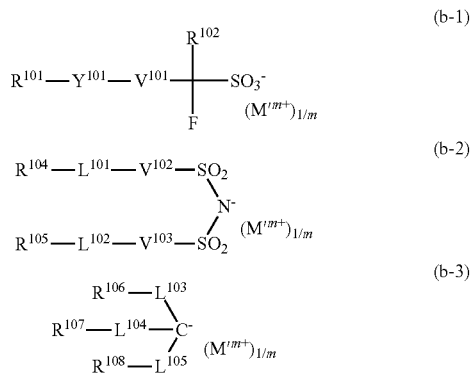

In the formulae, $R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring;

$R^{102}$ represents a fluorine atom or a fluorinated alkyl group having 1 to 5 carbon atoms; $Y^{101}$ represents a single bond or a divalent linking group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; $L^{103}$ to $L^{105}$ each independently represents a single bond, —CO— or —SO$_2$—; m represents an integer of 1 or more; and $M'^{m+}$ represents an m-valent onium cation.

{Anion Moiety}

Anion Moiety of Component (b-1)

In the formula (b-1), $R^{101}$ represents a cyclic group which may have a substituent, a chain-like alkyl group which may have a substituent or a chain-like alkenyl group which may have a substituent.

Cyclic Group which May have a Substituent:

The cyclic group is preferably a cyclic hydrocarbon group, and the cyclic hydrocarbon group may be either an aromatic hydrocarbon group or an aliphatic hydrocarbon group. An "aliphatic hydrocarbon group" refers to a hydrocarbon group that has no aromaticity. The aliphatic hydrocarbon group may be either saturated or unsaturated, but in general, the aliphatic hydrocarbon group is preferably saturated.

The aromatic hydrocarbon group for $R^{101}$ is a hydrocarbon group having an aromatic ring. The aromatic hydrocarbon group preferably has 3 to 30 carbon atoms, more preferably 5 to 30 carbon atoms, still more preferably 5 to 20 carbon atoms, still more preferably 6 to 15 carbon atoms, and most preferably 6 to 10 carbon atoms. Here, the number of carbon atoms within a substituent(s) is not included in the number of carbon atoms of the aromatic hydrocarbon group.

Examples of the aromatic ring contained in the aromatic hydrocarbon group represented by $R^{101}$ include benzene, fluorene, naphthalene, anthracene, phenanthrene and biphenyl; and aromatic hetero rings in which part of the carbon atoms constituting the aforementioned aromatic rings has been substituted with a hetero atom. Examples of the hetero atom within the aromatic hetero rings include an oxygen atom, a sulfur atom and a nitrogen atom.

Specific examples of the aromatic hydrocarbon group represented by $R^{101}$ include a group in which one hydrogen atom has been removed from the aforementioned aromatic ring (i.e., an aryl group, such as a phenyl group or a naphthyl group), and a group in which one hydrogen of the aforementioned aromatic ring has been substituted with an alkylene group (e.g., an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atom, more preferably 1 or 2, and most preferably 1.

Examples of the cyclic aliphatic hydrocarbon group for $R^{101}$ include aliphatic hydrocarbon groups containing a ring in the structure thereof.

As examples of the hydrocarbon group containing a ring in the structure thereof, an alicyclic hydrocarbon group (a group in which one hydrogen atom has been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which one or more hydrogen atoms have been removed from a polycycloalkane is preferable, and the polycyclic group preferably has 7 to 30 carbon atoms. Among polycycloalkanes, a polycycloalkane having a bridged ring polycyclic skeleton, such as adamantane, norbornane, isobornane, tricyclodecane or tetracyclododecane, and a polycycloalkane having a condensed ring polycyclic skeleton, such as a cyclic group having a steroid skeleton are preferable.

Among these examples, as the cyclic aliphatic hydrocarbon group for $R^{101}$, a group in which one or more hydrogen atoms have been removed from a monocycloalkane or a polycycloalkane is preferable, a group in which one or more hydrogen atoms have been removed from a polycycloalkane is more preferable, an adamantyl group or a norbornyl group is still more preferable, and an adamantyl group is most preferable.

The linear or branched aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group having 1 to 5 carbon atoms is preferable.

The cyclic hydrocarbon group for $R^{101}$ may contain a hetero atom such as a heterocycle. Specific examples include lactone-containing cyclic groups represented by the aforementioned general formulae (a2-r-1) to (a2-r-7), the —$SO_2$— containing cyclic group represented by the aforementioned formulae (a5-r-1) to (a5-r-4), and other heterocyclic groups represented by chemical formulae (r-hr-1) to (r-hr-16) shown below.

[Chemical Formula 43.]

(r-hr-1)

(r-hr-2)

(r-hr-3)

(r-hr-4)

(r-hr-5)

(r-hr-6)

(r-hr-7)

-continued

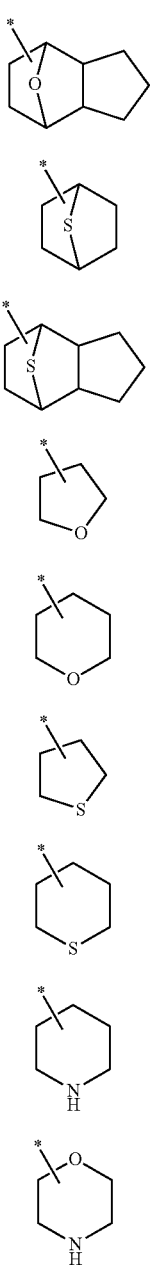

(r-hr-8)

(r-hr-9)

(r-hr-10)

(r-hr-11)

(r-hr-12)

(r-hr-13)

(r-hr-14)

(r-hr-15)

(r-hr-16)

As the substituent for the cyclic group for $R^1$, an alkyl group, an alkoxy group, a halogen atom, a halogenated alkyl group, a hydroxyl group, a carbonyl group, a nitro group or the like can be used.

The alkyl group as the substituent is preferably an alkyl group having 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group having 1 to 5 carbon atoms (e.g., a methyl group, an ethyl group, a propyl group, an n-butyl group or a tert-butyl group) have been substituted with the aforementioned halogen atoms.

The carbonyl group as the substituent is a group that substitutes a methylene group (—$CH_2$—) constituting the cyclic hydrocarbon group.

Chain Alkyl Group which May have a Substituent:

The chain-like alkyl group for $R^{101}$ may be linear or branched.

The linear alkyl group preferably has 1 to 20 carbon atoms, more preferably 1 to 15 carbon atoms, and still more preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15 carbon atoms, and still more preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Chain Alkenyl Group which May have a Substituent:

The chain-like alkenyl group for $R^{101}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group.

Among these examples, as the chain-like alkenyl group, a linear alkenyl group is preferable, a vinyl group or a propenyl group is more preferable, and a vinyl group is most preferable.

As the substituent for the chain-like alkyl group or alkenyl group for $R^{101}$, an alkoxy group, a halogen atom, a halogenated alkyl group, a hydroxyl group, a carbonyl group, a nitro group, an amino group, a cyclic group for $R^{101}$ or the like can be used.

Among these examples, as $R^{101}$, a cyclic group which may have a substituent is preferable, and a cyclic hydrocarbon group which may have a substituent is more preferable. Specifically, for example, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an —$SO_2$— containing cyclic group represented by any one of the aforementioned formula (a5-r-1) to (a5-r-4) are preferable.

In formula (b-1), $Y^{101}$ represents a single bond or a divalent linking group containing an oxygen atom.

In the case where $Y^{101}$ is a divalent linking group containing an oxygen atom, $Y^{101}$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group. Furthermore, the combinations may have a sulfonyl group (—SO$_2$—) bonded thereto. Examples of divalent linking groups containing an oxygen atom include linking groups represented by general formulae (y-a1-1) to (y-a1-7) shown below.

[Chemical Formula 44.]

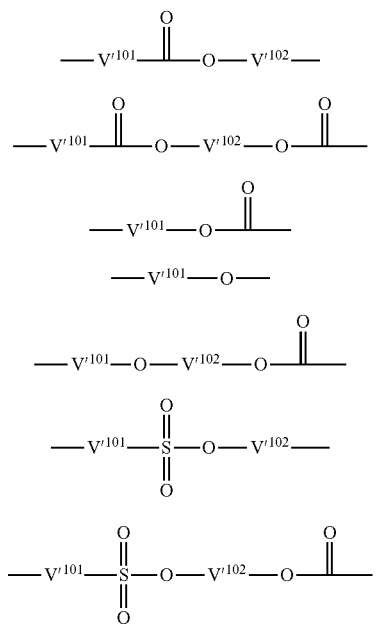

In the formulae, $V'^{101}$ represents a single bond or an alkylene group having 1 to 5 carbon atoms; $V'^{102}$ represents a divalent saturated hydrocarbon group having 1 to 30 carbon atoms.

The divalent saturated hydrocarbon group for $V'^{102}$ is preferably an alkylene group having 1 to 30 carbon atoms, more preferably an alkylene group having 1 to 10 carbon atoms, and still more preferably an alkylene group having 1 to 5 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—CH$_2$—]; an alkylmethylene group, such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; an ethylene group [—CH$_2$CH$_2$—]; an alkylethylene group, such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; a trimethylene group (n-propylene group) [—CH$_2$CH$_2$CH$_2$—]; an alkyltrimethylene group, such as —CH(CH$_3$)CH$_2$CH$_2$— and —CH$_2$CH(CH$_3$)CH$_2$—; a tetramethylene group [—CH$_2$CH$_2$CH$_2$CH$_2$—]; an alkyltetramethylene group, such as —CH(CH$_3$)CH$_2$CH$_2$CH$_2$—, —CH$_2$CH(CH$_3$)CH$_2$CH$_2$—; and a pentamethylene group [—CH$_2$CH$_2$CH$_2$CH$_2$CH$_2$—].

Further, part of methylene group within the alkylene group for $V'^{101}$ and $V'^{102}$ may be substituted with a divalent aliphatic cyclic group having 5 to 10 carbon atoms. The aliphatic cyclic group is preferably a divalent group in which one hydrogen atom has been removed from the cyclic aliphatic hydrocarbon group (monocyclic alicyclic hydrocarbon group or polycyclic alicyclic hydrocarbon group) for $R^{101}$ in the aforementioned formula (b-1), and a cyclohexylene group, 1,5-adamantylene group or 2,6-adamantylene group is preferable.

$Y^{101}$ is preferably a divalent linking group containing an ether bond or a divalent linking group containing an ester bond, and groups represented by the aforementioned formulas (y-a1-1) to (y-a1-5) are preferable.

In formula (b-1), $V^{101}$ represents a single bond, an alkylene group or a fluorinated alkylene group. The alkylene group and the fluorinated alkylene group for $V^{101}$ preferably has 1 to 4 carbon atoms. Examples of the fluorinated alkylene group for $V^{101}$ include a group in which part or all of the hydrogen atoms within the alkylene group for $V^{101}$ have been substituted with fluorine. Among these examples, as $V^{101}$, a single bond or a fluorinated alkylene group having 1 to 4 carbon atoms is preferable.

In formula (b-1), $R^{102}$ represents a fluorine atom or a fluorinated alkyl group having 1 to 5 carbon atoms. $R^{102}$ is preferably a fluorine atom or a perfluoroalkyl group having 1 to 5 carbon atoms, and more preferably a fluorine atom.

As a specific example of the anion moiety for the component (b-1), in the case where $Y^{101}$ a single bond, a fluorinated alkylsulfonate anion such as a trifluoromethanesulfonate anion or a perfluorobutanesulfonate anion can be mentioned; and in the case where $Y^{101}$ represents a divalent linking group containing an oxygen atom, anions represented by formulae (an-1) to (an-3) shown below can be mentioned.

[Chemical Formula 45.]

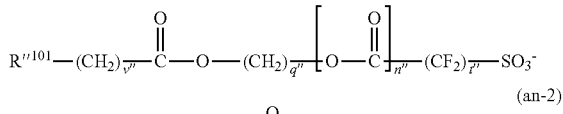

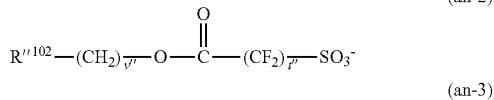

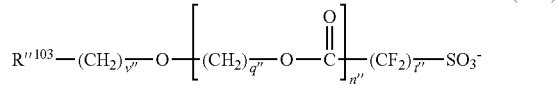

In the formulae, $R''^{101}$ represents an aliphatic cyclic group which may have a substituent, a group represented by any one of the aforementioned formulas (r-hr-1) to (r-hr-6) or a chain-like alkyl group which may have a substituent; $R''^{102}$ represents an aliphatic cyclic group which may have a substituent, a lactone-containing cyclic group represented by any one of the aforementioned formulae (a2-r-1) to (a2-r-7) or an —SO$_2$— containing cyclic group represented by any one of the aforementioned formulae (a5-r-1) to (a5-r-4); $R'''^{103}$ represents an aromatic cyclic group which may have a substituent, an aliphatic cyclic group which may have a substituent or a chain-like alkenyl group which may have a substituent; v″ represents an integer of 0 to 3; q″ represents an integer of 1 to 20; t″ represents an integer of 1 to 3; and n″ represents 0 or 1.

As the aliphatic cyclic group for $R''^{101}$, $R''^{102}$ and $R''^{103}$ which may have a substituent, the same groups as the cyclic aliphatic hydrocarbon group for $R^{101}$ described above are preferable. As the substituent, the same groups as those described above for substituting the cyclic aliphatic hydrocarbon group for $R^{101}$ can be mentioned.

As the aromatic cyclic group for $R''^{103}$ which may have a substituent, the same groups as the aromatic hydrocarbon group for the cyclic hydrocarbon group represented by $R^{101}$ described above are preferable. The substituent is the same as defined for the substituent for the aromatic hydrocarbon group represented by $R^{101}$.

As the chain-like alkyl group for $R''^{101}$ which may have a substituent, the same groups as those described above for $R^{101}$ are preferable. As the chain-like alkenyl group for $R''^{103}$ which may have a substituent, the same groups as those described above for $R^{101}$ are preferable.

Anion Moiety of Component (b-2)

In formula (b-2), $R^{104}$ and $R^{105}$ each independently represents a cyclic group which may have a substituent, a chain-like alkyl group which may have a substituent or a chain-like alkenyl group which may have a substituent, and is the same as defined for $R^{101}$ in formula (b-1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$, the more the solubility in a resist solvent is improved. Further, in the chain-like alkyl group for $R^{104}$ and $R^{105}$, it is preferable that the number of hydrogen atoms substituted with fluorine atoms is as large as possible because the acid strength increases and the transparency to high energy radiation of 200 nm or less or electron beam is improved.

The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b-2), $V^{102}$ and $V^{103}$ each independently represents a single bond, an alkylene group or a fluorinated alkylene group, and is the same as defined for $V^{101}$ in formula (b-1).

In formula (b-2), $L^{101}$ and $L^{102}$ each independently represents a single bond or an oxygen atom.

Anion Moiety of Component (b-3)

In formula (b-3), $R^{106}$ to $R^{108}$ each independently represents a cyclic group which may have a substituent, a chain-like alkyl group which may have a substituent or a chain-like alkenyl group which may have a substituent, and is the same as defined for $R^{101}$ in formula (b-1).

$L^{103}$ to $L^{105}$ each independently represents a single bond, —CO— or —SO$_2$—.

{Cation Moiety}

In formulae (b-1), (b-2) and (b-3), m represents an integer of 1 or more, $M^{m+}$ represents an onium cation having a valency of m, preferably a sulfonium cation or an iodonium cation, and most preferably an organic cation represented by any one of the following formulae (ca-1) to (ca-5).

[Chemical Formula 46.]

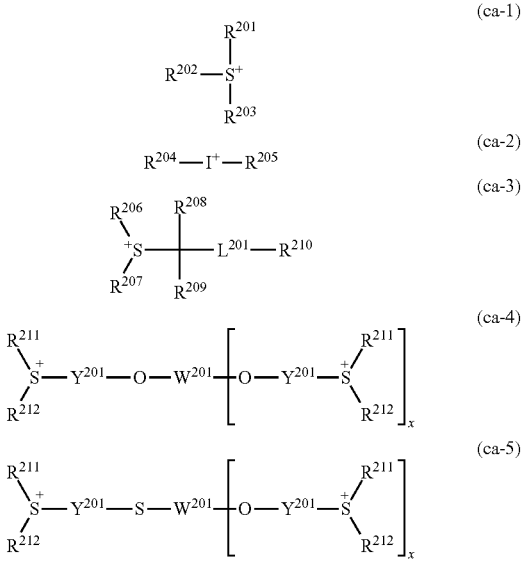

In the formulae, $R^{201}$ to $R^{207}$, $R^{211}$ and $R^{212}$ each independently represents an aryl group, an alkyl group or an alkenyl group, provided that two of $R^{201}$ to $R^{203}$, $R^{206}$ and $R^{207}$, or $R^{211}$ and $R^{212}$ may be mutually bonded to form a ring with the sulfur atom; $R^{208}$ and $R^{209}$ each independently represents a hydrogen atom or an alkyl group having 1 to 5 carbon atoms; $R^{210}$ represents an aryl group which may have a substituent, an alkyl group which may have a substituent, an alkenyl group which may have a substituent, or an —SO$_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$, an unsubstituted aryl group having 6 to 20 carbon atoms can be mentioned, and a phenyl group or a naphthyl group is preferable.

The alkyl group for $R^{201}$ to $R^{207}$, $R^{211}$ and $R^{212}$ is preferably a chain-like or cyclic alkyl group having 1 to 30 carbon atoms.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, and groups represented by formulae (ca-r-1) to (ca-r-7) shown below.

[Chemical Formula 47.]

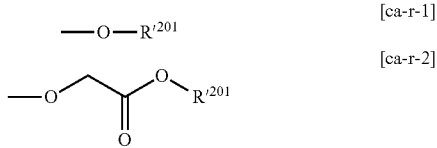

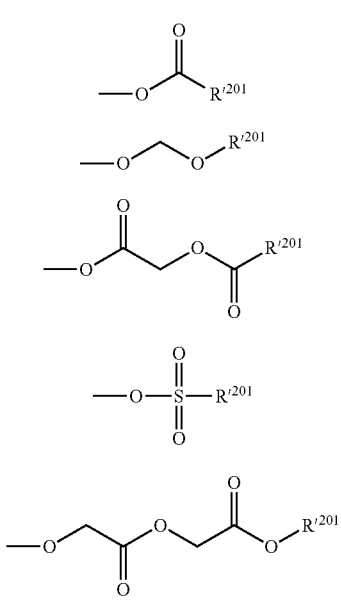

[ca-r-3]
[ca-r-4]
[ca-r-5]
[ca-r-6]
[ca-r-7]

In the formulae, each $R'^{201}$ independently represents a hydrogen atom, a cyclic group which may have a substituent, a chain-like alkyl group which may have a substituent, or a chain-like alkenyl group which may have a substituent.

As the cyclic group which may have a substituent, the chain-like alkyl group which may have a substituent and the chain-like alkenyl group which may have a substituent for $R'^{201}$, the same groups as those described above for $R^{101}$ can be mentioned. As the cyclic group which may have a substituent and chain-like alkyl group which may have a substituent, the same groups as those described above for the acid dissociable group represented by the aforementioned formula (a1-r-2) can be also mentioned.

When $R^{201}$ to $R^{203}$, $R^{206}$, $R^{207}$, $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group having 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ and $R^{209}$ each independently represents a hydrogen atom or an alkyl group having 1 to 5 carbon atoms, preferably a hydrogen atom or an alkyl group having 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an —SO$_2$— containing cyclic group which may have a substituent.

Examples of the aryl group for $R^{210}$ include an unsubstituted aryl group having 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

The —SO$_2$— containing cyclic group for $R^{210}$ which may have a substituent is the same as defined for the —SO$_2$— containing cyclic group represented by any of the aforementioned general formulae (a5-r-1) to (a5-r-4). Among these examples, the "—SO$_2$— containing polycyclic group" is preferable, and a group represented by general formula (a5-r-1) is more preferable.

In formulae (ca-4) and (ca-5), each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{101}$ in the aforementioned formula (b-1).

Examples of the alkylene group and alkenylene group for $Y^{201}$ include groups in which one hydrogen atom has been removed from the chain-like alkyl group or the chain-like alkenyl group given as an example of $R^{101}$ in the aforementioned formula (b-1).

In formulae (ca-4) and (ca-5), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups (which may have a substituent) as those described above for $Ya^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) include cations represented by formulae (ca-1-1) to (ca-1-127) shown below.

[Chemical Formula 48.]

(ca-1-1)

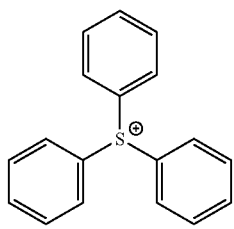

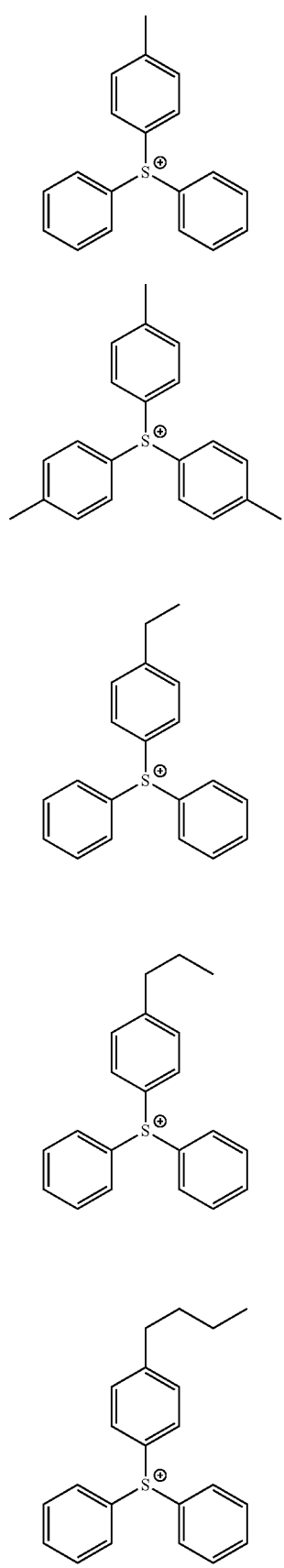
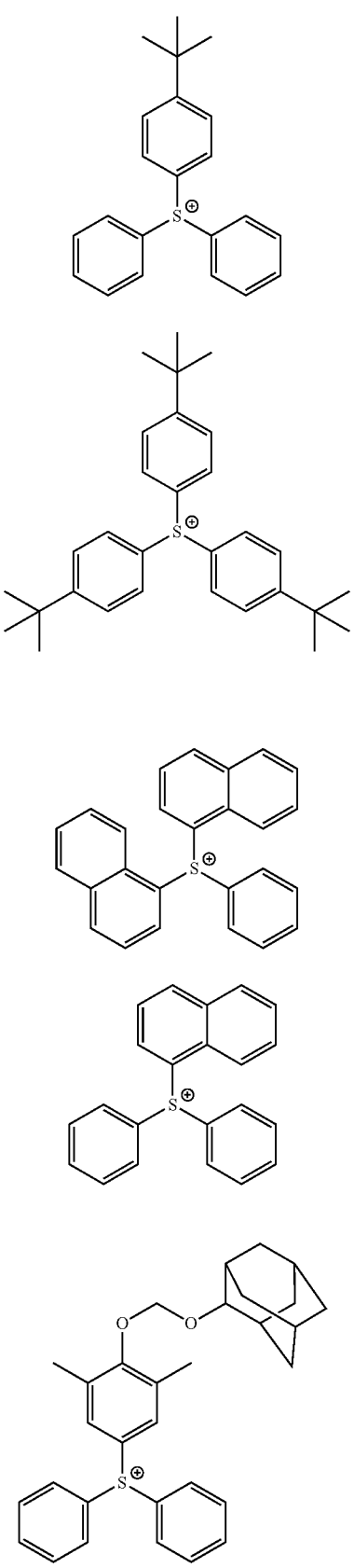

(ca-1-12)
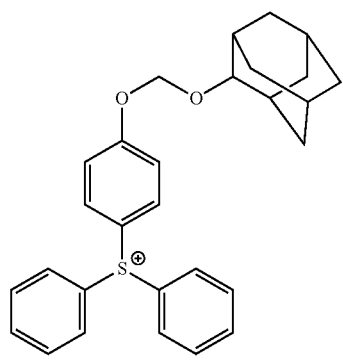
(ca-1-13)
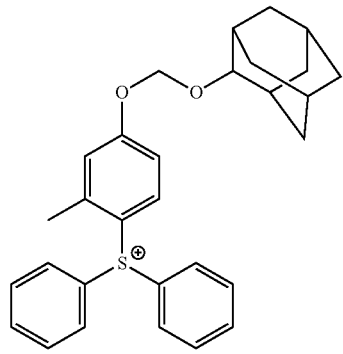
(ca-1-14)
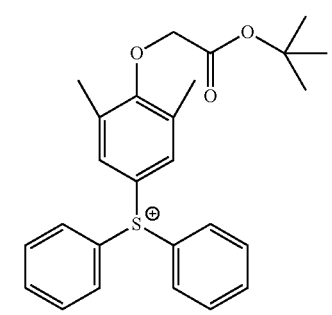
(ca-1-15)
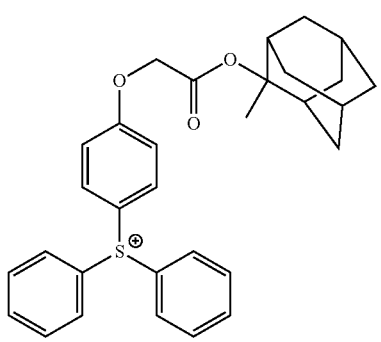
(ca-1-16)
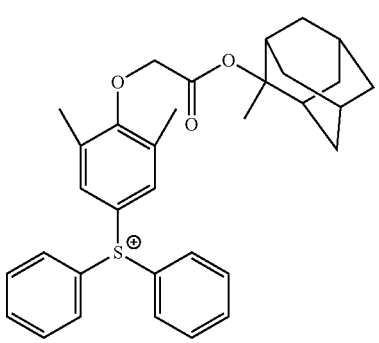
[Chemical Formula 49.]
(ca-1-17)
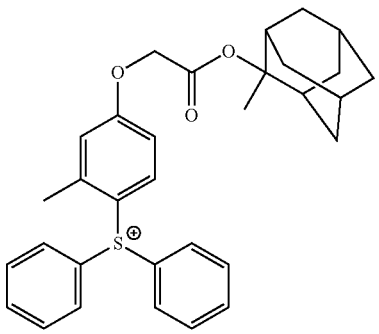
(ca-1-18)
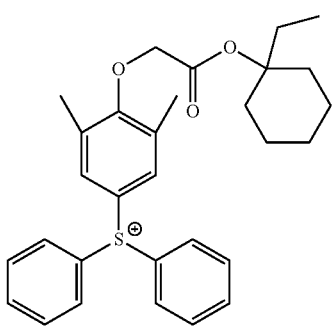
(ca-1-19)
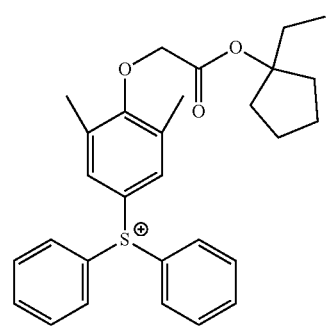

-continued
(ca-1-20)
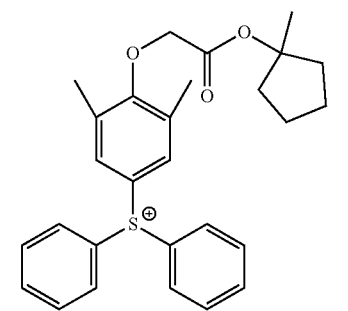
(ca-1-21)
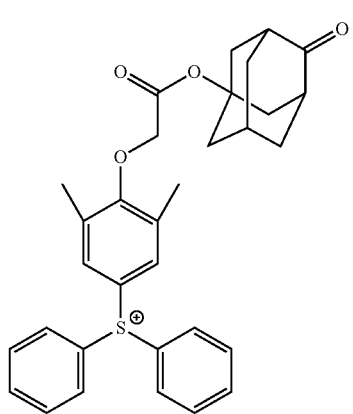
(ca-1-22)
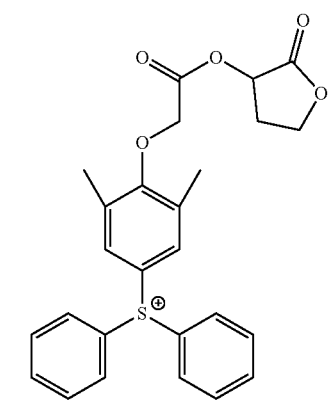
(ca-1-23)
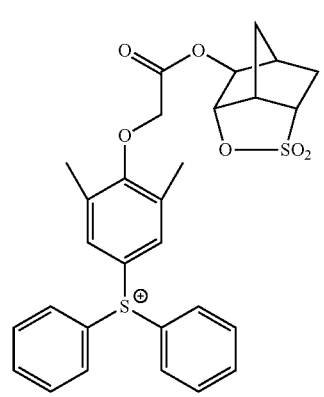
-continued
(ca-1-24)
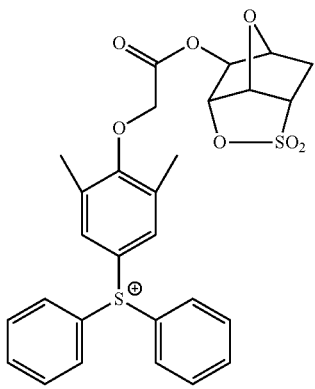
(ca-1-25)
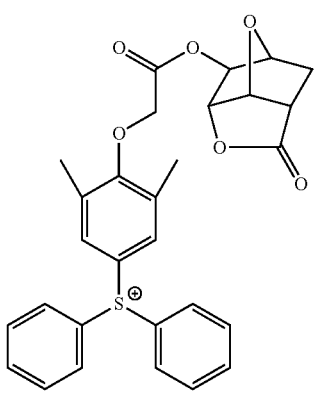
(ca-1-26)
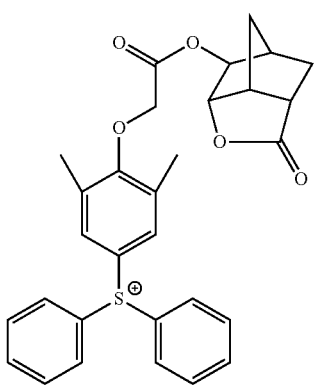
(ca-1-27)
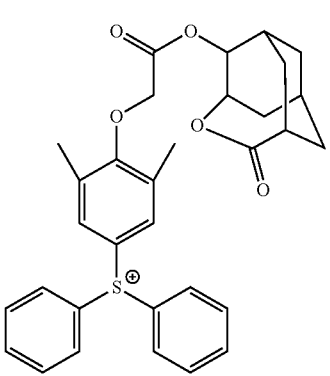

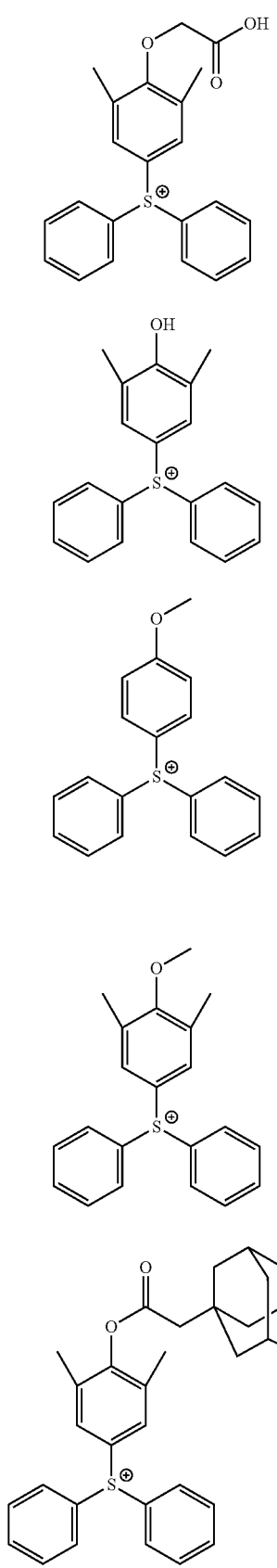
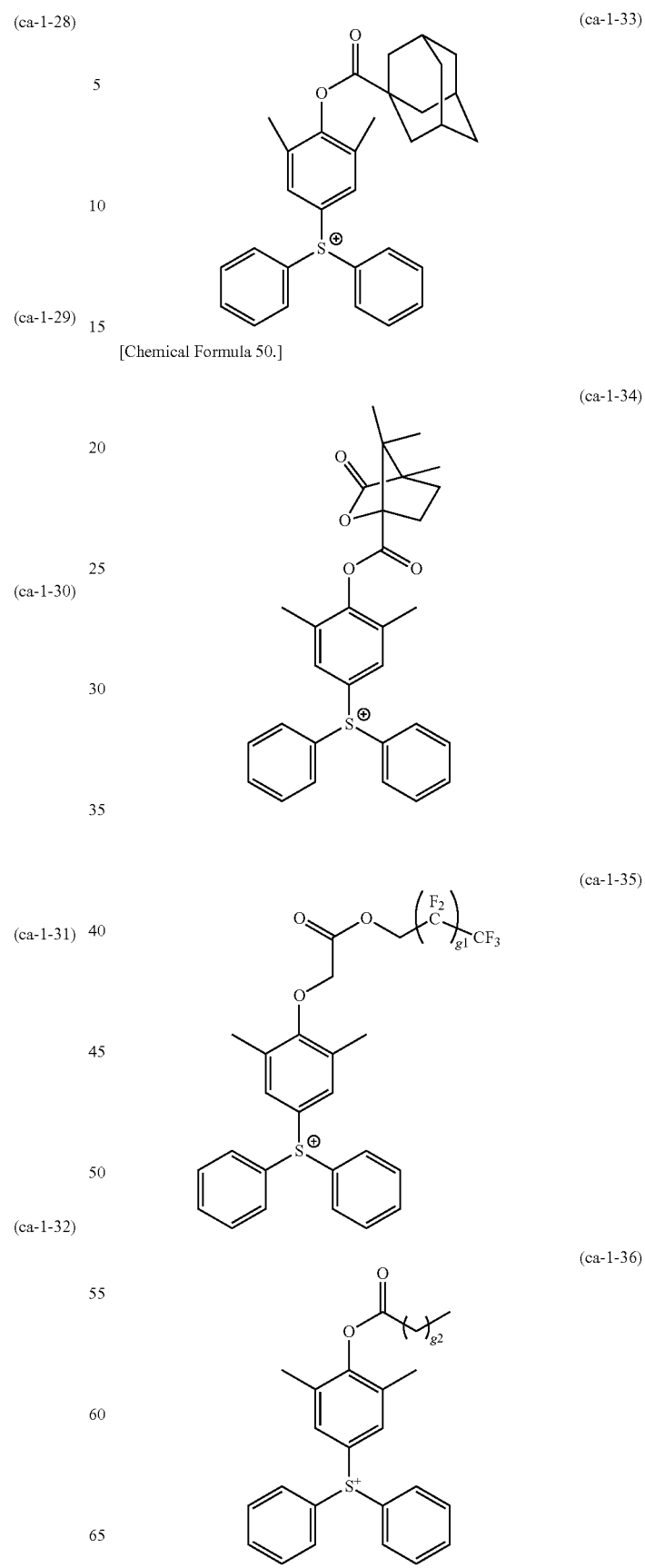
[Chemical Formula 50.]

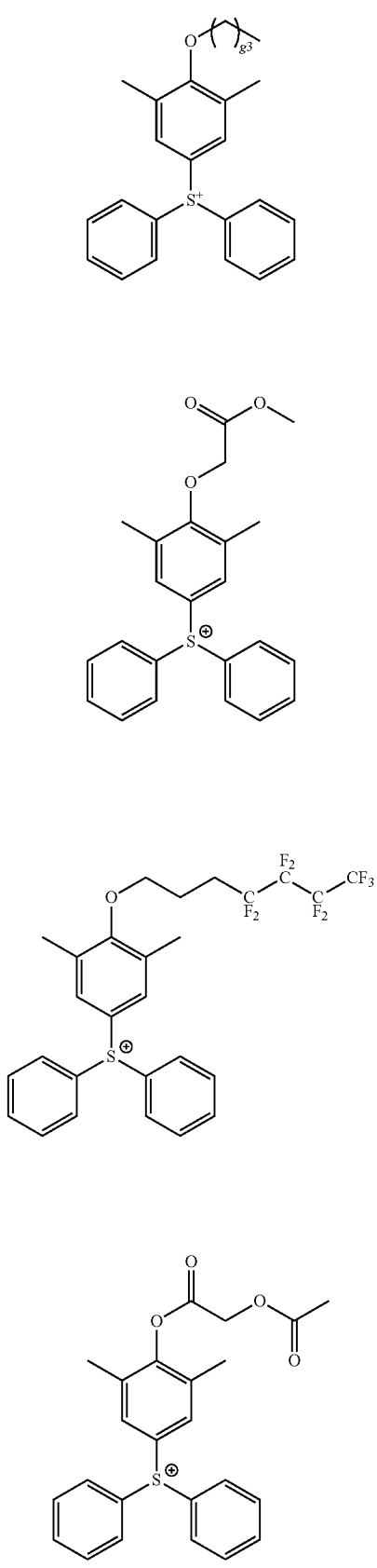
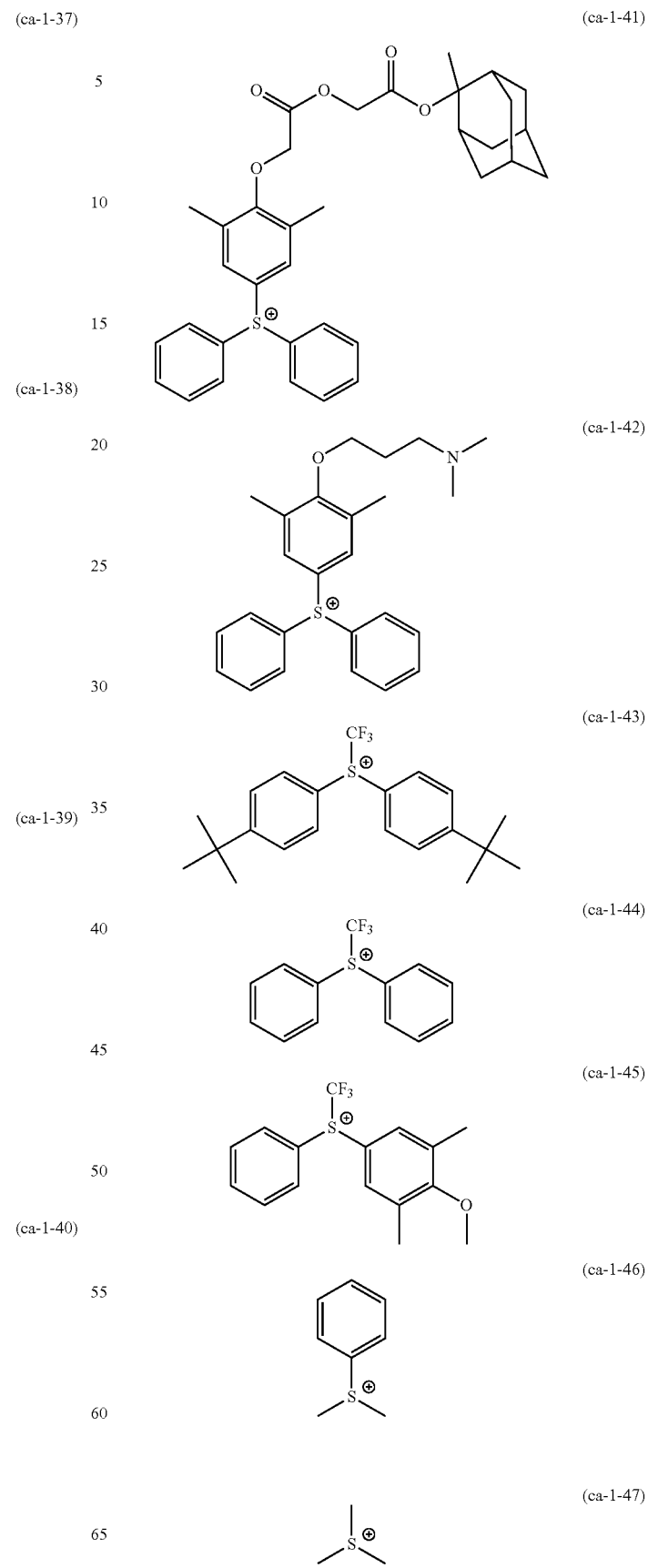

(ca-1-48)
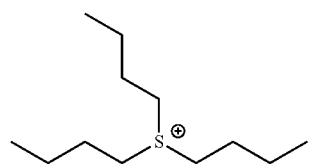
(ca-1-49)
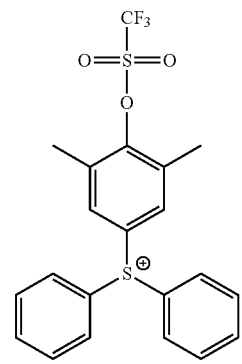
(ca-1-50)
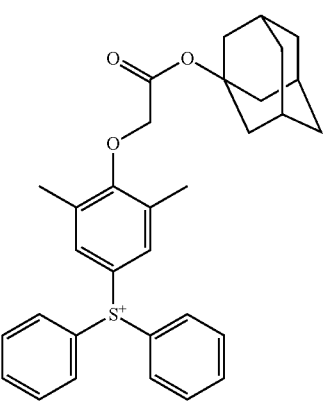
(ca-1-51)
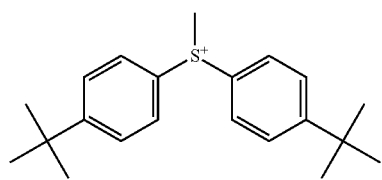
In the formulae, g1, g2 and g3 represent recurring numbers, wherein g1 is an integer of 1 to 5, g2 is an integer of 0 to 20, and g3 is an integer of 0 to 20.
[Chemical Formula 51.]
(ca-1-52)
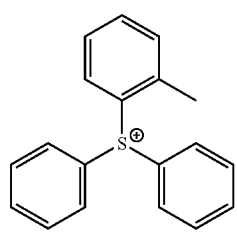
(ca-1-53)
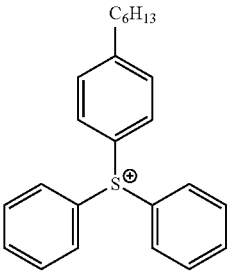
(ca-1-54)
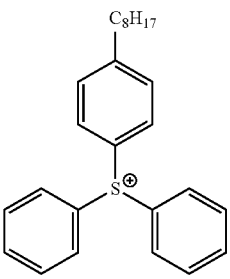
(ca-1-55)
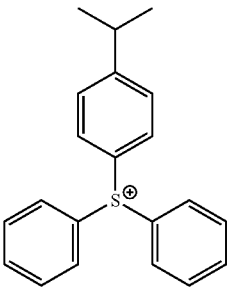
(ca-1-56)
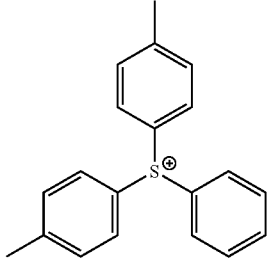
(ca-1-57)
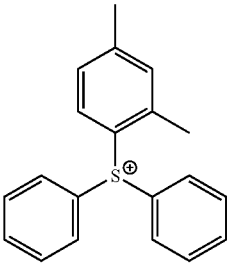
(ca-1-58)
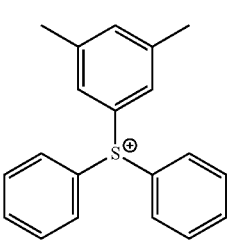

(ca-1-59)
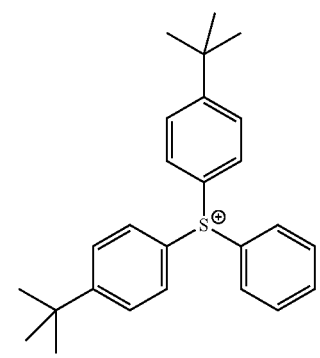
(ca-1-60)
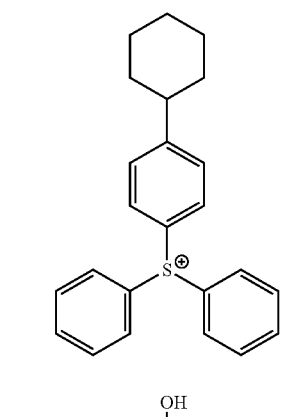
(ca-1-61)
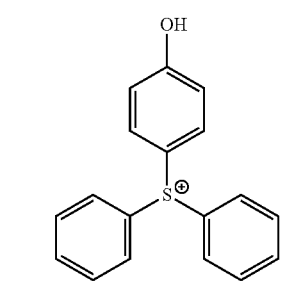
(ca-1-62)
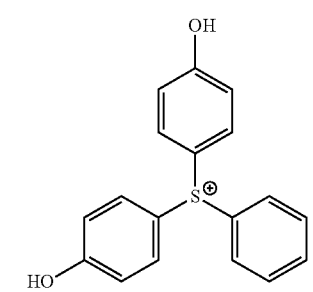
(ca-1-63)
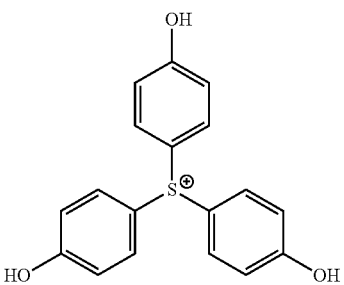
(ca-1-64)
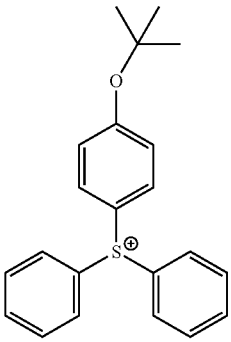
(ca-1-65)
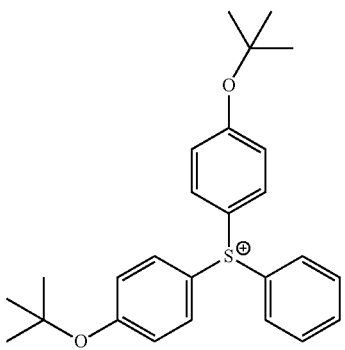
(ca-1-66)
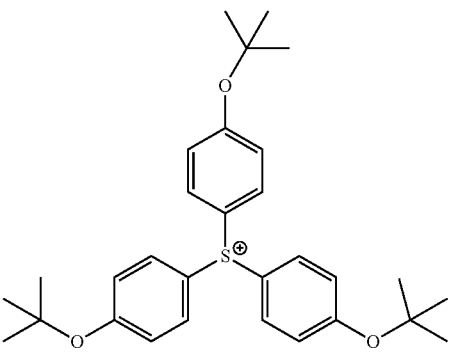
(ca-1-67)
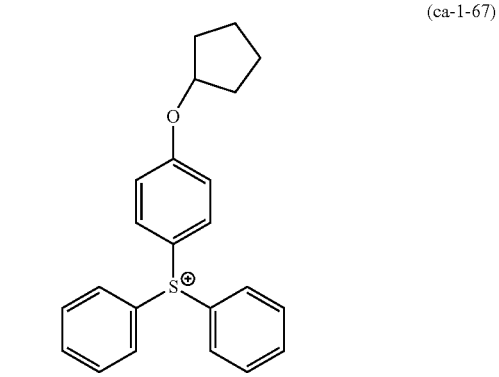

(ca-1-68) 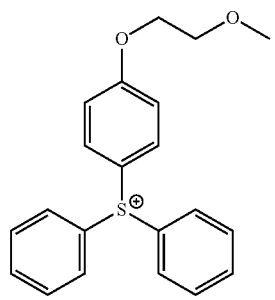
(ca-1-69) 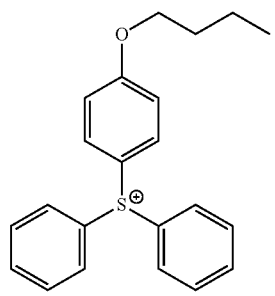
(ca-1-70) 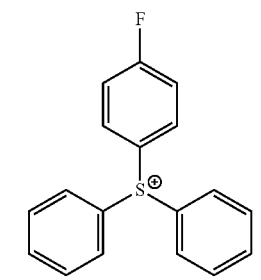
(ca-1-71) 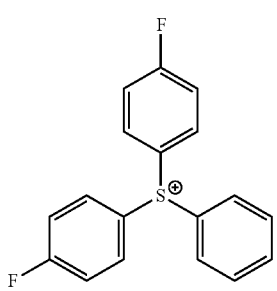
(ca-1-72) 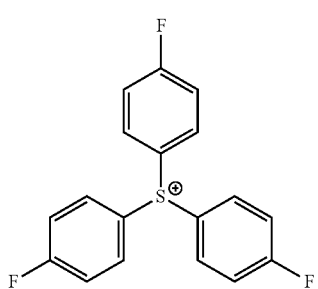
(ca-1-73) 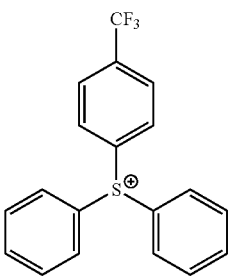
[Chemical Formula 52.]
(ca-1-74) 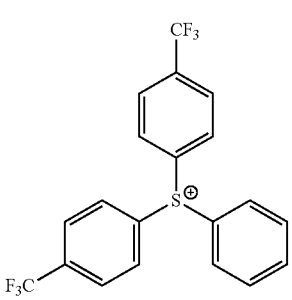
(ca-1-75) 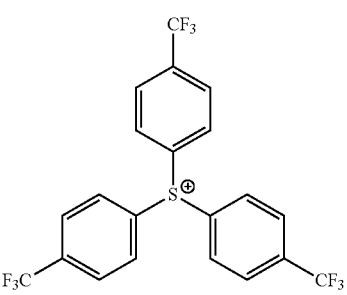
(ca-1-76) 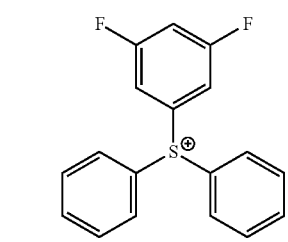
(ca-1-77) 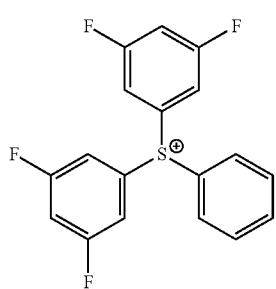

(ca-1-78) 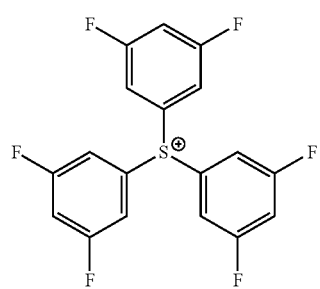
(ca-1-79) 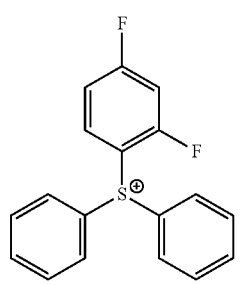
(ca-1-80) 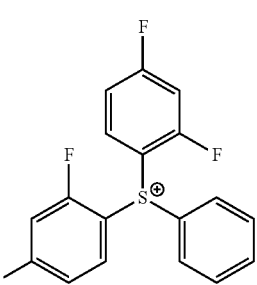
(ca-1-81) 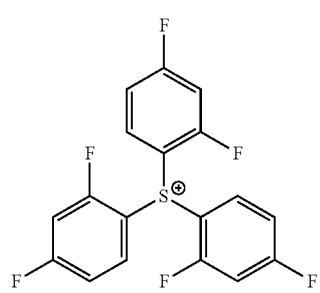
(ca-1-82) 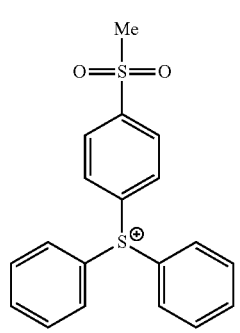
(ca-1-83) 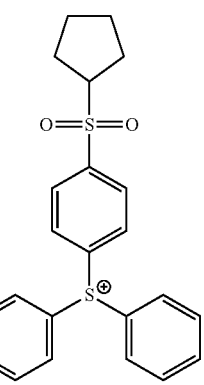
(ca-1-84) 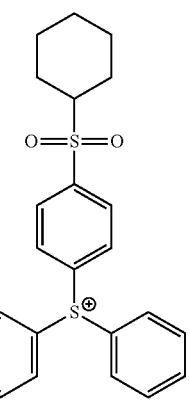
(ca-1-85) 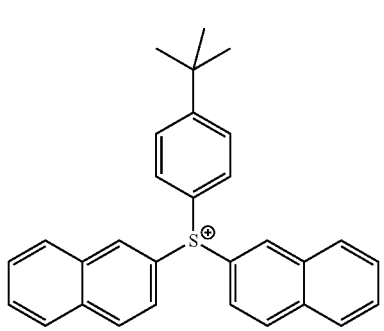
(ca-1-86) 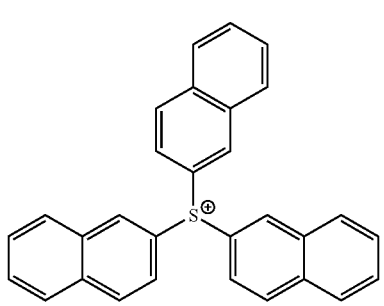

[Chemical Formula 53.]
(ca-1-87)
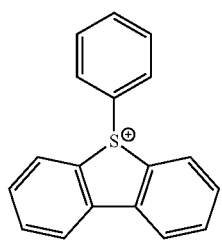
(ca-1-88)
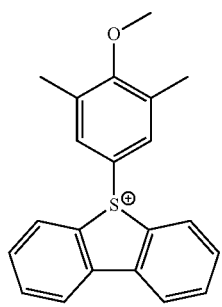
(ca-1-89)
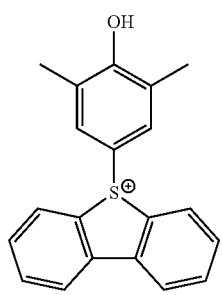
(ca-1-90)
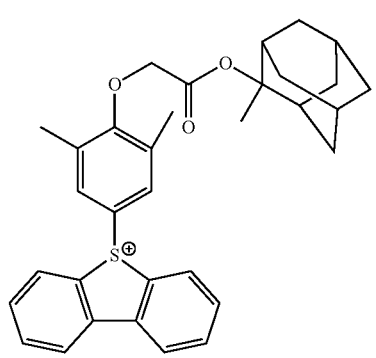
(ca-1-91)
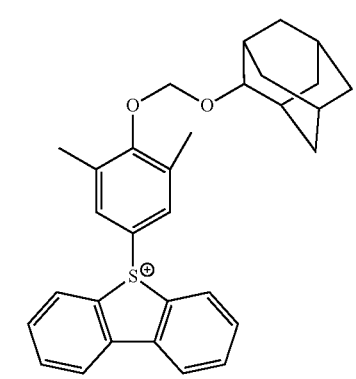
(ca-1-92)
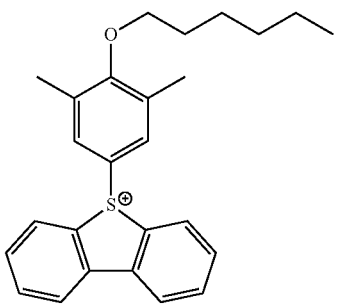
(ca-1-93)
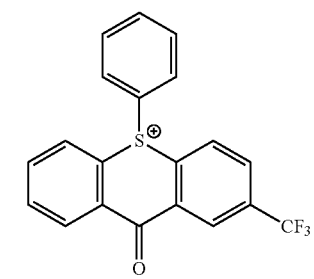
(ca-1-94)
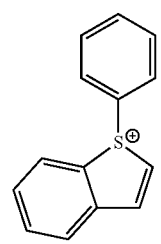
(ca-1-95)
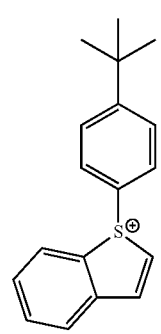
(ca-1-96)
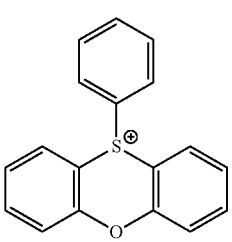

(ca-1-97)
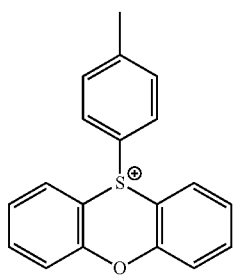
(ca-1-98)
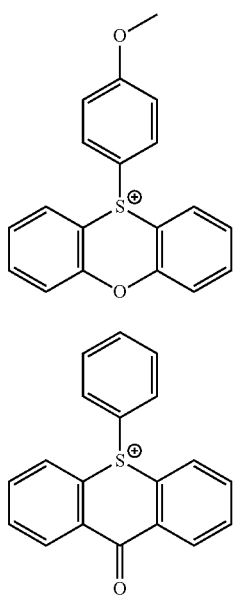
(ca-1-99)
(ca-1-100)
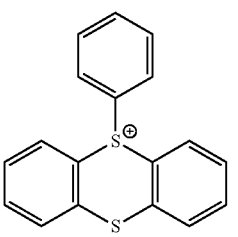
(ca-1-101)
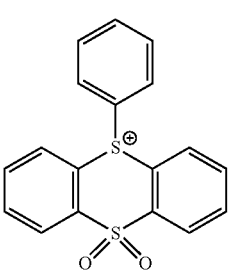
(ca-1-102)
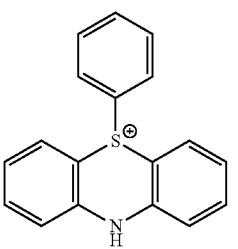
[Chemical Formula 54.]
(ca-1-103)
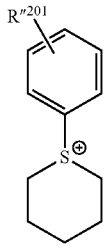
(ca-1-104)
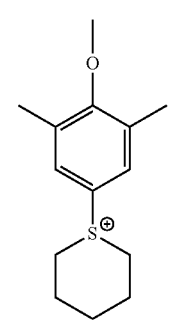
(ca-1-105)
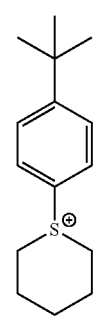
(ca-1-106)
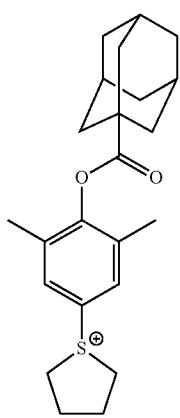

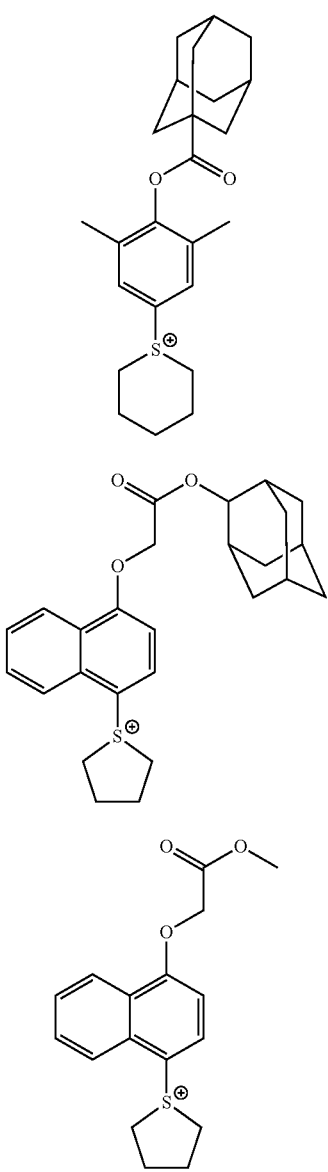 (ca-1-107)
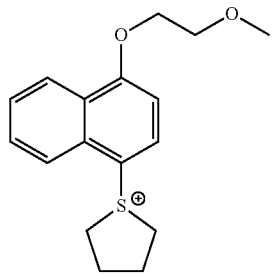 (ca-1-111)
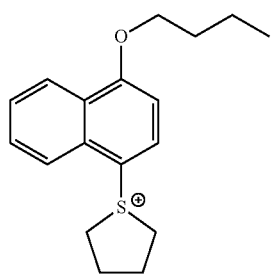 (ca-1-112)
(ca-1-108)
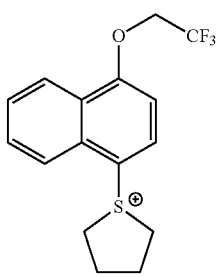 (ca-1-113)
(ca-1-109)
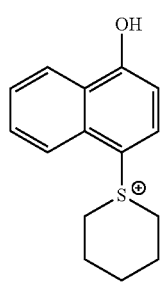 (ca-1-114)
In the formulae, R"²⁰¹ represents a hydrogen atom or a substituent, and as the substituent, the same groups as those described above for substituting $R^{201}$ to $R^{207}$ and $R^{210}$ to $R^{212}$ can be mentioned.
[Chemical Formula 55.]
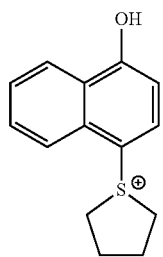 (ca-1-110)
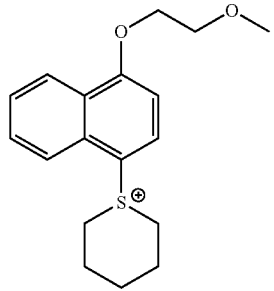 (ca-1-115)

(ca-1-116)
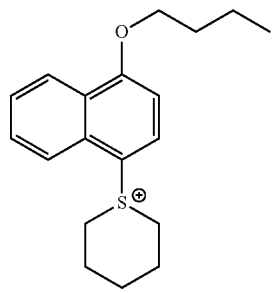
(ca-1-117)
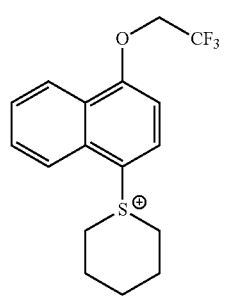
[Chemical Formula 56.]
(ca-1-118)
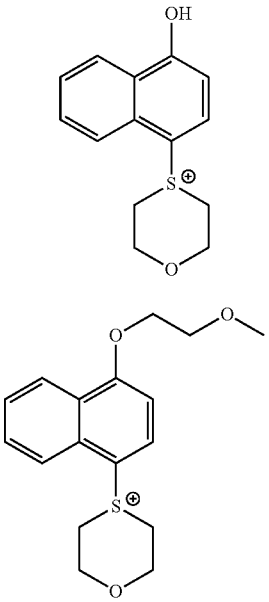
(ca-1-119)
(ca-1-120)
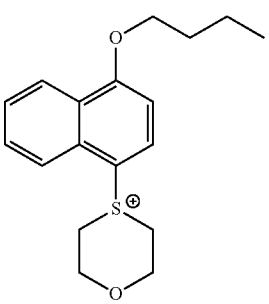
(ca-1-121)
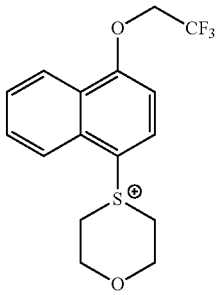
(ca-1-122)
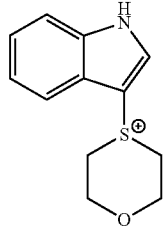
(ca-1-123)
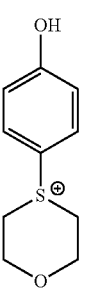
(ca-1-124)
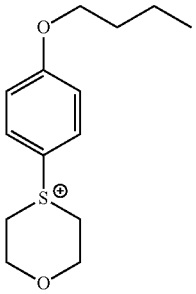
(ca-1-125)
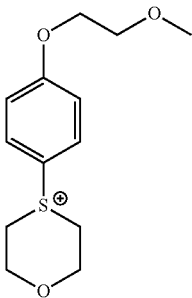

-continued (ca-1-126)

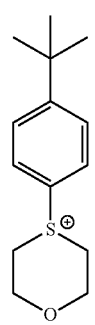

(ca-1-127)

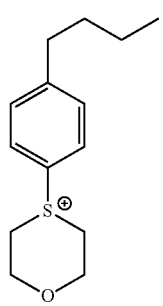

Specific examples of preferable cations represented by the formula (ca-2) include a dihphenyliodonium cation and a bis(4-tert-butylphenyl)iodonium cation.

Specific examples of preferable cations represented by formula (ca-3) include cations represented by formulae (ca-3-1) to (ca-3-6) shown below.

[Chemical Formula 57.]

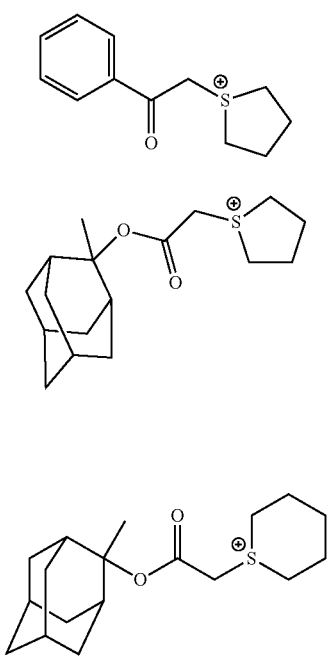

(ca-3-1)

(ca-3-2)

(ca-3-3)

-continued (ca-3-4)

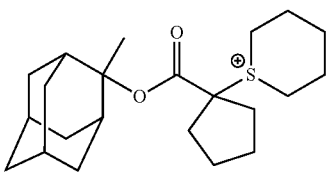

(ca-3-5)

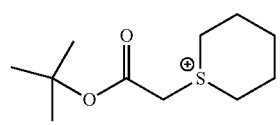

(ca-3-6)

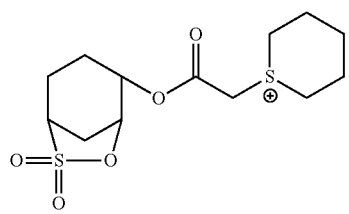

Specific examples of preferable cations represented by formula (ca-4) include cations represented by formulae (ca-4-1) and (ca-4-2) shown below.

[Chemical Formula 58.]

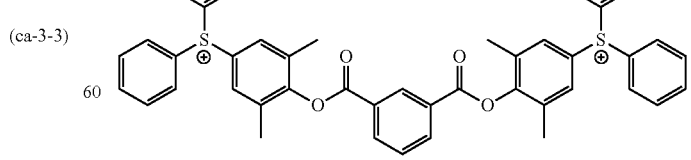

(ca-4-1)

(ca-4-2)

Further, examples of preferable cations represented by formula (ca-5) include cations represented by formulae (ca-5-1) to (ca-5-3) shown below.

[Chemical Formula 59.]
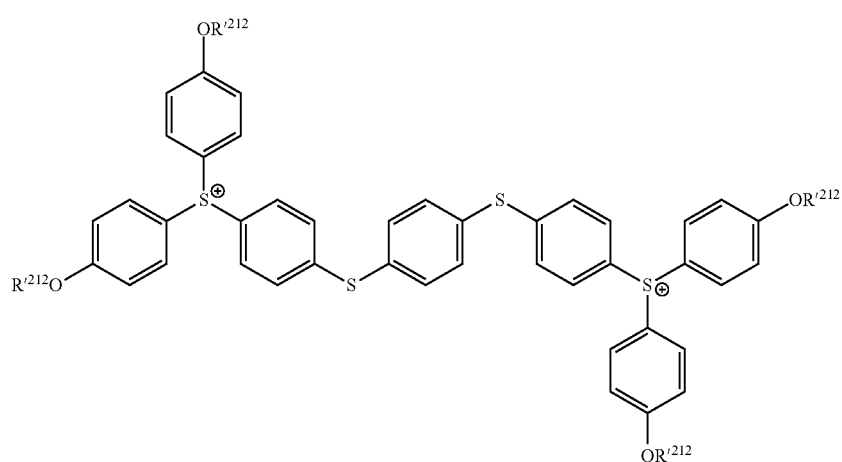
(ca-5-1)
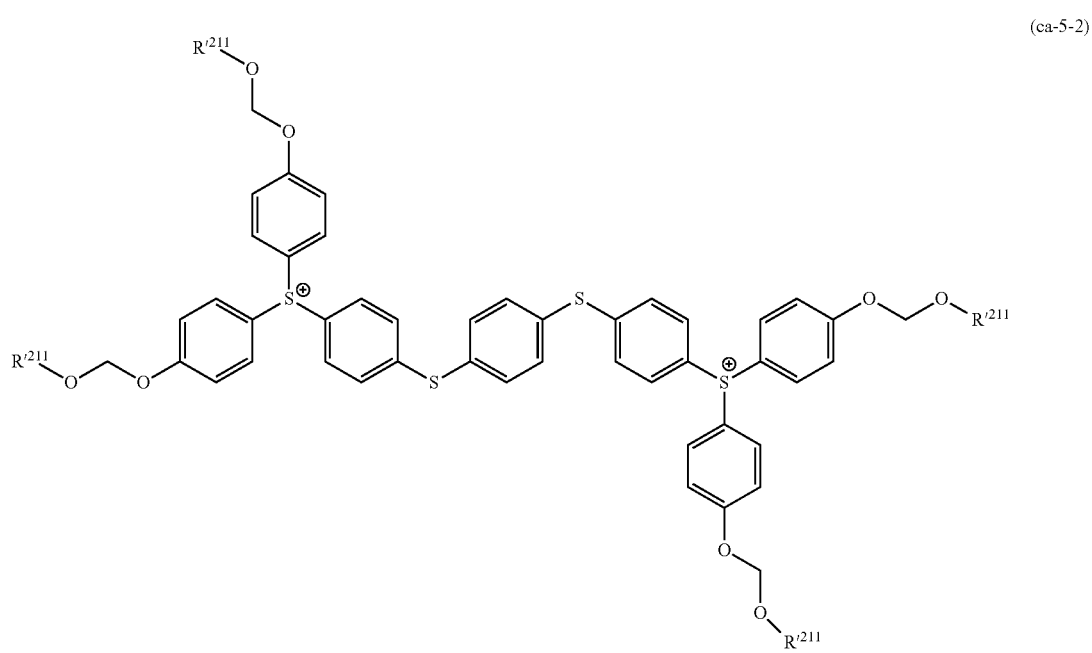
(ca-5-2)
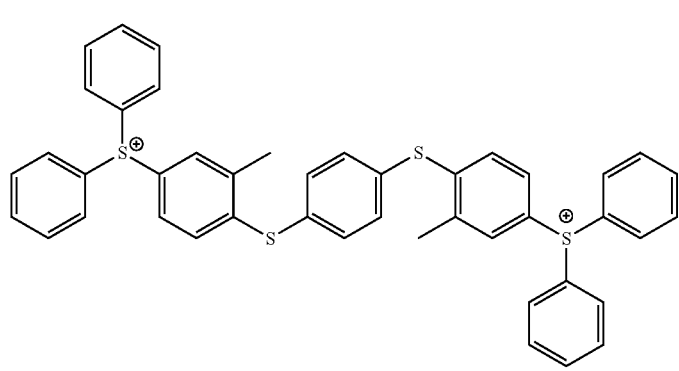
(ca-5-3)

Among the above examples, as the cation moiety [$(M^{m+})_{1/m}$], a cation represented by general formula (ca-1) is preferable, and a cation represented by any one of formulae (ca-1-1) to (ca-1-127) is more preferable.

As the component (B), one type of these acid generators may be used alone, or two or more types may be used in combination.

When the resist composition contains the component (B), the amount of the component (B) relative to 100 parts by weight of the component (A) is preferably within a range from 5 to 50 parts by weight, more preferably from 10 to 40 parts by weight, and still more preferably from 10 to 30 parts by weight.

When the amount of the component (B) is within the above-mentioned range, formation of a resist pattern can be satisfactorily performed. Further, by virtue of the above-mentioned range, when each of the components are dissolved in an organic solvent, a homogeneous solution may be more reliably obtained and the storage stability of the resist composition becomes satisfactory.

<<Acid Diffusion Control Agent (D)>>

The resist composition according to the present embodiment may include an acid diffusion control agent component (hereafter, sometimes referred to as "component (D)"), in addition to the component (A), or in addition to the component (A) and the component (B). The component (D) functions as an acid diffusion control agent, i.e., a quencher which traps the acid generated in the resist composition upon exposure.

The component (D) may be a photodecomposable base (D1) (hereafter, referred to as "component (D1)") which is decomposed upon exposure and then loses the ability of controlling of acid diffusion, or a nitrogen-containing organic compound (D2) (hereafter, referred to as "component (D2)") which does not fall under the definition of component (D1).

Component (D1)

When a resist pattern is formed using a resist composition containing the component (D1), the contrast between exposed portions and unexposed portions of the resist film is improved.

The component (D1) is not particularly limited, as long as it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions of the resist film, the components (d1-1) to (d1-3) are decomposed and then lose the ability of controlling of acid diffusion (i.e., basicity), and therefore the components (d1-1) to (d1-3) cannot function as a quencher, whereas at unexposed portions, the components (d1-1) to (d1-3) functions as a quencher.

[Chemical Formula 60.]

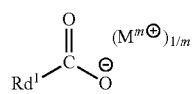

(d1-1)

(d1-2)

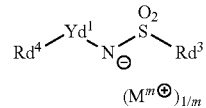

(d1-3)

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) has no fluorine atom bonded thereto; $Yd^1$ represents a single bond or a divalent linking group; m represents an integer of 1 or more; and each $M^{m+}$ independently represents an organic cation having a valency of m.

{Component (d1-1)}

Anion Moiety

In formula (d1-1), $Rd^1$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

Among these, as the group for $Rd^1$, an aromatic hydrocarbon group which may have a substituent, an aliphatic cyclic group which may have a substituent and a chain-like alkyl group which may have a substituent are preferable. Examples of the substituent for these groups include a hydroxy group, an oxo group, an alkyl group, an aryl group, a fluorine atom, a fluorinated alkyl group, a lactone-containing cyclic group represented by any one of the aforementioned formulae (a2-r-1) to (a2-r-7), an ether bond, an ester bond, and a combination thereof. In the case where an ether bond or an ester bond is included as the substituent, the substituent may be bonded via an alkylene group, and a linking group represented by any one of the aforementioned formulae (y-a1-1) to (y-a1-5) is preferable as the substituent.

The aromatic hydrocarbon group is preferably a phenyl group or a naphthyl group.

Examples of the aliphatic cyclic group include groups in which one or more hydrogen atoms have been removed from a polycycloalkane such as adamantane, norbornane, isobornane, tricyclodecane or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine. Examples of the atom other than fluorine include an oxygen atom, a sulfur atom and a nitrogen atom.

As Rd¹, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is particularly desirable.

Specific examples of preferable anion moieties for the component (d1-1) are shown below.

[Chemical Formula 61.]

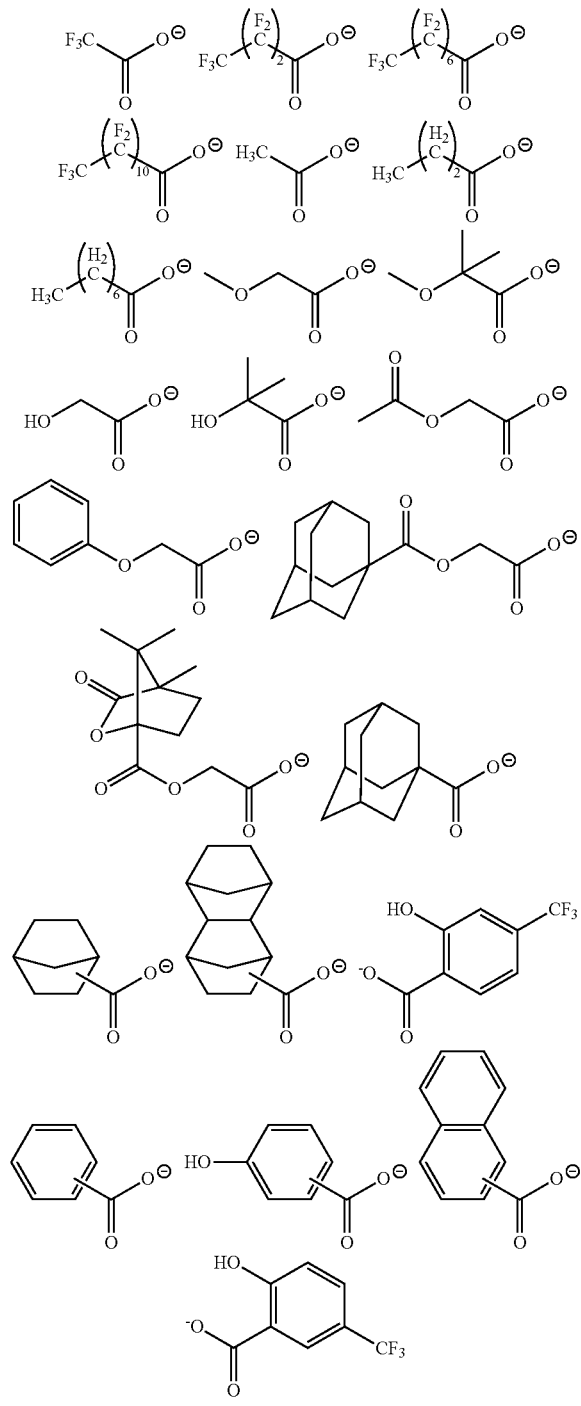

Cation Moiety

In formula (d1-1), $M^{m+}$ represents an organic cation having a valency of m.

As the organic cation for $M^{m+}$, for example, the same cation moieties as those represented by the aforementioned formulae (ca-1) to (ca-5) are preferable, cation moieties represented by the aforementioned general formulae (ca-1) is preferable, and cation moieties represented by the aforementioned formulae (ca-1-1) to (ca-1-127) are still more preferable.

As the component (d1-1), one kind of compound may be used, or two or more kinds of compounds may be used in combination.

{Component (d1-2)}

Anion Moiety

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

Provided that, the carbon atom adjacent to the sulfur atom within $Rd^2$ group has no fluorine atom bonded thereto (i.e., the carbon atom adjacent to the sulfur atom within $Rd^2$ group does not substituted with a fluorine atom). As a result, the anion of the component (d1-2) becomes an appropriately weak acid anion, thereby improving the quenching ability of the component (D).

As $Rd^2$, a chain-like alkyl group which may have a substituent or an aliphatic cyclic group which may have a substituent is preferable. The chain-like alkyl group preferably has 1 to 10 carbon atoms, and more preferably 3 to 10 carbon atoms. As the aliphatic cyclic group, a group in which one or more hydrogen atoms have been removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those described above for substituting the hydrocarbon group (e.g., aromatic hydrocarbon group, aliphatic cyclic group, chain-like alkyl group) for $Rd^1$ in the formula (d1-1) can be mentioned.

Specific examples of preferable anion moieties for the component (d1-2) are shown below.

[Chemical Formula 62.]

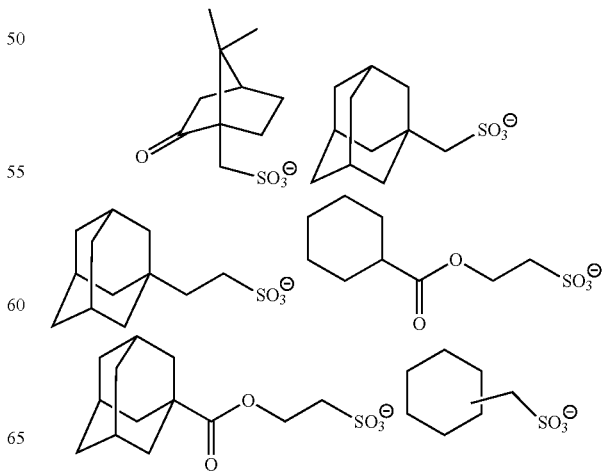

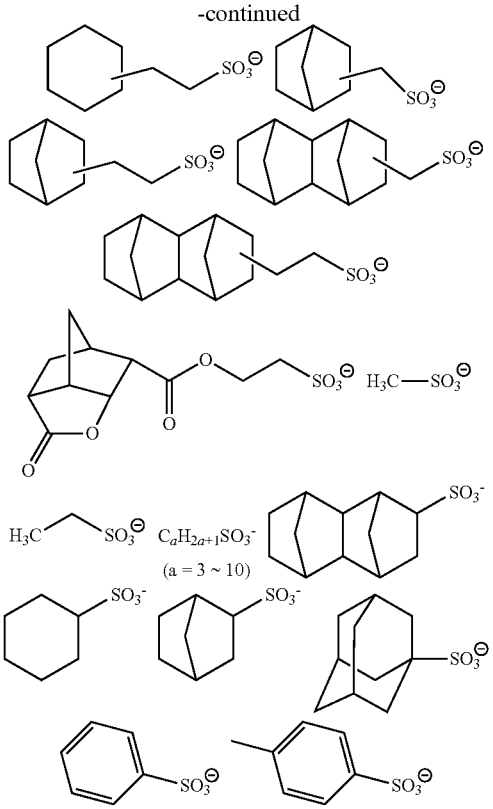

Cation Moiety

In formula (d1-2), $M^{m+}$ is an organic cation having a valency of m, and is the same as defined for $M^{m+}$ in the aforementioned formula (d1-1).

As the component (d1-2), one type of compound may be used, or two or more types of compounds may be used in combination.

{Component (d1-3)}
Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$ in the aforementioned formula (b-1), and a cyclic group containing a fluorine atom, a chain-like alkyl group or a chain-like alkenyl group is preferable. Among these, a fluorinated alkyl group is preferable, and more preferably the same fluorinated alkyl groups as those described above for $Rd^1$.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group having 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group having 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ in the aforementioned formula (b-1) can be mentioned, and a vinyl group, a propenyl group (an allyl group), a 1-methylpropenyl group and a 2-methylpropenyl group are preferable. These groups may have an alkyl group having 1 to 5 carbon atoms or a halogenated alkyl group having 1 to 5 carbon atoms as a substituent.

As the cyclic group for $Rd^4$, the same groups as those described above for $R^{101}$ in the aforementioned formula (b-1) can be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithography properties. Alternatively, when $Rd^4$ is an aromatic group, the resist composition exhibits an excellent photoabsorption efficiency in a lithography process using EUV or the like as the exposure source, thereby resulting in the improvement of the sensitivity and the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. The divalent linking groups are the same as defined for the divalent hydrocarbon group which may have a substituent and the divalent linking group containing a hetero atom explained above as the divalent linking group for $Ya^{21}$ in the aforementioned formula (a2-1).

As $Yd^1$, a carbonyl group, an ester bond, an amide bond, an alkylene group or a combination of these is preferable. As the alkylene group, a linear or branched alkylene group is more preferable, and a methylene group or an ethylene group is still more preferable.

Specific examples of preferable anion moieties for the component (d1-3) are shown below.

[Chemical Formula 63.]

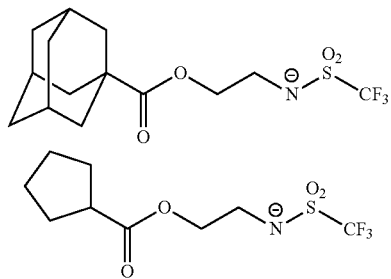

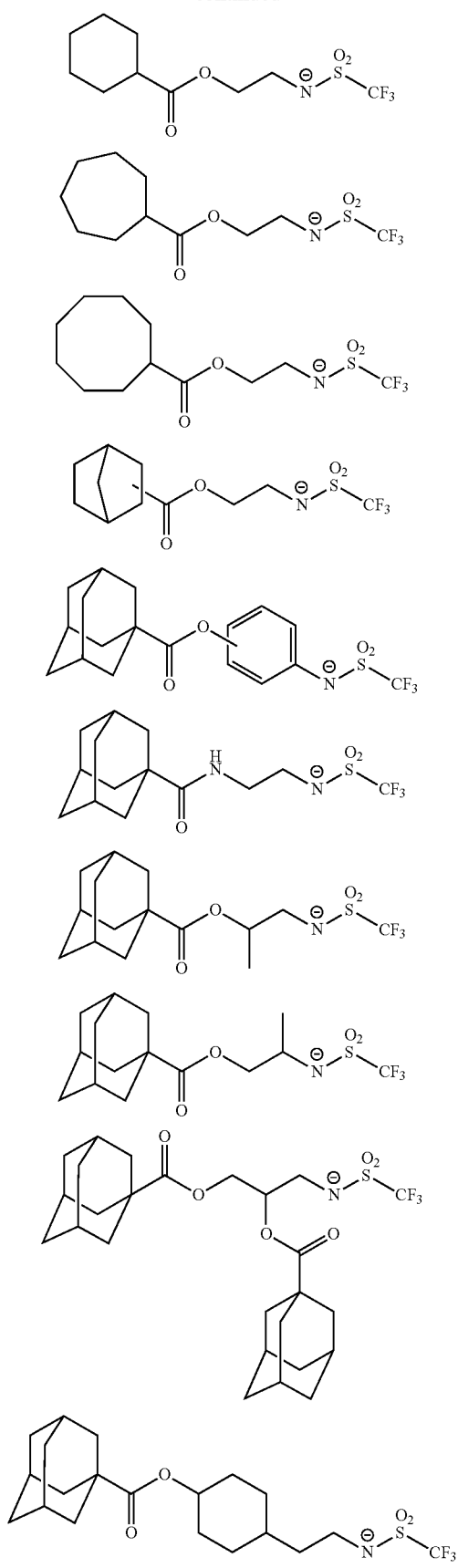
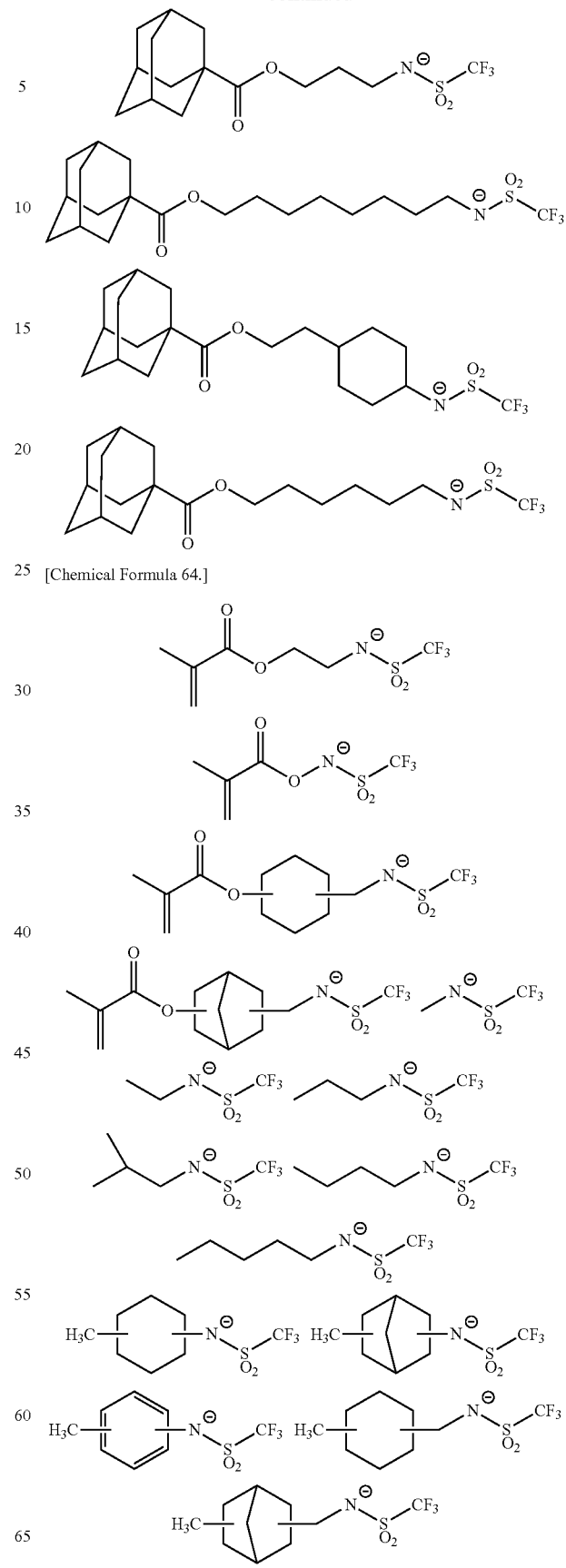
[Chemical Formula 64.]

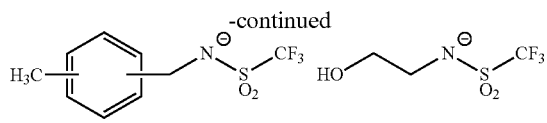

Cation Moiety

In formula (d1-3), $M^{m+}$ is an organic cation having a valency of m, and is the same as defined for $M^{m+}$ in the aforementioned formula (d1-1).

As the component (d1-3), one type of compound may be used, or two or more types of compounds may be used in combination.

As the component (D1), one type of the aforementioned components (d1-1) to (d1-3), or at least two types of the aforementioned components (d1-1) to (d1-3) can be used in combination.

When the resist composition contains the component (D1), the amount of the component (D1) relative to 100 parts by weight of the component (A) is preferably within a range from 0.5 to 10 parts by weight, more preferably from 0.5 to 8 parts by weight, and still more preferably from 1 to 8 parts by weight.

When the amount of the component (D1) is at least as large as the lower limit of the above-mentioned range, excellent lithography properties and excellent resist pattern shape can be more reliably obtained. On the other hand, when the amount of the component (D1) is no more than the upper limit of the above-mentioned range, sensitivity can be maintained at a satisfactory level, and through-put becomes excellent.

Production Method of Component (D1):

The production methods of the components (d1-1) and (d1-2) are not particularly limited, and the components (d1-1) and (d1-2) can be produced by conventional methods.

Further, the production method of the component (d1-3) is not particularly limited, and the component (d1-3) can be produced in the same manner as disclosed in US2012-0149916.

Component (D2)

The acid diffusion control component may contain a nitrogen-containing organic compound (D2) (hereafter, referred to as component (D2)) which does not fall under the definition of component (D1).

The component (D2) is not particularly limited, as long as it functions as an acid diffusion control agent, and does not fall under the definition of the component (D1). As the component (D2), any of the conventionally known compounds may be selected for use. Among these, an aliphatic amine is preferable, and a secondary aliphatic amine or tertiary aliphatic amine is more preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group having no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include 4-dimethylaminopyridine, pyrrole, indole, pyrazole, imidazole and derivatives thereof, as well as tribenzylamine, 2,6-diisopropylaniline and N-tert-butoxycarbonylpyrrolidine.

As the component (D2), one type of compound may be used alone, or two or more types may be used in combination.

When the resist composition contains the component (D2), the amount of the component (D2) is typically used in an amount within a range from 0.01 to 5 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

<<At Least One Compound (E) Selected from the Group Consisting of an Organic Carboxylic Acid, or a Phosphorus Oxo Acid or Derivative Thereof>>

In the resist composition of the present embodiment, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof may be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group having 1 to 5 carbon atoms and an aryl group having 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one type may be used alone, or two or more types may be used in combination.

When the resist composition contains the component (E), the amount of the component (E) is typically used in an amount within a range from 0.01 to 5 parts by weight, relative to 100 parts by weight of the component (A).

<<Fluorine Additive (F)>>

In the present embodiment, the resist composition may further include a fluorine additive (hereafter, referred to as "component (F)") for imparting water repellency to the resist film.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of the structural unit (f1) and a structural unit (a1) containing an acid decomposable group that exhibits increased polarity by the action of acid; and a copolymer of the structural unit (f1), a structural unit derived from acrylic acid or methacrylic acid and the structural unit (a1) are preferable. As the structural unit (a1) to be copolymerized with the structural unit (f1), a structural unit derived from 1-ethyl-1-cyclooctyl (meth)acrylate or a structural unit derived from 1-methyl-1-adamantyl (meth)acrylate is preferable.

[Chemical Formula 65.]

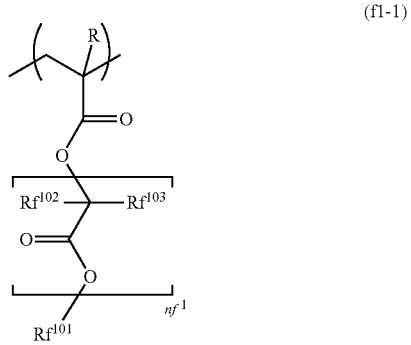

(f1-1)

In the formula, R is the same as defined above; $Rf^{102}$ and $Rf^{103}$ each independently represents a hydrogen atom, a halogen atom, an alkyl group having 1 to 5 carbon atoms, or a halogenated alkyl group having 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R bonded to the carbon atom on the α-position is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly desirable. Examples of the alkyl group having 1 to 5 carbon atoms for $Rf^{102}$ and $Rf^{103}$ include the same alkyl group having 1 to 5 carbon atoms as those described above for R, and a methyl group or an ethyl group is preferable. Specific examples of the halogenated alkyl group having 1 to 5 carbon atoms represented by $Rf^{102}$ or $Rf^{103}$ include groups in which part or all of the hydrogen atoms of the aforementioned alkyl groups of 1 to 5 carbon atoms have been substituted with halogen atoms.

Examples of the halogen atom include a fluorine atom, a chlorine atom, a bromine atom and an iodine atom, and a fluorine atom is particularly desirable. Among these examples, as $Rf^{102}$ and $Rf^{103}$, a hydrogen atom, a fluorine atom or an alkyl group having 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group having 1 to 6 carbon atoms is preferable, and a trifluoromethyl group, —$CH_2$—$CF_3$, —$CH_2$—$CF_2$—$CF_3$, —$CH(CF_3)_2$, —$CH_2$—$CH_2$—$CF_3$, and —$CH_2$—$CH_2$—$CF_2$—$CF_2$—$CF_2$—$CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the Mw of the component (F) is no more than the upper limit of the above-mentioned range, the resist composition exhibits a satisfactory solubility in a resist solvent. On the other hand, when the Mw is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one type may be used alone, or two or more types may be used in combination.

When the resist composition contains the component (F), the component (F) is used in an amount within a range from 0.5 to 10 parts by weight, relative to 100 parts by weight of the component (A).

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

<<Organic Solvent (S)>>

The resist composition of the present embodiment may be prepared by dissolving the resist materials for the resist composition in an organic solvent (hereafter, referred to as "component (S)").

The component (S) may be any organic solvent which can dissolve the respective components to give a homogeneous solution, and any organic solvent can be appropriately selected from those which have been conventionally known as solvents for a chemically amplified resist composition.

Examples of the component (S) include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

The component (S) can be used individually, or in combination as a mixed solvent.

Among these, PGMEA, PGME, γ-butyrolactone, EL and cyclohexanone are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3. Furthermore, a mixed solvent of PGMEA, PGME and cyclohexanone is also preferable.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate. In general, the component (S) is used in an amount such that the solid content of the resist composition becomes within the range from 1 to 20% by weight, and preferably from 2 to 15% by weight.

As described above, the resist composition of the present embodiment employs a resin component (A1) including a structural unit having a specific structure, namely, a structural unit (a0) derived from a compound represented by general formula (a0-1). In the resin component (A1), the tertiary carbon-containing group containing the 3-membered ring is dissociated by the action of acid, and the polarity is changed. Therefore, the efficiency of the reaction caused by the action of acid is improved, and the solubility in a developing solution is improved during developing, such that a fine development contrast may be reliably obtained.

Thus, by the resist composition of the present embodiment, sensitivity can be enhanced in the formation of a resist pattern, and it becomes possible to form a resist pattern exhibiting excellent lithography properties (resolution, reduction of roughness, and the like).

Furthermore, in the resist composition of the present embodiment, by using a resin component (A1) having a structural unit (a0) and a structural unit (a10), particularly in the formation of a resist pattern using EUV (extreme ultraviolet) or EB (electron beam) as an exposure source, both high sensitivity and excellent lithography properties (resolution, reduction of roughness, and the like) can be satisfied.

(Method of Forming a Resist Pattern)

The method of forming a resist pattern according to the present embodiment includes: forming a resist film on a substrate using a resist composition of the aforementioned embodiment; conducting exposure of the resist film; and developing the resist film to form a resist pattern.

The method for forming a resist pattern according to the present embodiment can be performed, for example, as follows.

Firstly, a resist composition of the first aspect is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such an ArF exposure apparatus, an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment. The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing.

In this manner, a resist pattern can be formed.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition is effective to KrF excimer laser, ArF excimer laser, EB and EUV, and more effective to ArF excimer laser, EB and EUV, and most effective to EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the component (A) (prior to exposure). Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C(=O)—C within the structure thereof. An ester solvent is an organic solvent containing C—C(=O)—O—C within the structure thereof. An alcohol solvent is an organic solvent containing an alcoholic hydroxy group in the structure thereof. An "alcoholic hydroxy group" refers to a hydroxy group bonded to a carbon atom of an aliphatic hydrocarbon group. A nitrile solvent is an organic solvent containing a nitrile group in the structure thereof. An amide solvent is an organic solvent containing an amide group within the structure thereof. An ether solvent is an organic solvent containing C—O—C within the structure thereof.

Some organic solvents have a plurality of the functional groups which characterizes the aforementioned solvents within the structure thereof. In such a case, the organic solvent can be classified as any type of the solvent having the characteristic functional group. For example, diethyleneglycol monomethylether can be classified as either an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

As the organic solvent contained in the organic developing solution, among these, a polar solvent is preferable, and ketone solvents, ester solvents and nitrile solvents are preferable.

Examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, γ-butyrolactone and methyl amyl ketone (2-heptanone). Among these examples, as a ketone solvent, methyl amyl ketone (2-heptanone) is preferable.

Examples of ester solvents include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate and propyl-3-methoxypropionate. Among these examples, as an ester solvent, butyl acetate is preferable.

Examples of nitrile solvents include acetonitrile, propionitrile, valeronitrile, butyronitrile and the like.

If desired, the organic developing solution may have a conventional additive blended. Examples of the additive include surfactants. The surfactant is not particularly limited, and for example, an ionic or non-ionic fluorine and/or silicon surfactant can be used.

As the surfactant, a non-ionic surfactant is preferable, and a non-ionic fluorine surfactant or a non-ionic silicon surfactant is more preferable.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol and benzyl alcohol. Among these, 1-hexanol, 2-heptanol and 2-hexanol are preferable, and 1 hexanol and 2-hexanol are more preferable.

As the organic solvent, one kind of solvent may be used alone, or two or more kinds of solvents may be used in combination. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and most preferably 3% by weight or less.

If desired, the rinse solution may have a conventional additive blended. Examples of the additive include surfactants. Examples of the additive include surfactants. As the surfactant, the same surfactants as those described above can be mentioned, a non-ionic surfactant is preferable, and a non-ionic fluorine surfactant or a non-ionic silicon surfactant is more preferable.

When a surfactant is added, the amount thereof based on the total amount of the rinse liquid is generally 0.001 to 5% by weight, preferably 0.005 to 2% by weight, and more preferably 0.01 to 0.5% by weight.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

In the method of forming a resist pattern according to the present embodiment, since the resist composition according to the first embodiment described above is used, high sensitivity can be maintained in the formation of a resist pattern. In addition, by the method of forming a resist pattern according to the present embodiment, lithography properties (resolution, reduction of roughness, and the like) can be improved, and resolution can be enhanced. As a result, it becomes possible to form a resist pattern having a good shape.

(Polymeric Compound)

The polymeric compound of the present embodiment has a structural unit (a0) derived from a compound represented by general formula (a0-1) shown below.

[Chemical Formula 66.]

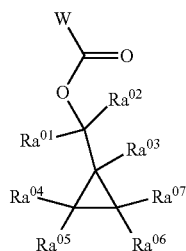

(a0-1)

In the formula, W represents a polymerizable group-containing group; $Ra^{o1}$ is a group which is bonded to $Ra^{o3}$ to form an aliphatic cyclic group together with the carbon atom to which $Ra^{o3}$ is bonded and the carbon atom to which $Ra^{o1}$ is bonded, or a group which is bonded to $Ra^{o4}$ to form an aliphatic cyclic group together with the carbon atom to which $Ra^{o4}$ is bonded, the carbon atom to which $Ra^{o3}$ is bonded and the carbon atom to which $Ra^{o1}$ is bonded; $Ra^{o2}$ represents a hydrocarbon group which may have a substituent; $Ra^{o3}$ is a hydrogen atom or a monovalent organic group in the case where $Ra^{o1}$ is not bonded thereto; $Ra^{o4}$ is a hydrogen atom or a monovalent organic group in the case where $Ra^{o1}$ is not bonded thereto; and $Ra^{o5}$ to $Ra^{o7}$ each independently represents a hydrogen atom or a monovalent organic group.

In the case where the polymeric compound of the present embodiment is applied to, for example, a base resin for a resist composition, the amount of the structural unit (a0) based on the combined total of all structural units constituting the polymeric compound is preferably 20 to 80 mol %, more preferably 30 to 75 mol %, and still more preferably 40 to 70 mol %.

The polymeric compound according to the present embodiment is the same as defined for the component (A1) (polymeric compound including a structural unit (a0)) described above under "(Resist composition)", and the kind of each structural unit other than the structural unit (a0), the amount of each structural unit and the like are the same as defined above for the component (A1).

The polymeric compound of the present embodiment may be produced, for example, dissolving a monomer which derives a structural unit (a0) (a compound represented by general formula (a0-1)) and, if desired, a monomer which derives a structural unit other than the structural unit (a0) in a polymerization solvent, followed by adding a radical polymerization initiator such as azobisisobutyronitrile (AIBN) or dimethyl 2,2'-azobis(isobutyrate) (e.g., V-601) to effect a polymerization reaction. Alternatively, the polymeric compound of the present embodiment may be produced by dissolving a monomer which derives a structural unit (a0) (a compound represented by general formula (a0-1)) and, if desired, a precursor of a monomer which derives a structural unit other than the structural unit (a0) in a polymerization solvent, followed by adding a radical polymerization initiator to effect a polymerization reaction, and then conducting a deprotection reaction.

In the polymerization, a chain transfer agent such as $HS-CH_2-CH_2-CH_2-C(CF_3)_2-OH$ may be used to introduce a $-C(CF_3)_2-OH$ group at the terminal(s) of the polymer. Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The polymeric compound according to the present embodiment is a novel substance useful as a base resin for a resist composition. The polymeric compound may be preferably added to a resist composition as a base component having a film forming ability, and also as a resin component (component (A1)) which exhibits changed solubility in a developing solution by the action of acid.

(Compound)

The compound of the present embodiment is represented by general formula (a0-1) shown below (hereafter, referred to as "compound (a00)").

[Chemical Formula 67.]

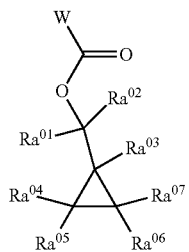

(a0-1)

In the formula, W represents a polymerizable group-containing group; $Ra^{o1}$ is a group which is bonded to $Ra^{o3}$ to form an aliphatic cyclic group together with the carbon atom to which $Ra^{o3}$ is bonded and the carbon atom to which $Ra^{o1}$ is bonded, or a group which is bonded to $Ra^{o4}$ to form an aliphatic cyclic group together with the carbon atom to which $Ra^{o4}$ is bonded, the carbon atom to which $Ra^{o3}$ is bonded and the carbon atom to which $Ra^{o1}$ is bonded; $Ra^{o2}$ represents a hydrocarbon group which may have a substituent; $Ra^{o3}$ is a hydrogen atom or a monovalent organic group in the case where $Ra^{o1}$ is not bonded thereto; $Ra^{o4}$ is a hydrogen atom or a monovalent organic group in the case where $Ra^{o1}$ is not bonded thereto; and $Ra^{o5}$ to $Ra^{o7}$ each independently represents a hydrogen atom or a monovalent organic group.

The compound according to the present embodiment is the same as the monomer which derives the structural unit (a0) described above in relation to the resist composition of the first aspect.

(Production Method of Compound (a00))

The compound (a00) may be produced by a conventional method. As the production method of the compound (a00), for example, a method including the following steps (i) and (ii) may be mentioned.

As the compounds used in each step, commercially available compounds may be used, or the compounds may be synthesized by a conventional method.

The organic solvent used in each step may be any solvent which is capable of dissolving compounds used in each step and does not react with the compounds. Examples of the organic solvent include dichloromethane, dichloroethane, chloroform, tetrahydrofuran (THF), N,N-dimethylformamide, dimethylacetamide, dimethylsulfoxide, acetonitrile and acetone.

[Chemical Formula 68.]

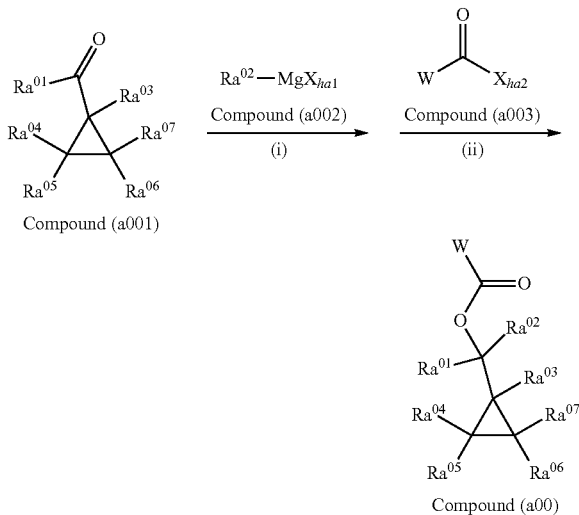

In the formula, W and $Ra^{01}$ to $Ra^{07}$ are the same as defined for W and $Ra^{01}$ to $Ra^{07}$ in the aforementioned formula (a0-1), respectively; and $X_{ha1}$ and $X_{ha2}$ each independently represents a halogen atom.

Step (i):

In step (i), for example, a compound (a001) is dissolved in an organic solvent, and a solution obtained by dissolving a compound (a002) in an organic solvent is dropwise added to the solution of the compound (a001) to effect a reaction.

The reaction temperature is preferably −80 to 40° C., more preferably −40 to 20° C. The reaction time varies, depending on the reactivity of the compound (a001) and the compound (a002), the reaction temperature, and the like. However, in general, the reaction time is preferably 10 minutes to 12 hours, more preferably 30 minutes to 6 hours.

The compound (a002) is the so-called Grignard reagent. Examples of $X_{ha1}$ (halogen atom) include a fluorine atom, a chlorine atom, a bromine atom and an iodine atom. As $X_{ha1}$, a bromine atom is preferable.

In the case where the compound (a001) is synthesized by a conventional method, the compound (a001) may be obtained, for example, by reacting a 2-cycloalkenone or a cycloalkanone-2-ylidene with trimethylsulfoxonium iodide in the presence of a strong base.

Examples of the strong base include an organic alkali metal, such as n-butyllithium, s-butyllithium, t-butyllithium, ethyllithium, ethylsodium, 1,1-diphenylhexyllithium, or 1,1-diphenyl-3-methylpentyllithium; and sodium hydride.

Step (ii):

In step (ii), for example, a solution obtained by dissolving a compound (a003) in an organic solvent is dropwise added to the reaction liquid obtained in step (i), so as to obtain the objective compound (a00).

The reaction temperature is preferably −20 to 50° C., more preferably −10 to 40° C. The reaction time varies, depending on the reactivity of the reaction liquid obtained in step (i) and the compound (a003), the reaction temperature, and the like. However, in general, the reaction time is preferably 10 minutes to 24 hours, more preferably 30 minutes to 12 hours.

In the compound (a003), examples of $X_{ha2}$ include a fluorine atom, a chlorine atom, a bromine atom and an iodine atom, and a chlorine atom is preferable.

After the reaction, the compound (a00) within the reaction mixture may be separated and purified.

The separation and purification can be conducted by a conventional method. For example, any one or more of concentration, solvent extraction, distillation, crystallization, re-crystallization and chromatography may be used.

The structure of the compound (a00) obtained in the manner described above may be confirmed by a general organic analysis method such as $^1$-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

EXAMPLES

As follows is a description of examples of the present invention, although the scope of the present invention is by no way limited by these examples.

<Production Example of Intermediate>

Intermediate (m1), intermediate (m2), intermediate (m3), intermediate (m4), intermediate (m5) and intermediate (m6) were produced as follows.

<<Intermediate (m1)>>

26.8 g of sodium hydride (purity: 60%) was suspended in 500 g of dimethylsulfoxide, and 147 g of trimethylsulfoxonium iodide was added thereto in small amounts, followed by stirring at 20° C. for 1 hour. Then, 50.0 g of 2-cyclopentenone was dropwise added to the resultant, followed by stirring at room temperature for 30 minutes, and then stirring at 50° C. for 2 hours. Subsequently, the reaction liquid was cooled to room temperature, and 500 g of ice water was added thereto, followed by removing the precipitate by filtration. 500 g of methyl tert-butyl ether (MTBE) was added to the filtrate, followed by stirring for 30 minutes and then removing the aqueous phase. Thereafter, the solvent of the organic phase was removed by distillation, followed by further purification by distillation, so as to obtain intermediate (m1) (42.1 g, yield: 72.1%).

[Chemical Formula 69.]

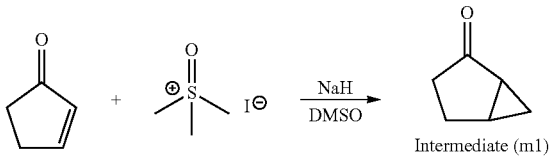

<<Intermediate (m2)>>

The same method as in the synthesis example of intermediate (m1) was conducted, except that 50.0 g of 2-cyclopentenone was changed to 58.5 g of 2-methyl-2-cyclopentenone, so as to obtain intermediate (m2) (55.4 g, yield: 37.2%).

[Chemical Formula 70.]

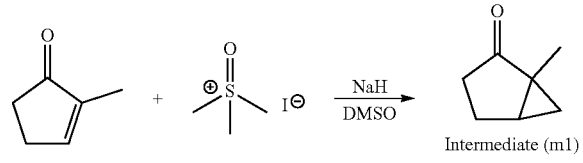

<<Intermediate (m3)>>

The same method as in the synthesis example of intermediate (m1) was conducted, except that 50.0 g of 2-cyclopentenone was changed to 58.5 g of 2-cyclohexenone, so as to obtain intermediate (m3) (46.3 g, yield: 69.0%).

[Chemical Formula 71.]

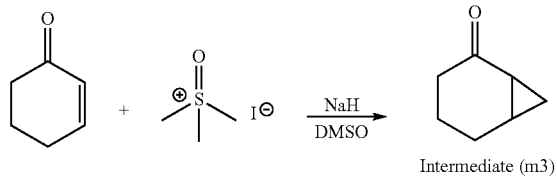

Intermediate (m3)

<<Intermediate (m4)>>

The same method as in the synthesis example of intermediate (m1) was conducted, except that 50.0 g of 2-cyclopentenone was changed to 67.1 g of 2-cycloheptenone, so as to obtain intermediate (m4) (34.5 g, yield: 45.6%).

[Chemical Formula 72.]

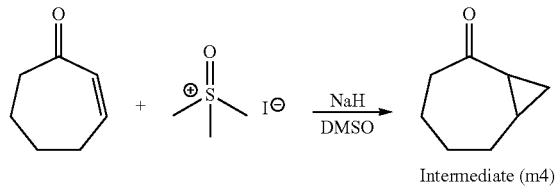

Intermediate (m4)

<<Intermediate (m5)>>

The same method as in the synthesis example of intermediate (m1) was conducted, except that 50.0 g of 2-cyclopentenone was changed to 58.5 g of cyclopentanone-2-ylidene, so as to obtain intermediate (m5) (44.3 g, yield: 66.1%).

[Chemical Formula 73.]

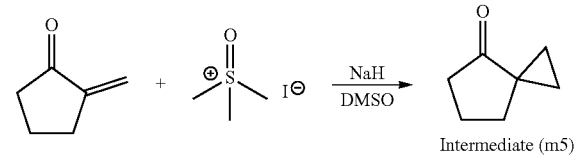

Intermediate (m5)

<<Intermediate (m6)>>

The same method as in the synthesis example of intermediate (m1) was conducted, except that 50.0 g of 2-cyclopentenone was changed to 67.1 g of cyclohexanone-2-ylidene, so as to obtain intermediate (m6) (44.0 g, yield: 58.1%).

[Chemical Formula 74.]

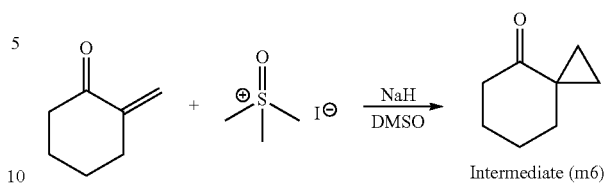

Intermediate (m6)

<Production Example of Monomer>

Monomer (a01), monomer (a02), monomer (a03), monomer (a04), monomer (a05), monomer (a06), monomer (a07) and monomer (a08) were produced as follows.

<<Monomer (a01)>>

30.0 g of intermediate (m1) was dissolved in 90 g of tetrahydrofuran (THF), and 343 ml of methylmagnesium bromide (THF solution, 1.0 mol/l) was dropwise added to the obtained solution at a temperature of −20° C. or lower, followed by stirring for 1 hour. Then, a solution obtained by dissolving 35.9 g of methacrylic acid chloride in 71.8 g of THF was dropwise added to the resultant. After further stirring for 1 hour while cooling with ice, 300 g of pure water was dropwise added to the reaction liquid, followed by extraction with 300 g of heptane. Thereafter, the solvent of the organic phase was removed by distillation, followed by further purification by distillation, so as to obtain monomer (a01) (49.7 g, yield: 88.4%).

[Chemical Formula 75.]

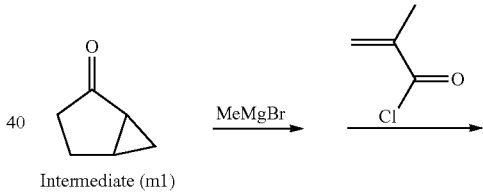

Intermediate (m1)

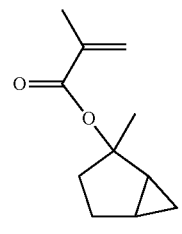

Monomer (a01)

The obtained monomer (a01) was analyzed by NMR, and the structure thereof was identified by the following results.

δ(ppm)=6.05-6.06 (s, C=CH, 1H), 5.74-5.75 (m, C=CH, 1H), 1.86-1.88 (s, $CH_3$, 3H), 1.72-1.86 (m, $CH_2CH_2$, 4H), 1.57-1.59 (s, $CH_3$, 3H), 1.32-1.38 (m, CH, CH, 2H), 0.44-0.50 (m, $CH_2$, 2H)

<<Monomer (a02)>>

The same method as in the synthesis example of monomer (a01) was conducted, except that 343 ml of methylmagnesium bromide (THF solution, 1.0 mol/l) was changed to 343 ml of ethylmagnesium bromide (THF solution, 1.0 mol/l), so as to obtain monomer (a02) (41.9 g, yield: 69.1%).

[Chemical Formula 76.]

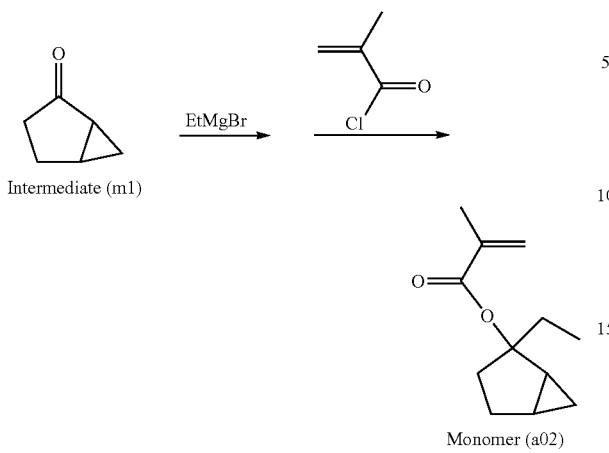

The obtained monomer (a02) was analyzed by NMR, and the structure thereof was identified by the following results.

δ(ppm)=6.05-6.06 (s, C=CH, 1H), 5.74-5.75 (m, C=CH, 1H), 1.86-1.88 (s, CH$_3$, 3H), 1.72-1.86 (m, CH$_2$CH$_2$, CH$_2$, 6H), 1.30-1.36 (m, CH, CH, 2H), 0.82-0.84 (s, CH$_3$, 3H), 0.44-0.5 0 (m, CH$_2$, 2H)

<<Monomer (a03)>>

The same method as in the synthesis example of monomer (a01) was conducted, except that 343 ml of methylmagnesium bromide (THF solution, 1.0 mol/1) was changed to 245 ml of vinylmagnesium chloride (THF solution, 1.4 mol/1), so as to obtain monomer (a03) (32.0 g, yield: 53.3%).

[Chemical Formula 77.]

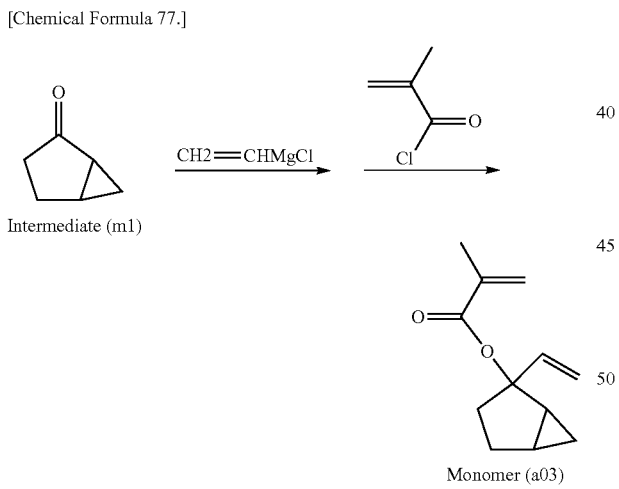

The obtained monomer (a03) was analyzed by NMR, and the structure thereof was identified by the following results.

δ(ppm)=6.18-6.22 (t, C=CH, 1H), 6.05-6.06 (s, C=CH, 1H), 5.74-5.75 (m, C=CH, 1H), 5.10-5.18 (m, C=CH$_2$, 2H), 1.86-1.88 (s, CH$_3$, 3H), 1.72-1.86 (m, CH$_2$CH$_2$, 4H), 1.32-1.38 (m, CH, CH, 2H), 0.44-0.50 (m, CH$_2$, 2H)

<<Monomer (a04)>>

The same method as in the synthesis example of monomer (a01) was conducted, except that 30.0 g of intermediate (m1) was changed to 34.4 g of intermediate (m2), so as to obtain monomer (a04) (43.0 g, yield: 71.0%).

[Chemical Formula 78.]

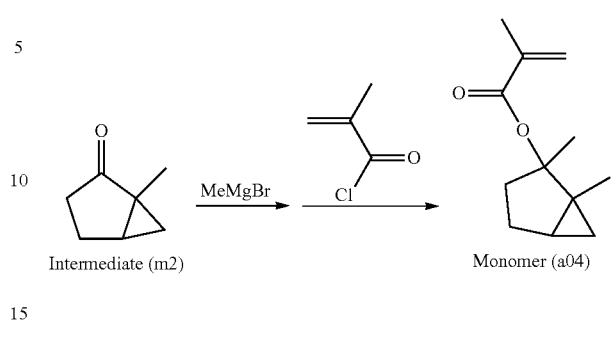

The obtained monomer (a04) was analyzed by NMR, and the structure thereof was identified by the following results.

δ(ppm)=6.05-6.06 (s, C=CH, 1H), 5.74-5.75 (m, C=CH, 1H), 1.86-1.88 (s, CH$_3$, 3H), 1.72-1.86 (m, CH$_2$CH$_2$, 4H), 1.62-1.60 (s, CH$_3$, 3H), 1.56-1.58 (s, CH$_3$, 3H), 1.32-1.34 (m, CH, 1H), 0.44-0.50 (m, CH$_2$, 2H)

<<Monomer (a05)>>

The same method as in the synthesis example of monomer (a01) was conducted, except that 30.0 g of intermediate (m1) was changed to 34.4 g of intermediate (m3), so as to obtain monomer (a05) (24.3 g, yield: 40.1%).

[Chemical Formula 79.]

The obtained monomer (a05) was analyzed by NMR, and the structure thereof was identified by the following results.

δ(ppm)=6.05-6.06 (s, C=CH, 1H), 5.74-5.75 (m, C=CH, 1H), 2.24-2.25 (m, 1H), 1.86-1.88 (s, CH$_3$, 3H), 1.25-1.70 (m, 8H), 0.44-0.50 (m, CH$_2$, 2H)

<<Monomer (a06)>>

The same method as in the synthesis example of monomer (a01) was conducted, except that 30.0 g of intermediate (m1) was changed to 38.8 g of intermediate (m4), so as to obtain intermediate (a06) (38.8 g, yield: 59.7%).

[Chemical Formula 80.]

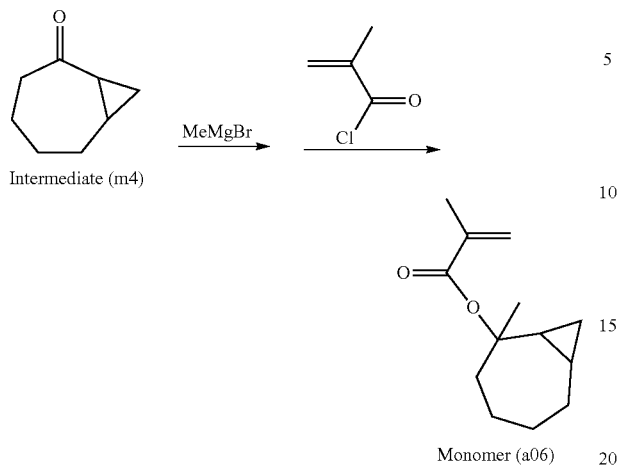

Intermediate (m4)

Monomer (a06)

The obtained monomer (a06) was analyzed by NMR, and the structure thereof was identified by the following results.

δ(ppm)=6.05-6.06 (s, C=CH, 1H), 5.74-5.75 (m, C=CH, 1H), 2.18-2.20 (m, 1H), 1.86-1.88 (s, $CH_3$, 3H), 1.45-1.75 (m, 10H), 0.44-0.50 (m, $CH_2$, 2H)

<<Monomer (a07)>>

The same method as in the synthesis example of monomer (a01) was conducted, except that 30.0 g of intermediate (m1) was changed to 34.4 g of intermediate (m5), so as to obtain monomer (a07) (37.2 g, yield: 61.4%).

[Chemical Formula 81.]

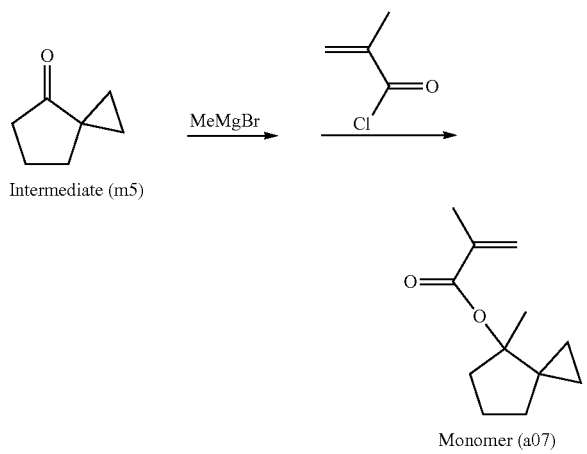

Intermediate (m5)

Monomer (a07)

The obtained monomer (a07) was analyzed by NMR, and the structure thereof was identified by the following results.

δ(ppm)=6.05-6.06 (s, C=CH, 1H), 5.74-5.75 (m, C=CH, 1H), 1.86-1.88 (s, $CH_3$, 3H), 2.12-2.15 (m, 1H), 1.57-1.75 (m, 5H), 1.50-1.52 (s, $CH_3$, 3H), 0.48-0.50 (m, $CH_2$, 4H)

<<Monomer (a08)>>

The same method as in the synthesis example of monomer (a01) was conducted, except that 30.0 g of intermediate (m1) was changed to 38.8 g of intermediate (m6), so as to obtain monomer (a08) (31.5 g, yield: 48.5%).

[Chemical Formula 82.]

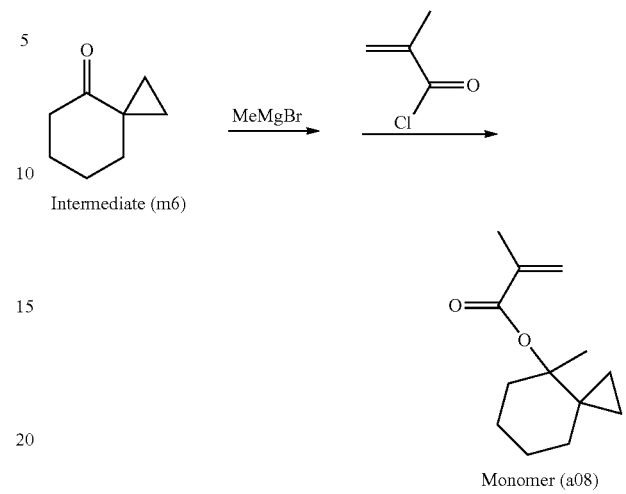

Intermediate (m6)

Monomer (a08)

The obtained monomer (a08) was analyzed by NMR, and the structure thereof was identified by the following results.

δ(ppm)=6.05-6.06 (s, C=CH, 1H), 5.74-5.75 (m, C=CH, 1H), 1.86-1.88 (s, $CH_3$, 3H), 2.18-2.20 (m, 1H), 1.69-1.80 (m, 6H), 1.50-1.52 (s, $CH_3$, 3H), 1.28-1.30 (m, 1H), 0.48-0.50 (m, $CH_2$, 4H)

<Copolymer Production Example (1)>

Copolymers (A1-1-1) to (A1-1-6) and copolymers (A2-1) to (A2-4) were produced as follows.

<<Copolymer (A1-1-1)>>

10.0 g of monomer (a21), 12.8 g of monomer (a01), 6.9 g of monomer (a31) and 2.52 g of dimethyl 2,2'-azobis(isobutyrate) (V-601) as a polymerization initiator were dissolved in 48.0 g of methyl ethyl ketone (MEK) to prepare a dripping solution. 16.8 g of MEK was added to a three-necked flask equipped with a thermometer, a reflux tube and a nitrogen-feeding pipe, and then heated to 85° C. in a nitrogen atmosphere, followed by dropwise adding the dripping solution over 4 hours. After finishing the dropwise addition, the reaction mixture was stirred at the same temperature for 1 hour. Then, the reaction liquid was cooled to room temperature. Subsequently, the obtained polymer liquid was washed by precipitating in 400 g of methanol. The obtained white solid was subjected to filtration, followed by drying under reduced pressure for one night, so as to obtain 14.8 g of the objective copolymer (A1-1-1).

[Chemical Formula 83.]

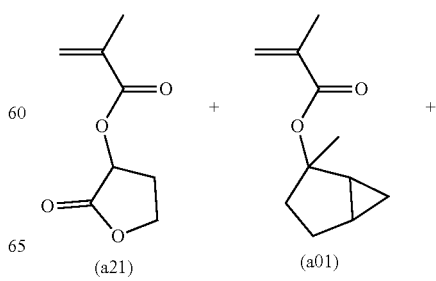

(a21)        (a01)

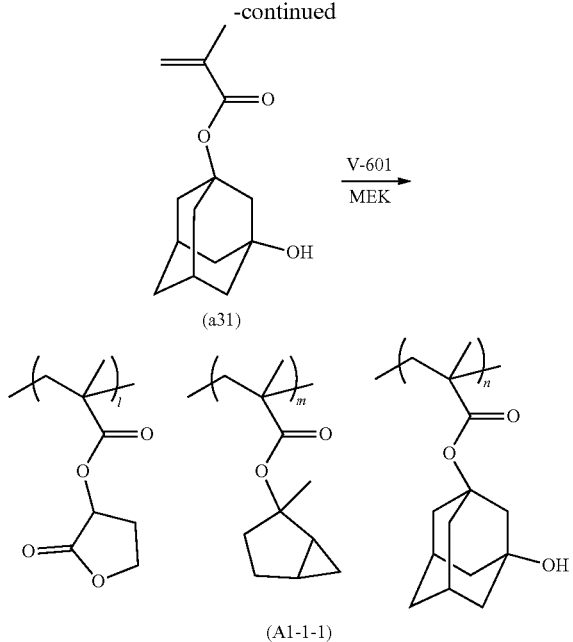

(a31)

(A1-1-1)

With respect to the obtained copolymer (A1-1-1), the weight average molecular weight (Mw) and the polydispersity (Mw/Mn) were determined by the polystyrene equivalent value as measured by gel permeation chromatography (GPC). As a result, it was found that the weight average molecular weight was 7,200, and the polydispersity was 1.78. Further, as a result of an analysis by carbon 13 nuclear magnetic resonance spectroscopy (150 MHz_$^{13}$C-NMR), it was found that the composition of the copolymer (ratio (molar ratio) of the respective structural units within the structural formula) was l/m/n=40/40/20.

Each of copolymers (A1-1-2) to (A1-1-6) and copolymers (A2-1) to (A2-4) was synthesized in substantially the same manner as in the above production example of <<Copolymer (A1-1-1)>>, except that monomers for deriving the structural units that constitute each copolymer were used in a predetermined molar ratio.

<Copolymer Production Example (2)>

Copolymers (A1-1-7) to (A1-1-12) and copolymers (A2-5) and (A2-6) were produced as follows.

<<Copolymer (A1-1-7)>>

10.0 g of monomer (a100), 20.6 g of monomer (a05) and 5.80 g of dimethyl 2,2'-azobis(isobutyrate) (V-601) as a polymerization initiator were dissolved in 64.9 g of MEK (methyl ethyl ketone) to prepare a dripping solution. 17.3 g of MEK was added to a three-necked flask equipped with a thermometer, a reflux tube and a nitrogen-feeding pipe, and then heated to 85° C. in a nitrogen atmosphere, followed by dropwise adding the dripping solution over 4 hours. After finishing the dropwise addition, the reaction mixture was stirred at the same temperature for 1 hour. Then, the reaction liquid was cooled to room temperature. Subsequently, 18.4 g of acetic acid and 262 g of methanol were added to the obtained polymer liquid, and a deprotection reaction was conducted at 30° C. for 8 hours. After the reaction finished, the obtained reaction liquid was washed by precipitating in 3,900 g of heptane. The obtained white solid was subjected to filtration, followed by drying under reduced pressure for one night, so as to obtain 13.5 g of the objective copolymer (A1-1-7).

[Chemical Formula 84.]

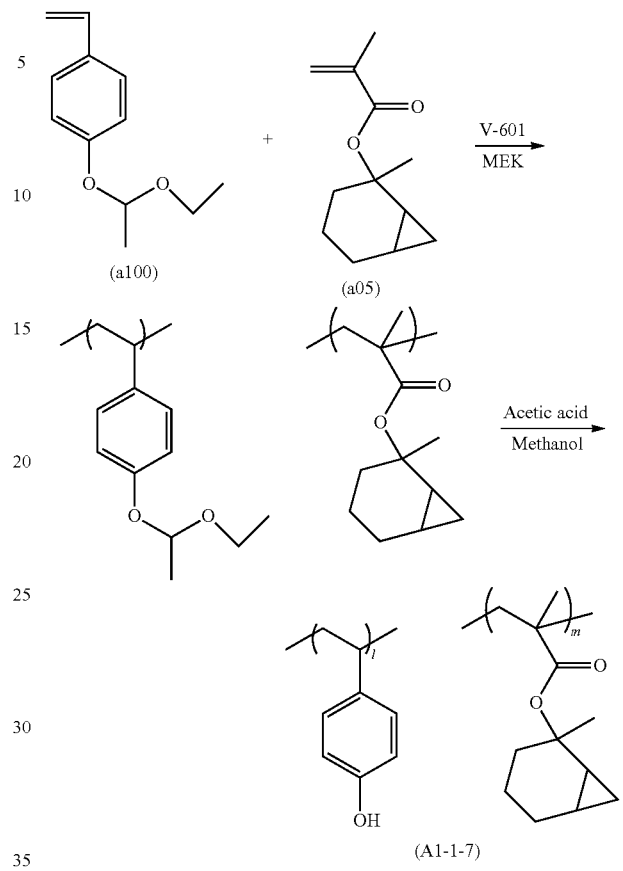

(a100)    (a05)

(A1-1-7)

With respect to the obtained copolymer (A1-1-7), the weight average molecular weight (Mw) and the polydispersity (Mw/Mn) were determined by the polystyrene equivalent value as measured by gel permeation chromatography (GPC). As a result, it was found that the weight average molecular weight was 7,200, and the polydispersity was 1.74. Further, as a result of an analysis by carbon 13 nuclear magnetic resonance spectroscopy (150 MHz_$^{13}$C-NMR), it was found that the composition of the copolymer (ratio (molar ratio) of the respective structural units within the structural formula) was l/m=40/60.

Each of copolymers (A1-1-8) to (A1-1-12) and copolymers (A2-5) and (A2-6) was synthesized in substantially the same manner as in the above production example of <<Copolymer (A1-1-7)>>, except that monomers for deriving the structural units that constitute each copolymer were used in a predetermined molar ratio.

[Chemical Formula 85.]

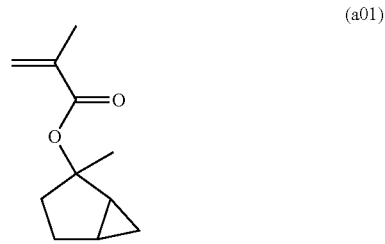

(a01)

(a02)
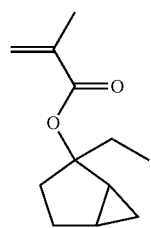
(a03)
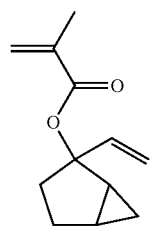
(a04)
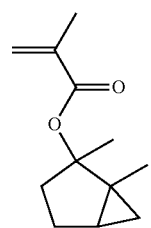
(a05)
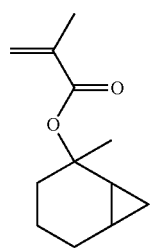
(a06)
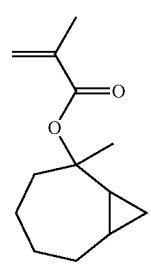
(a07)
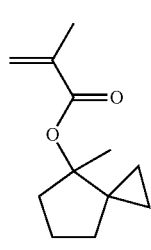
(a08)
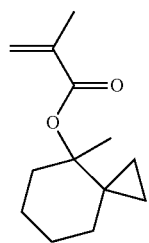
[Chemical Formula 86.]
(a100)
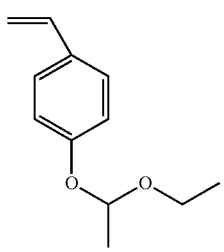
(a101)
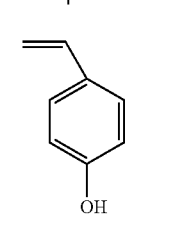
(a21)
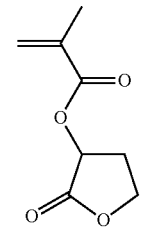
(a31)
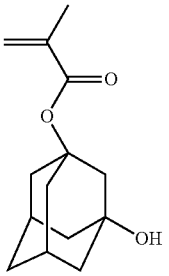
(a11)
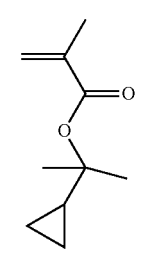

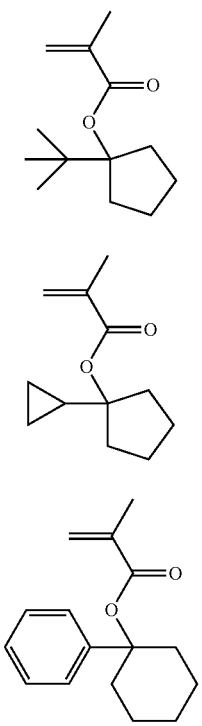
Copolymers (A1-1-1) to (A1-1-12) and copolymers (A2-1) to (A2-6) obtained in the above production examples are shown below.
[Chemical Formula 87.]
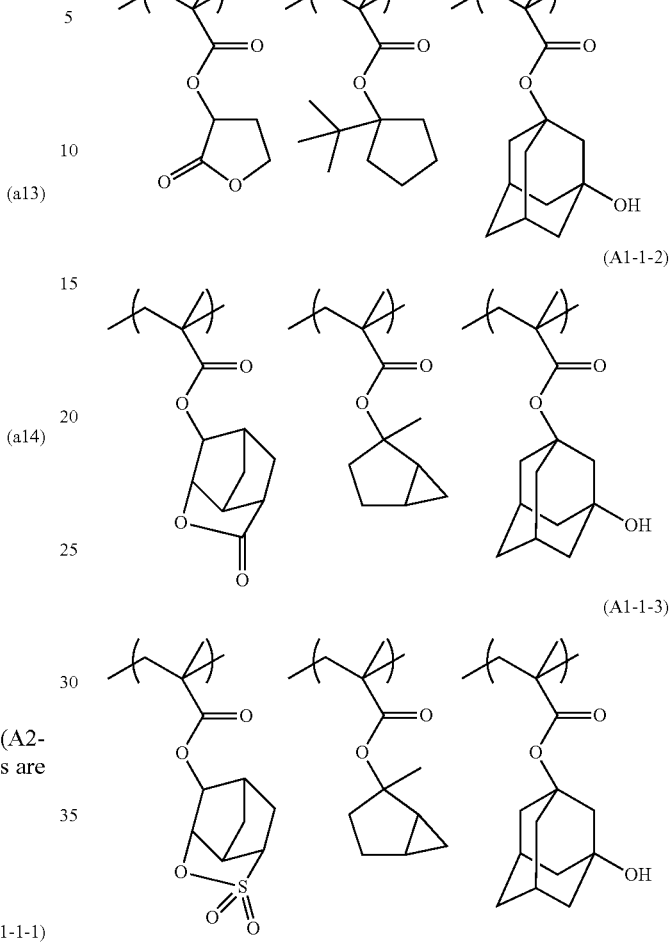
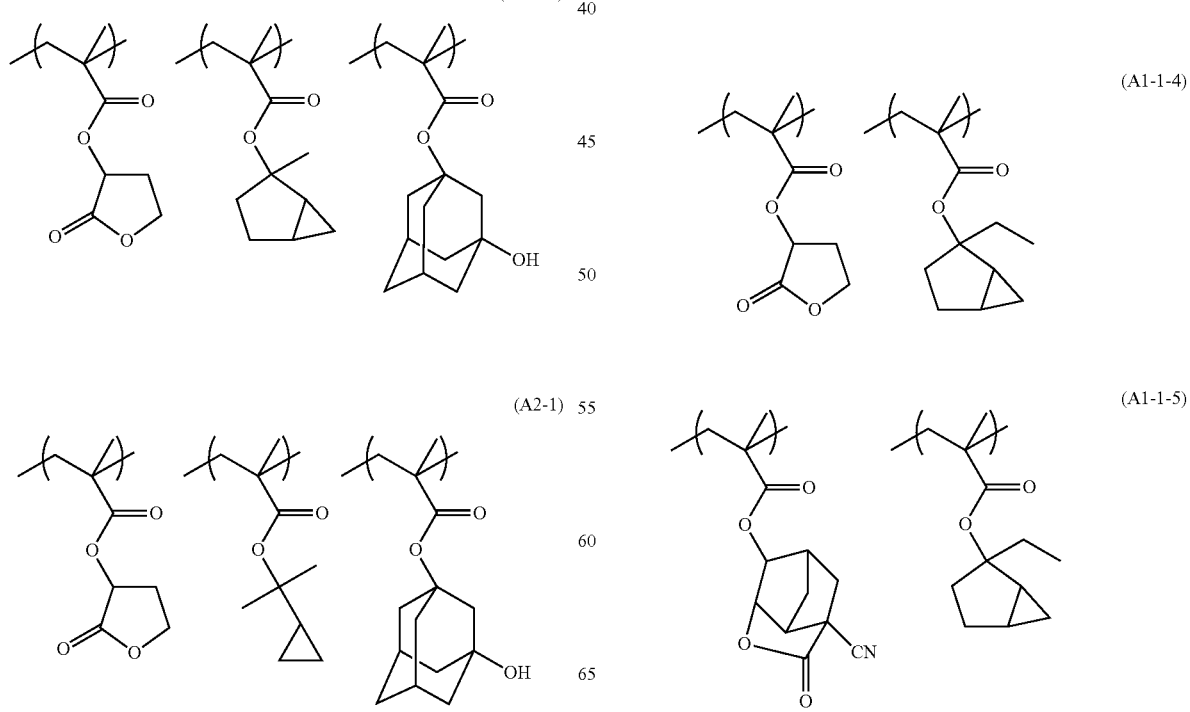

(A1-1-6)
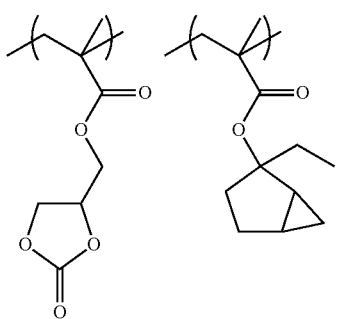

(A2-3)
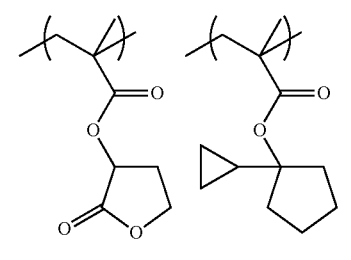

(A2-4)
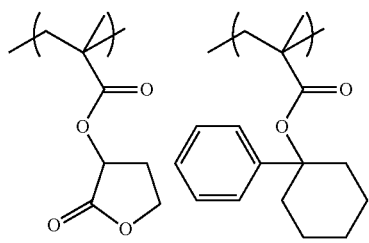

[Chemical Formula 88.]

(A1-1-7)
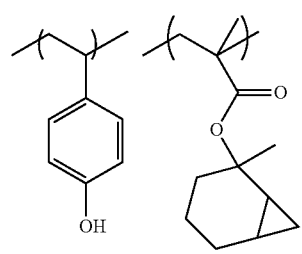

(A1-1-8)
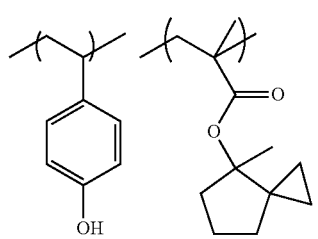

(A1-1-9)
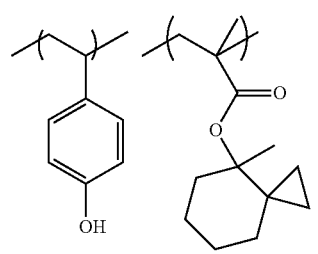

(A1-1-10)
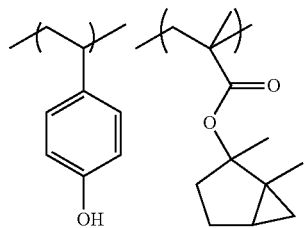

(A1-1-11)
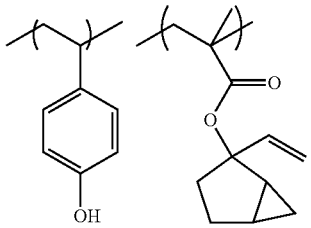

(A1-1-12)
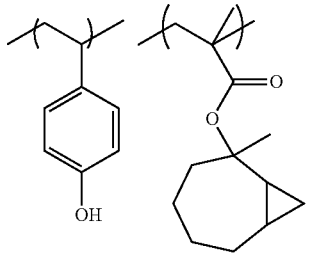

(A2-5)
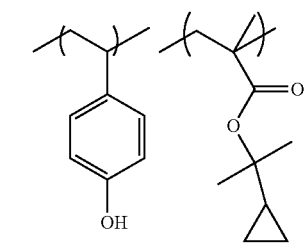

(A2-6)
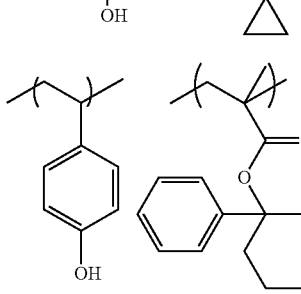

With respect to each copolymer, the compositional ratio of the polymers (the molar ratio of the respective structural units in the polymeric compound) as determined by $^{13}$C-NMR, the weight average molecular weight (Mw) and the polydispersity (Mw/Mn) determined by the polystyrene equivalent value as measured by GPC are also shown in Table 1.

TABLE 1

| Copolymer | Compositional ratio of copolymer (molar ratio) | Weight average molecular weight (Mw) | Polydispersity (Mw/Mn) |
|---|---|---|---|
| (A1-1-1) | (a21)/(a01)/(a31) = 40/40/20 | 7200 | 1.78 |
| (A2-1) | (a21)/(a11)/(a31) = 40/40/20 | 7400 | 1.72 |

TABLE 1-continued

| Copolymer | Compositional ratio of copolymer (molar ratio) | Weight average molecular weight (Mw) | Polydispersity (Mw/Mn) |
|---|---|---|---|
| (A2-2) | (a21)/(a12)/(a31) = 40/40/20 | 7600 | 1.69 |
| (A1-1-2) | (a22)/(a01)/(a31) = 40/40/20 | 6700 | 1.68 |
| (A1-1-3) | (a23)/(a01)/(a31) = 40/40/20 | 7200 | 1.77 |
| (A1-1-4) | (a21)/(a02) = 40/60 | 6900 | 1.85 |
| (A1-1-5) | (a24)/(a02) = 40/60 | 7600 | 1.88 |
| (A1-1-6) | (a25)/(a02) = 40/60 | 7800 | 1.78 |
| (A2-3) | (a21)/(a13) = 40/60 | 6600 | 1.72 |
| (A2-4) | (a21)/(a14) = 40/60 | 7000 | 1.75 |
| (A1-1-7) | (a101)/(a05) = 40/60 | 7200 | 1.74 |
| (A1-1-8) | (a101)/(a07) = 40/60 | 6900 | 1.63 |
| (A1-1-9) | (a101)/(a08) = 40/60 | 7200 | 1.68 |
| (A1-1-10) | (a101)/(a04) = 40/60 | 7000 | 1.85 |
| (A1-1-11) | (a101)/(a03) = 40/60 | 7500 | 1.85 |
| (A1-1-12) | (a101)/(a06) = 40/60 | 6900 | 1.72 |
| (A2-5) | (a101)/(a11) = 40/60 | 7200 | 1.75 |
| (A2-6) | (a101)/(a14) = 40/60 | 6800 | 1.74 |

<Production of Resist Composition>
(Examples 1 to 12, Comparative Examples 1 to 6)
The components shown in Table 2 were mixed together and dissolved to obtain each resist composition (solid content: 3.0 wt %).

TABLE 2

| | Component (A) | Component (B) | Component (D) | Component (S) | |
|---|---|---|---|---|---|
| Example 1 | (A)-1 [100] | (B)-1 [21.6] | (D)-1 [3.1] | (S)-1 [4800] | (S)-2 [3200] |
| Comparative Example 1 | (A)-2 [100] | (B)-1 [21.6] | (D)-1 [3.1] | (S)-1 [4800] | (S)-2 [3200] |
| Comparative Example 2 | (A)-3 [100] | (B)-1 [21.6] | (D)-1 [3.1] | (S)-1 [4800] | (S)-2 [3200] |
| Example 2 | (A)-4 [100] | (B)-1 [21.6] | (D)-1 [3.1] | (S)-1 [4800] | (S)-2 [3200] |
| Example 3 | (A)-5 [100] | (B)-1 [21.6] | (D)-1 [3.1] | (S)-1 [4800] | (S)-2 [3200] |
| Example 4 | (A)-6 [100] | (B)-1 [21.6] | (D)-1 [3.1] | (S)-1 [4800] | (S)-2 [3200] |
| Example 5 | (A)-7 [100] | (B)-1 [21.6] | (D)-1 [3.1] | (S)-1 [4800] | (S)-2 [3200] |
| Example 6 | (A)-8 [100] | (B)-1 [21.6] | (D)-1 [3.1] | (S)-1 [4800] | (S)-2 [3200] |
| Comparative Example 3 | (A)-9 [100] | (B)-1 [21.6] | (D)-1 [3.1] | (S)-1 [4800] | (S)-2 [3200] |
| Comparative Example 4 | (A)-10 [100] | (B)-1 [21.6] | (D)-1 [3.1] | (S)-1 [4800] | (S)-2 [3200] |
| Example 7 | (A)-11 [100] | (B)-1 [21.6] | (D)-1 [3.1] | (S)-1 [4800] | (S)-2 [3200] |
| Example 8 | (A)-12 [100] | (B)-1 [21.6] | (D)-1 [3.1] | (S)-1 [4800] | (S)-2 [3200] |
| Example 9 | (A)-13 [100] | (B)-1 [21.6] | (D)-1 [3.1] | (S)-1 [4800] | (S)-2 [3200] |
| Example 10 | (A)-14 [100] | (B)-1 [21.6] | (D)-1 [3.1] | (S)-1 [4800] | (S)-2 [3200] |
| Example 11 | (A)-15 [100] | (B)-1 [21.6] | (D)-1 [3.1] | (S)-1 [4800] | (S)-2 [3200] |
| Example 12 | (A)-16 [100] | (B)-1 [21.6] | (D)-1 [3.1] | (S)-1 [4800] | (S)-2 [3200] |
| Comparative Example 5 | (A)-17 [100] | (B)-1 [21.6] | (D)-1 [3.1] | (S)-1 [4800] | (S)-2 [3200] |
| Comparative Example 6 | (A)-18 [100] | (B)-1 [21.6] | (D)-1 [3.1] | (S)-1 [4800] | (S)-2 [3200] |

In Table 2, the reference characters indicate the following. The values in brackets [ ] indicate the amount (in terms of parts by weight) of the component added.
(A)-1: The above copolymer (A1-1-1)
(A)-2: The above copolymer (A2-1)
(A)-3: The above copolymer (A2-2)
(A)-4 to (A)-8: The above copolymers (A1-1-2) to (A1-1-6)
(A)-9: The above copolymer (A2-3)
(A)-10: The above copolymer (A2-4)
(A)-11 to (A)-16: The above copolymers (A1-1-7) to (A1-1-12)
(A)-17: The above copolymer (A2-5)
(A)-18: The above copolymer (A2-6)
(B)-1: an acid generator consisting of a compound represented by chemical formula (B)-1 shown below
(D)-1: acid diffusion control agent of a compound represented by chemical formula (D)-1 below
(S)-1: propyleneglycol monomethyletheracetate
(S)-2: propylene glycol monomethyl ether

[Chemical Formula 89.]

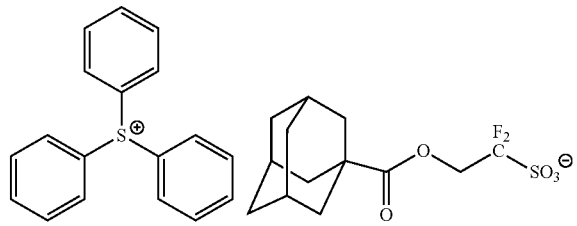

(B)-1

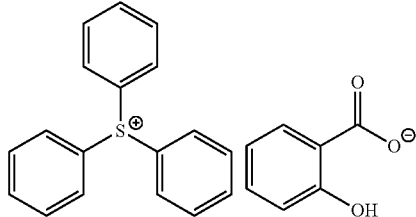

(D)-1

<Formation of Resist Pattern>
Each of the resist compositions of examples and comparative examples was applied to an 8-inch silicon substrate which had been treated with hexamethyldisilazane (HMDS) using a spinner, and was then prebaked (PAB) on a hot plate at 110° C. for 60 seconds and dried, thereby forming a resist film having a film thickness of 30 nm. Subsequently, the resist film was subjected to drawing (exposure) using an electron beam lithography apparatus JEOL JBX-9300FS (manufactured by JEOL Ltd.) at an acceleration voltage of 100 kV, targeting a 1:1 line and space pattern (hereafter, referred to as "L/S pattern") having lines with a width of 50. Then, a post exposure bake (PEB) treatment was conducted at 110° C. for 60 seconds.

Thereafter, alkali developing was conducted for 60 seconds at 23° C. in a 2.38% by weight aqueous solution of tetramethylammonium hydroxide (TMAH) (product name: NMD-3; manufactured by Tokyo Ohka Kogyo Co., Ltd.). Then, water rinsing was conducted for 15 seconds using pure water.

As a result, a 1:1 line and space pattern (LS pattern) having a line width of 50 nm was formed.
[Evaluation of Optimum Exposure Dose (Eop)]
The optimum exposure dose Eop (C/cm$^2$) with which the LS pattern was formed in the above formation of resist pattern was determined. The results are indicated under "Eop(μC/cm$^2$)" in Table 3.

[Evaluation of Line Width Roughness (LWR)]

With respect to a resist pattern formed by the above method of "Formation of resist pattern", 3σ was determined as a yardstick for indicating LWR. The results are indicated under "LWR (nm)" in Table 3.

"3σ" indicates a value of 3 times the standard deviation (σ) (i.e., 3σ) (unit: nm) determined by measuring the line positions at 400 points in the lengthwise direction of the line using a scanning electron microscope (product name: S-9380, manufactured by Hitachi High-Technologies Corporation; acceleration voltage: 800V).

The smaller this 3σ value is, the lower the level of roughness on the side walls of the line, indicating that an L/S pattern with a uniform width was obtained.

[Evaluation of Resolution]

The critical resolution (nm) with the above Eop was determined using a scanning electron microscope (product name: S-9380, manufactured by Hitachi High-Technologies Corporation). Specifically, the exposure dose was gradually increased from the optimum exposure dose Eop, and the minimum size of the pattern which resolves without collapse (fall) was determined. The results are indicated under "Critical resolution (nm)" in Table 3.

TABLE 3

| | PAB (° C.) | PEB (° C.) | Eop (μC/cm$^2$) | LWR (nm) | Critical resolution (nm) |
|---|---|---|---|---|---|
| Example 1 | 110 | 110 | 95 | 6.0 | 30 |
| Comparative Example 1 | 110 | 110 | 135 | 6.4 | 45 |
| Comparative Example 2 | 110 | 110 | 105 | 6.7 | 40 |
| Example 2 | 110 | 110 | 105 | 5.9 | 35 |
| Example 3 | 110 | 110 | 100 | 6.2 | 30 |
| Example 4 | 110 | 110 | 90 | 6.0 | 30 |
| Example 5 | 110 | 110 | 95 | 6.0 | 28 |
| Example 6 | 110 | 110 | 90 | 6.2 | 30 |
| Comparative Example 3 | 110 | 110 | 130 | 6.3 | 45 |
| Comparative Example 4 | 110 | 110 | 120 | 6.6 | 40 |
| Example 7 | 110 | 110 | 65 | 5.2 | 26 |
| Example 8 | 110 | 110 | 55 | 5.6 | 28 |
| Example 9 | 110 | 110 | 50 | 5.8 | 28 |
| Example 10 | 110 | 110 | 60 | 5.5 | 28 |
| Example 11 | 110 | 110 | 55 | 5.4 | 28 |
| Example 12 | 110 | 110 | 60 | 5.8 | 30 |
| Comparative Example 5 | 110 | 110 | 90 | 6.6 | 32 |
| Comparative Example 6 | 110 | 110 | 85 | 6.4 | 35 |

As seen from the results shown in Table 3, from comparison between Example 1 and Comparative Examples 1 and 2, comparison between Example 2 to 6 and Comparative Examples 3 and 4, and comparison between Examples 7 to 12 and Comparative Examples 5 and 6, according to the resist composition of the examples which applied the present invention, high sensitivity can be achieved in the formation of a resist pattern, and a resist pattern exhibiting excellent lithography properties (resolution, reduced roughness) can be formed, as compared to the comparative examples.

What is claimed is:

1. A compound represented by general formula (a0-1-1) or (a0-1-2) shown below:

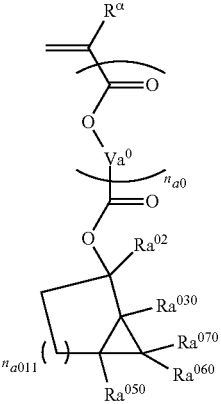

(a0-1-1)

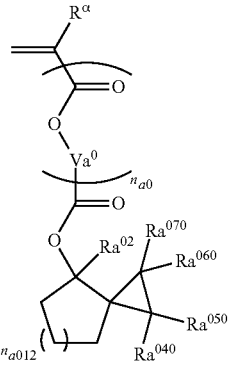

(a0-1-2)

wherein, in formula (a0-1-1), $R^\alpha$ represents a hydrogen atom, a methyl group or a trifluoromethyl group; $Va^0$ represents a linear or branched alkylene group which may have an ether bond;

$n_{a0}$ represents an integer of 0 to 2; $n_{a011}$ represents an integer of 1 to 4; $Ra^{02}$ represents a hydrocarbon group which may have a substituent; $Ra^{030}$ represents a hydrogen atom or an alkyl group having 1 to 5 carbon atoms; $Ra^{050}$ to $Ra^{070}$ each independently represents a hydrogen atom or an alkyl group having 1 to 5 carbon atoms; in formula (a0-1-2), $R^\alpha$ represents a hydrogen atom, a methyl group or a trifluoromethyl group; $Va^0$ represents a linear or branched alkylene group which may have an ether bond; $n_{a0}$ represents an integer of 0 to 2; $n_{a012}$ represents an integer of 1 to 4; $Ra^{02}$ represents a hydrocarbon group which may have a substituent;

$Ra^{040}$ represents a hydrogen atom or an alkyl group having 1 to 5 carbon atoms; and $Ra^{050}$ to $Ra^{070}$ each independently represents a hydrogen atom or an alkyl group having 1 to 5 carbon atoms; provided that $Ra^{02}$, $Ra^{030}$, $Ra^{060}$ and $Ra^{070}$ are not bonded to each other.

2. A polymeric compound comprising a structural unit (a0) derived from the compound represented by general formula (a0-1-1) or (a0-1-2) according to claim 1.

3. A resist composition which generates acid upon exposure and exhibits changed solubility in a developing solution under action of acid, the resist composition comprising:
a resin component (A1) which exhibits changed solubility in a developing solution under action of acid, the resin component (A1) comprising a structural unit (a0) derived from the compound represented by general formula (a0-1-1) or (a0-1-2) according to claim 1.

4. A method of forming a resist pattern, comprising:

forming a resist film using the resist composition according to claim 3;

exposing the resist film, and developing the exposed resist film to form a resist pattern.

\* \* \* \* \*

UNITED STATES PATENT AND TRADEMARK OFFICE
CERTIFICATE OF CORRECTION

| | | |
|---|---|---|
| PATENT NO. | : 11,061,329 B2 | Page 1 of 1 |
| APPLICATION NO. | : 16/173326 | |
| DATED | : July 13, 2021 | |
| INVENTOR(S) | : Takuya Ikeda and Masatoshi Arai | |

It is certified that error appears in the above-identified patent and that said Letters Patent is hereby corrected as shown below:

In the Specification

In Column 4, Line 60, delete "hydroxyalkylgroup" and insert -- hydroxyalkyl group --.
In Column 7, Line 18, delete "(hereafter," and insert -- hereafter, --.
In Column 17, Line 54, delete "(4n+2) it" and insert -- (4n+2)π --.
In Column 30, Line 56 (approx.), delete "(a1-r-2-1)" and insert -- (a1-r2-1) --.
In Column 30, Line 61 (approx.), delete "(a1-r-2-2)" and insert -- (a1-r2-2) --.
In Column 31, Line 19 (approx.), delete "$Ra^{03}$" and insert -- $Ra^{03}$, --.
In Column 41, Line 24, delete "$R^1$" and insert -- $R^α$ --.
In Column 79, Line 27, delete "heteratom." and insert -- heteroatom. --.
In Column 79, Line 50 (approx.), delete "$R^1$" and insert -- $R^α$ --.
In Column 87, Lines 48-49, delete "tetracyclodpdecane," and insert -- tetracyclododecane, --.
In Column 89, Line 51 (approx.), delete "$R^1$," and insert -- $R^{101}$, --.
In Column 96, Line 40 (approx.), delete "naphthylene" and insert -- naphthalene --.
In Column 123, Line 30, delete "dihphenyliodonium" and insert -- diphenyliodonium --.
In Column 135, Line 60, delete "alkylalcoholamines)," and insert -- alkyl alcohol amines), --.
In Column 135, Line 61, delete "alkylalcoholamines" and insert -- alkyl alcohol amines --.
In Column 142, Lines 51-52, delete "diethyleneglycol" and insert -- diethylene glycol --.
In Column 143, Line 1, delete "diacetonylalcohol," and insert -- diacetone alcohol, --.
In Column 164, Line 13 (approx.), delete "propyleneglycol monomethyletheracetate" and insert -- propylene glycol monomethyl ether acetate --.
In Column 164, Line 64, delete "$(C/cm^2)$" and insert -- $(μC/cm^2)$ --.

In the Claims

In Column 166, Line 59, Claim 1, delete "$Ra^{030}$," and insert -- $Ra^{030}$, $Ra^{050}$, --.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*